United States Patent
Torii et al.

(10) Patent No.: US 9,180,220 B2
(45) Date of Patent: Nov. 10, 2015

(54) WATER ABSORBING AGENT, WATER ABSORBENT CORE USING THE AGENT, AND MANUFACTURING METHOD FOR WATER ABSORBING AGENT

(75) Inventors: Kazushi Torii, Hyogo (JP); Hirofumi Shibata, Hyogo (JP); Kazuki Kimura, Hyogo (JP); Yasuhisa Nakashima, Hyogo (JP); Motohiro Imura, Hyogo (JP); Hiroko Ueda, Hyogo (JP); Katsuyuki Wada, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 13/467,236

(22) Filed: May 9, 2012

(65) Prior Publication Data

US 2012/0305842 A1 Dec. 6, 2012

Related U.S. Application Data

(62) Division of application No. 12/294,328, filed as application No. PCT/JP2007/056527 on Mar. 20, 2007, now Pat. No. 8,198,209.

(30) Foreign Application Priority Data

Mar. 27, 2006 (JP) ................................. 2006-085652
Jul. 7, 2006 (JP) ................................. 2006-188668
Dec. 28, 2006 (JP) ................................. 2006-355202

(51) Int. Cl.
*C08G 63/91* (2006.01)
*C08F 20/00* (2006.01)
(Continued)

(52) U.S. Cl.
CPC ................. *A61L 15/60* (2013.01); *A61L 15/18* (2013.01); *B01J 20/103* (2013.01); *B01J 20/26* (2013.01);
(Continued)

(58) Field of Classification Search
USPC ........ 106/287.17, 287.34; 423/335, 409, 413; 502/400, 401, 405, 407, 411, 414, 439; 525/7.2; 526/317.1, 328; 528/395
See application file for complete search history.

(56) References Cited

U.S. PATENT DOCUMENTS 3,935,099 A  1/1976  Weaver et al.
3,959,569 A  5/1976  Burkholder, Jr.
(Continued)

FOREIGN PATENT DOCUMENTS

CN  1455802  11/2003
EP  0456136  11/1991
(Continued)

OTHER PUBLICATIONS

"Aluminum sulfate, solid." Delta Chem. Corp., Jan. 7, 2011. Viewed May 10, 2013 at http://www.deltachemical.com/PDFS/DeltaAlumSolid.pdf.*

(Continued)

*Primary Examiner* — Stuart Hendrickson
*Assistant Examiner* — Daniel Berns
(74) *Attorney, Agent, or Firm* — Amin, Turocy & Watson, LLP

(57) ABSTRACT

A water absorbing agent of the present invention has an internal crosslinking structure obtained by polymerization of a water-soluble unsaturated monomer. The agent satisfies conditions (a) to (d): (a) the agent contains water-insoluble inorganic particles at an amount of from 10 ppm to 1,900 ppm inclusive; (b) the agent contains 5 mass % or less particles which have such a size that they can pass through a sieve having a mesh opening size of 150 μm; (c) the agent has an absorbency against a pressure of 4.83 kPa (AAP) of 18 g/g or more; and (d) the water-insoluble inorganic particles reside on a surface of the water absorbing resin or near the surface.

6 Claims, 1 Drawing Sheet

(51) Int. Cl.

| | | |
|---|---|---|
| *B01J 20/10* | (2006.01) | |
| *B01J 20/22* | (2006.01) | |
| *B01J 20/28* | (2006.01) | |
| *B01J 20/32* | (2006.01) | |
| *A61L 15/60* | (2006.01) | |
| *A61L 15/18* | (2006.01) | |
| *B01J 20/26* | (2006.01) | |
| *C08L 101/14* | (2006.01) | |

(52) U.S. Cl.
CPC .............. *B01J 20/261* (2013.01); *B01J 20/267* (2013.01); *C08L 101/14* (2013.01); *B01J 2220/46* (2013.01); *B01J 2220/68* (2013.01); *Y10T 428/253* (2015.01)

(56) References Cited

U.S. PATENT DOCUMENTS

| | | | |
|---|---|---|---|
| 4,076,663 | A | 2/1978 | Masuda et al. |
| 4,093,776 | A | 6/1978 | Aoki et al. |
| 4,121,946 | A | 10/1978 | Chuiko et al. |
| 4,124,748 | A | 11/1978 | Fujimoto et al. |
| 4,367,323 | A | 1/1983 | Kitamura et al. |
| 4,389,513 | A | 6/1983 | Miyazaki |
| 4,446,261 | A | 5/1984 | Yamasaki et al. |
| 4,625,001 | A | 11/1986 | Tsubakimoto et al. |
| 4,654,039 | A | 3/1987 | Brandt et al. |
| 4,683,274 | A | 7/1987 | Nakamura et al. |
| 4,690,996 | A | 9/1987 | Shih et al. |
| 4,721,647 | A | 1/1988 | Nakanishi et al. |
| 4,738,867 | A | 4/1988 | Itoh et al. |
| 4,748,076 | A | 5/1988 | Saotome |
| 4,769,427 | A | 9/1988 | Nowakowsky et al. |
| 4,873,299 | A | 10/1989 | Nowakowsky et al. |
| 4,950,692 | A | 8/1990 | Lewis et al. |
| 5,164,459 | A | 11/1992 | Kimura et al. |
| 5,192,606 | A | 3/1993 | Proxmire et al. |
| 5,250,640 | A | 10/1993 | Irie et al. |
| 5,264,495 | A | 11/1993 | Irie et al. |
| 5,275,773 | A | 1/1994 | Irie et al. |
| 5,478,879 | A | 12/1995 | Kajikawa et al. |
| 5,509,915 | A | 4/1996 | Hanson et al. |
| 5,668,078 | A | 9/1997 | Sumiya et al. |
| 5,849,405 | A | 12/1998 | Wang et al. |
| 6,071,976 | A | 6/2000 | Dairoku et al. |
| 6,228,930 | B1 | 5/2001 | Dairoku et al. |
| 6,300,423 | B1 | 10/2001 | Englhardt et al. |
| 6,469,080 | B2 | 10/2002 | Miyake et al. |
| 6,562,879 | B1 | 5/2003 | Hatsuda et al. |
| 6,565,768 | B1 | 5/2003 | Dentler et al. |
| 2002/0040095 | A1 | 4/2002 | Dairoku et al. |
| 2002/0128618 | A1 | 9/2002 | Frenz et al. |
| 2003/0060112 | A1 | 3/2003 | Rezai et al. |
| 2003/0069359 | A1 | 4/2003 | Torii et al. |
| 2004/0048955 | A1 | 3/2004 | Wada et al. |
| 2005/0003191 | A1 | 1/2005 | Ehrnsperger et al. |
| 2005/0209352 | A1 | 9/2005 | Dairoku et al. |
| 2006/0073969 | A1 | 4/2006 | Torii et al. |
| 2006/0204755 | A1 | 9/2006 | Torii et al. |
| 2007/0106013 | A1 | 5/2007 | Adachi et al. |
| 2008/0119586 | A1 | 5/2008 | Byerly et al. |

FOREIGN PATENT DOCUMENTS

| | | |
|---|---|---|
| EP | 0668080 | 8/1995 |
| EP | 0761241 | 3/1997 |
| EP | 0844270 | 5/1998 |
| EP | 1352927 | 10/2003 |
| JP | 56-133028 | 10/1981 |
| JP | 64-004653 | 1/1989 |
| JP | 06-041319 | 2/1994 |
| JP | 09-136966 | 5/1997 |
| JP | 2000-093792 | 4/2000 |
| JP | 2003-088551 | 3/2003 |
| JP | 2003-088553 | 3/2003 |
| WO | 0071176 | 11/2000 |
| WO | 2004069293 | 8/2004 |
| WO | 2004069915 | 8/2004 |
| WO | 2004113452 | 12/2004 |
| WO | 2005010102 | 2/2005 |
| WO | 2005027986 | 3/2005 |
| WO | 2006033477 | 3/2006 |
| WO | 2006063229 | 6/2006 |
| WO | 2008055935 | 5/2008 |

OTHER PUBLICATIONS

United States Office Action for U.S. Appl. No. 12/294,328 mailed on Oct. 6, 2011.
Office Action for Chinese Patent Application No. 201210129711.X Dated Nov. 12, 2013, 14 pgs.
Communication pursuant to Rule 114(2)EPC against Corresponding EPC patent application No. 07739965.7 (A Third Party Observation), 16 pages, dated Apr. 16, 2015.

* cited by examiner

WATER ABSORBING AGENT, WATER ABSORBENT CORE USING THE AGENT, AND MANUFACTURING METHOD FOR WATER ABSORBING AGENT

CROSS-REFERENCE TO RELATED APPLICATIONS

This application is a Division of application Ser. No. 12/294,328 filed on Sep. 24, 2008, the entire contents of which are incorporated herein by reference.

TECHNICAL FIELD

The present invention relates to water absorbing agents, water absorbent cores using the agents, and manufacturing methods for the water absorbing agents. Specifically, the present invention relates to water absorbing agents, water absorbent cores, and manufacturing methods for the water absorbing agents which are suitably applicable to disposable diapers, sanitary napkins, so-called incontinent pads, and other sanitary/hygienic materials.

BACKGROUND ART

Water absorbent cores containing hydrophilic fiber, such as pulp, and a water absorbing resin particles are widely used conventionally so that sanitary/hygienic materials, such as disposable diapers, sanitary napkins, and incontinent pads, can absorb body fluids. The water absorbent core is used in sanitary/hygienic materials, such as disposable diapers, sanitary napkins, and incontinent pads, to absorb body fluids.

There are recent demands for these sanitary/hygienic materials to be reduced in thickness for better usability. Therefore water absorbent cores are manufactured with a decreasing ratio of hydrophilic fiber, which has a relatively low bulk density, and an increasing ratio of water absorbing resin particles, which exhibit excellent water absorption and a relatively high bulk density. The relative quantity of water absorbing resin particles used in the water absorbent core is hence increased, which in turn reduces the thickness of the sanitary/hygienic materials without compromising water absorbency and other physical properties.

The ratio of the hydrophilic fiber may be decreased, but not further below a minimum quantity required. For further reduction in thickness of the sanitary/hygienic materials, the physical properties of the water absorbing resin particles need to be improved. Examples of such physical properties of the water absorbing resin particles include centrifuge retention capacity, saline flow conductivity, absorbency against pressure, fixed height absorbency, mass median particle size, and liquid distribution velocity. These physical properties of the water absorbing resin particles need to be in predetermined ranges or excellent in actual use.

In, for example, a diaper which contains a sanitary/hygienic material with a high proportion of water absorbing resin particles, the water absorbing resin particles absorb water and changes into gel or a similar condition. That may lead to a phenomenon called gel blocking. The phenomenon reduces liquid diffusibility of the sanitary/hygienic material.

A method of adding inorganic particles to the water absorbing resin particles has been proposed to improve the physical properties of the water absorbing resin particles and address the gel blocking problem. According to the method, the inorganic particles are present between the water absorbing resin particles, thereby preventing the water absorbing resin particles from aggregating. The gel blocking problem is mitigated.

Patent document 1 discloses a water absorbing agent composition as water absorbing resin particles used with inorganic particles. The composition contains crosslinked, water-swelling resin powder and hydrophobic superfine particulate silica. The composition is intended to achieve good fluidity in powder form, not to get sticky when having absorbed moisture (thus allowing for easy handling), and to show excellent water absorption and water retention capabilities.

Patent document 2 discloses a water absorbing polymer agent composition. The composition is prepared by sticking inorganic fine powder in a secondary aggregate state to the surface of a water absorbing polymer agent in coarse particle form. This particular method of preparation is a feature of the composition. The composition is intended to achieve excellent fluidity and a high liquid absorption rate.

Patent document 3 discloses modified water absorbing resin particles for use in sanitary products. The particles show an increased absorption rate and causes less gel blocking. The particles are a crosslinked polymer of an unsaturated ethylenic monomer that has an acrylic acid and/or an acrylic acid salt as major structural units. The particles are treated with liquid organic polysiloxane at normal temperature.

Patent document 4 discloses modified water absorbing resin particles. The particles show an increased absorption rate, and cause mitigated moisture-driven blocking and restrained dust production. The particles are prepared by treating water absorbing resin particles with a silicone-based surfactant.

Patent document 5 discloses a water absorbing agent prepared from inorganic powder and water absorbing resin. The agent causes mitigated blocking when having absorbed moisture, offers easy handling, and shows excellent absorption properties under load. The inorganic powder exhibits a pH from 7 to 10, inclusive, when dispersed in a liquid, and a specific surface area of 50 $m^2$/g or more as measured by BET.

Patent document 6 discloses a water absorbent core containing a water absorbing resin and a hydrophilic fiber. The core exhibits an absorbency under load of 10 g/g or less for artificial urine 30 seconds after absorption is started and a water absorbency under load of 20 g/g or more for artificial urine 30 minutes after absorption of water is started. The core is intended to achieve reduced thickness without causing problems in actual use.

Patent document 7 discloses a water absorbent core containing a water absorbing resin and a hydrophilic resin. The water absorbing resin exhibits an absorption swelling pressure of 10,000 Pa or less for physiological saline as the test solution and an absorption swelling pressure of 80,000 Pa or higher 300 seconds after absorption of water is started. The core is intended to achieve excellent liquid diffusibility and a low level of liquid seeping.

Patent document 8 discloses a technique of using 3D spacers in the preparation of a water absorbing resin.

Patent document 9 discloses a particulate water absorbing agent containing water absorbing resin particles and a liquid permeability improver. The particles are prepared by polymerizing (crosslinking) a monomer of an acrylic acid and/or its salt and further crosslinking the surface of the resultant irregularly pulverized particles. The agent is intended to be superior in both physical properties: capillary suction force and liquid permeability.

Patent document 10 discloses a water absorbing resin composition that contains a monomer with carboxyl groups and fumed silica for improved deodorizing effects and fluidity.

Patent document 11 discloses a technique of adding a liquid permeability improver to a water absorbing resin in the preparation of a water absorbing resin.

[Patent Document 1] Japanese Unexamined Patent Publication 56-133028/1981 (Tokukaisho 56-133028; published Oct. 17, 1981)
[Patent Document 2] Japanese Unexamined Patent Publication 64-4653/1989 (Tokukaisho 64-4653; published Jan. 9, 1989)
[Patent Document 3] Japanese Patent 3169133, Specification (registered Mar. 16, 2001)
[Patent Document 4] Japanese Unexamined Patent Publication 9-136966/1997 (Tokukaihei 9-136966; published May 27, 1997)
[Patent Document 5] Japanese Unexamined Patent Publication (Tokukai) 2000-93792 (published Apr. 4, 2000)
[Patent Document 6] Japanese Unexamined Patent Publication (Tokukai) 2003-88551 (published Mar. 25, 2003)
[Patent Document 7] Japanese Unexamined Patent Publication (Tokukai) 2003-88553 (published Mar. 25, 2003)
[Patent Document 8] U.S. Published Patent Application 2002/0128618, Specification (Sep. 12, 2002)
[Patent Document 9] Japanese Unexamined Patent Publication (Tokukai) 2004-261797 (published Sep. 24, 2004)
[Patent Document 10] Published Japanese Translation of PCT Application (Tokuhyo) 2003-500490 (published Jan. 7, 2003)
[Patent Document 11] International Application Published under PCT WO2004/69915 (Aug. 19, 2004)

DISCLOSURE OF INVENTION

The conventional techniques listed above have a problem that they cannot deliver a water absorbing agent with necessary physical properties as water absorbing resin or achieve limited dust production in the manufacture of water absorbing resin.

Specifically, water absorbing resin is required to exhibit good physical properties (centrifuge retention capacity, saline flow conductivity, absorbency against pressure, fixed height absorbency, mass median particle size, liquid diffusibility, etc.) in the actual use of the water absorbing resin. Conventional technology has so far failed to achieve sufficient values with these physical properties. One factor in the failure is the trade-off between centrifuge retention capacity and saline flow conductivity, both of which are important physical properties for water absorbing resin: if either of the physical properties improves, the other suffers. It is difficult to achieve good values with both of the physical properties.

In addition, in conventional technology, if inorganic particles are added to the water absorbing resin, a new problem arises that dust could be created from the inorganic particles. The dust may reduce the manufacturing efficiency for the water absorbing resin, degrade the physical properties of the water absorbing resin, or raise safety/hygienic concerns. Especially, when the inorganic particles is used in 0.2 mass % or more to the water absorbing resin, dust is likely to occur due to the relative abundance of the inorganic particles used.

The present invention, conceived in view of these conventional issues, has an object of providing a water absorbing agent and a water absorbent core which exhibit excellent physical properties and are unlikely to create dust, and also providing a method of manufacturing the water absorbing agent.

A water absorbing agent of the present invention is, in order to solve the problems, characterized in that it contains water absorbing resin particles with an internal crosslinking structure obtained by polymerization of a water-soluble unsaturated monomer. The agent is further characterized in that it satisfies conditions (a) to (d) below:

(a) the agent contains water-insoluble inorganic particles at an amount of from 10 ppm to 1,900 ppm inclusive;

(b) the agent contains 5 mass % or less particles which have such a size that they can pass through a sieve having a mesh opening size of 150 µm;

(c) the agent has an absorbency against a pressure of 4.83 kPa (AAP) of 18 g/g or more; and (d) the water-insoluble inorganic particles reside on a surface of the water absorbing resin or near the surface.

The water absorbing agent of the present invention is preferably such that the water-insoluble inorganic particles account for 10 ppm to 990 ppm, inclusive, of the agent.

The water absorbing agent of the present invention is preferably such that the water-insoluble inorganic particles contain amino groups residing at least on the surface of the particles.

The water absorbing agent of the present invention is preferably such that: the water-insoluble inorganic particles are silicon dioxide; and the silicon dioxide has, on a surface thereof, residual silanol groups at a concentration of 1.7 $SiOH/nm^2$ or lower.

The water absorbing agent of the present invention is preferably such that the water absorbing agent has a saline flow conductivity (SFC) of 30 ($10^{-7} \cdot cm^3 \cdot s \cdot g^{-1}$) or more.

The water absorbing agent of the present invention preferably has an absorbency against a pressure of 4.83 kPa (AAP) of 20 g/g to 30 g/g inclusive.

The water absorbing agent of the present invention preferably further contains an at least trivalent water-soluble polyvalent metal salt at an amount of from 0.1 mass % to 1 mass % inclusive.

The water absorbing agent of the present invention is preferably such that the water-soluble polyvalent metal salt is aluminum sulfate.

The water absorbing agent of the present invention is preferably such that the water absorbing resin particles contain particles with a porous structure.

The water absorbing agent of the present invention is preferably such that: the agent has a mass median particle size of 200 µm to 500 µm inclusive and a logarithmic standard deviation, $\sigma\zeta$, of a particle size distribution of 0.20 to 0.40 inclusive.

The water absorbing agent of the present invention preferably has a liquid distribution velocity (LDV) of 0.2 (mm/sec) to 10.0 (mm/sec) inclusive.

The water absorbing agent of the present invention preferably has a negative frictional electric charge.

The water absorbing agent of the present invention preferably contains 300 ppm or less dust by mass.

The water absorbing agent of the present invention preferably contains dust in such an amount that the dust contains $SiO_2$ which is 50 mass % or less.

The water absorbing agent of the present invention is preferably obtained by a method of manufacturing which involves the step of mixing the silicon dioxide with the water absorbing resin particles after giving mechanical damage to the water absorbing resin particles.

The water absorbing agent of the present invention is preferably obtained by a method of manufacturing which involves the step of pneumatically transporting the silicon dioxide and the water absorbing resin particles after mixing the silicon dioxide with the water absorbing resin particles.

Another water absorbing agent of the present invention is, in order to solve the problems, characterized in that it contains water absorbing resin particles obtained by polymerization of a water-soluble unsaturated monomer. The agent is further characterized in that it satisfies conditions (A) to (D) below:

(A) the particles are, near a surface thereof, either crosslinked or coated with a surface crosslinking agent which has at least one hydroxyl group;

(B) the particles contain a polyvalent metal salt and water-insoluble inorganic particles at least either on or near the surface;

(C) the water absorbing agent has a mass median particle size of 200 µm to 500 µm inclusive; and (D) the water absorbing agent contains 5 mass % or less particles which have such a size that they can pass through a sieve having a mesh opening size of 150 µm.

The water absorbing agent of the present invention is preferably such that the polyvalent metal salt accounts for 0.01 mass % to 1 mass %, inclusive, of the water absorbing agent.

The water absorbing agent of the present invention is preferably such that the water-insoluble inorganic particles account for 0.001 mass % to 0.4 mass %, inclusive, of the water absorbing agent.

The water absorbing agent of the present invention is preferably such that the water-insoluble inorganic particles are silicon dioxide.

The water absorbing agent of the present invention is preferably such that the water absorbing agent has a centrifuge retention capacity of 30 g/g inclusive to 50 g/g exclusive, and a saline flow conductivity (SFC) of 10 ($10^{-7} \cdot cm^3 \cdot s \cdot g^{-1}$) or more.

The water absorbing agent of the present invention preferably contains dust in such an amount that the dust contains $SiO_2$ which is 50 mass % or less.

A water absorbent core of the present invention is, in order to solve the problems, characterized in that it contains any of the aforementioned water absorbing agents.

A method of manufacturing a water absorbing agent of the present invention is, in order to solve the problems, characterized in that it is a method of manufacturing a water absorbing agent containing water absorbing resin particles obtained by polymerization of a water-soluble unsaturated monomer, the water absorbing resin particles having a mass median particle size of 200 µm to 500 µm inclusive. The method is further characterized in that it involves the sequential steps of: (1) either crosslinking or coating the water absorbing resin particles near a surface thereof with a surface crosslinking agent which has at least one hydroxyl group; and (2) mixing a polyvalent metal salt and water-insoluble inorganic particles with the water absorbing resin particles.

BEST MODE FOR CARRYING OUT INVENTION

Figure 1:
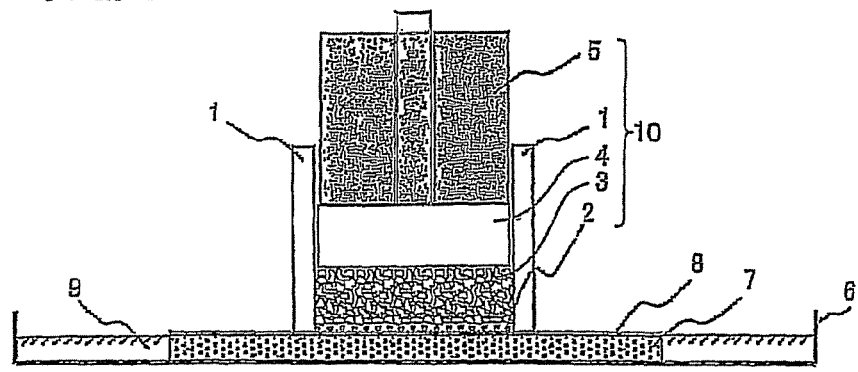
FIG. 1 is a cross-sectional view illustrating an AAP measurement apparatus in relation to the present example.

The following will describe the present invention in detail. The scope of the present invention is however not limited by the description. Apart from the examples given below, the invention may be modified in other ways for implementation without departing from the spirit of the invention. Note that in the present invention, "weight" and "mass" are synonyms of "wt %" and "mass %" respectively. Throughout the specification and claims, only "mass" and "mass %" are used. The numerical expression "A to B" refers to a range of more than or equal to A and less than or equal to B.

Abbreviations which will be used in the following description are defined first. CRC is an acronym of "centrifuge retention capacity." SFC is an acronym of "saline flow conductivity." AAP refers to absorbency against a pressure of 4.83 kPa. FHA is an acronym of "fixed height absorbency." LDV is an acronym of "liquid distribution velocity." D50 refers to a mass median particle size. $\sigma\zeta$ is the logarithmic standard deviation of a particle size distribution. Saline is an aqueous solution of sodium chloride. 1 ppm is equal to 0.0001 mass %.

An embodiment of the present invention is now described. The water absorbing agent of the present embodiment contains water absorbing resin particles. The water absorbing resin particles contain water-insoluble inorganic particles (hereinafter, may be referred to as "water-insoluble inorganic fine particles").

Water Absorbing Resin Particles

The water absorbing resin particles used in the present embodiment are particles of a water-insoluble, water-swelling, hydrogel-forming polymer prepared by polymerization of a water-soluble unsaturated monomer (hereinafter, may also be referred to as a "water absorbing resin").

Concrete examples of the water-insoluble, water-swelling, hydrogel-forming polymer include partially neutralized, crosslinked polyacrylic acid polymers (Specification of U.S. Pat. No. 4,625,001, Specification of U.S. Pat. No. 4,654,039, Specification of U.S. Pat. No. 5,250,640, Specification of U.S. Pat. No. 5,275,773, Specification of European Patent 456136, etc.); a partially neutralized, crosslinked starch-acrylic acid graft polymer (Specification of U.S. Pat. No. 4,076,663); an isobutylene-maleic acid copolymer (Specification of U.S. Pat. No. 4,389,513); a saponification product of a vinyl acetate-acrylic acid copolymer (Specification of U.S. Pat. No. 4,124,748); a hydrolysate of an acrylamide (co)polymer (Specification of U.S. Pat. No. 3,959,569); and a hydrolysate of an acrylonitrile polymer (Specification of U.S. Pat. No. 3,935,099).

The water absorbing resin particles of the present embodiment are preferably particles of a water absorbing resin containing a polyacrylic acid/polyacrylate-based crosslinked polymer obtained by polymerization of a monomer containing an acrylic acid and/or salt thereof. In the present embodiment, the polyacrylic acid/polyacrylate-based crosslinked polymer refers to the crosslinked polymer obtained by polymerization of a monomer containing an acrylic acid and/or salt thereof in at least 50 mol %, preferably at least 70 mol %, more preferably at least 90 mol %.

Acid groups in the crosslinked polymer are neutralized in a ratio preferably from 50 mol % to 90 mol % inclusive, more preferably from 60 mol % to 80 mol % inclusive. The polyacrylate may be, for example, an alkali metal salt, such as sodium, potassium, or lithium; an ammonium salt; or an amine salt. A preferred example is a sodium salt. The salt may be formed in a neutralization before the polymerization, that is, through the neutralization of the monomer, or during or after the polymerization, that is, through the neutralization of the polymer. Alternatively, any of the methods may be used together.

The polyacrylic acid/polyacrylate-based crosslinked polymer that is suited for use as the water absorbing resin particles of the present embodiment may be prepared by copolymerizing another monomer, if necessary, in addition to the primary component monomer (acrylic acid and/or salt thereof). Concrete examples of the other monomer include unsaturated anionic monomers, such as methacrylic acid, maleic acid, vinyl sulfonic acid, styrene sulfonic acid, 2-(meth)acrylamide-2-methylpropanesulfonic acid, 2-(meth)acryloylethanesulfonic acid, and 2-(meth)acryloylpropanesulfonic acid, and salts thereof; non-ionic hydrophilic group-containing unsaturated monomers, such as acrylamide, methacrylicamide, N-ethyl(meth)acrylamide, N-n-propyl(meth)acrylamide, N-isopropyl(meth)acrylamide, N,N-dimethyl(meth)acrylamide, 2-hydroxyethyl(meth)acrylate, 2-hydroxypropyl(meth)acrylate, methoxypolyethylene glycol(meth)acrylate, polyethylene glycol mono(meth)acrylate, vinylpyridine, N-vinylpyrrolidone, N-acryloyl piperidine, N-acryloyl pyrrolidine, and N-vinylacetoamide; and unsaturated cationic monomers, such as N,N-dimethylaminoethyl(meth)acrylate, N,N-diethylaminoethyl(meth)acrylate, N,N-dimethylaminopropyl(meth)acrylate, N,N-dimethylaminopropyl(meth)acrylamide, and quaternary salts thereof. The monomers, other than the acrylic acid and/or salt thereof, may be used in an amount of preferably 0 mol % to 30 mol % inclusive, more preferably 0 mol % to 10 mol % inclusive, to the total amount of the monomers.

The water absorbing resin particles used in the present embodiment are a crosslinked polymer with an internal crosslinking structure. The internal crosslinking structure may be introduced to the water absorbing resin particles, for example, through self-crosslinking using no crosslinking agent or by copolymerizing or reacting an internal crosslinking agent containing two or more unsaturated polymerizing groups and/or two or more reactive groups per molecule of the internal crosslinking agent (the copolymerization or reaction of an internal crosslinking agent is preferred).

Concrete examples of the internal crosslinking agent include polyhydric alcohols, such as N,N'-methylene bis(meth)acrylamide, (poly)ethylene glycol di(meth)acrylate, (poly)propylene glycol di(meth)acrylate, trimethylolpropane tri(meth)acrylate, trimethylolpropane di(meth)acrylate, glycerine tri(meth)acrylate, glycerine acrylate methacrylate, ethylene oxide denatured trimethylolpropane tri(meth)acrylate, pentaerythritol tetra(meth)acrylate, dipentaerythritol hexa(meth)acrylate, triallyl cyanurate, triallyl isocyanurate, triallyl phosphate, triallylamine, poly(meth)allyloxyalkanes, (poly)ethylene glycol diglycidyl ether, glycerol diglycidyl ether, ethylene glycol, polyethylene glycol, 1,4-butanediol, propylene glycol, glycerine, and pentaerythritol; ethylenediamine; polyethyleneimine; and glycidyl(meth)acrylate.

Any one of the internal crosslinking agents may be used alone; alternatively two or more of them may be used. In view of the water absorption property of the obtained water absorbing resin particles and other factors, a preferred internal crosslinking agent must be a compound with two or more unsaturated polymerizing groups. The internal crosslinking agent used accounts preferably for 0.005 mol % to 3 mol % inclusive, more preferably for 0.01 mol % to 1.5 mol % inclusive, most preferably for 0.05 mol % to 0.2 mol % inclusive, of the entire monomer.

In the polymerization, a hydrophilic polymer, such as starch-cellulose, a derivative of starch-cellulose, polyvinyl alcohol, polyacrylic acid (salt), or a crosslinked polymer of polyacrylic acid (salt), or a chain transfer agent such as a hypophosphorous acid (hypophosphite) may be added.

The monomer containing the above-mentioned acrylic acid and/or salt thereof as the primary component(s) can be polymerized by bulk polymerization, reverse suspension polymerization, or precipitation polymerization. Nevertheless, solution polymerization, using the monomer dissolved in water, is preferred in view of performance and ease in controlling the polymerization. These polymerizations are described in, for example, the Specification of U.S. Pat. No. 4,625,001, the Specification of U.S. Pat. No. 4,769,427, the Specification of U.S. Pat. No. 4,873,299, the Specification of U.S. Pat. No. 4,093,776, the Specification of U.S. Pat. No. 4,367,323, the Specification of U.S. Pat. No. 4,446,261, the Specification of U.S. Pat. No. 4,683,274, the Specification of U.S. Pat. No. 4,690,996, the Specification of U.S. Pat. No. 4,721,647, the Specification of U.S. Pat. No. 4,738,867, the Specification of U.S. Pat. No. 4,748,076, and the Specification of U.S. Published Patent Application 2002/40095.

In the polymerization, a radical polymerization initiator, such as potassium persulfate, ammonium persulfate, sodium persulfate, t-butylhydroperoxide, hydrogen peroxide, or 2,2'-azobis(2-amidino propane)dihydrochloride, or an activation energy beam, such as an ultraviolet or electron beam, may be used. In the case of using the radical polymerization initiator, redox polymerization may be carried out by using in a combination with a reduction agent, such as sodium sulfite, sodium hydrogen sulfite, ferrous sulfate, or L-ascorbic acid. The polymerization initiator used accounts preferably for 0.001 mol % to 2 mol % inclusive, more preferably 0.01 mol % to 0.5 mol % inclusive, of the entire monomer.

The polymerized gel, suspended particles, and like materials can be dried using an ordinary drier or heating furnace. Alternatively, the materials may be dried by azeotropic dehydration. The drier may be, for example, a hot air drier, groove stirring drier, rotary drier, disc drier, flow layer drier, air flow drier, or infrared drier.

The materials are dried preferably at 100 to 250° C., more preferably at 150 to 230° C., even more preferably at 160 to 210° C.

Solid content accounts for preferably 50 to 100 mass % (water content: 50 to 0 mass %), more preferably 85 to 100 mass % (water content: 15 to 0 mass %), even more preferably 90 to 98 mass % (water content: 10 to 2 mass %), of the dried product obtained. The solid content rate is usually calculated from a weight loss in a 3-hour drying of a 1-gram sample in an aluminum cup or a glass petri dish at 180° C.

The dried product may be crushed/pulverized using, for example, a vibration mill, roll granulator (see Japanese Unexamined Patent Publication 9-235378/1997 (Tokukaihei 9-235378), paragraph [0174]), knuckle pulverizer, roll mill (see Published Japanese Translation of PCT Application (Tokuhyo) 2002-527547, paragraph [0069]), high speed rotation pulverizer (pin mill, hammer mill, screw mill, roll mill, etc. (see Japanese Unexamined Patent Publication 6-41319/1994 (Tokukaihei 6-41319), paragraph [0036]), or cylindrical mixer (see Japanese Unexamined Patent Publication 5-202199/1993 (Tokukaihei 5-202199), paragraph Using an air flow drier or like machine, the product can be crushed and dried at the same time.

The water absorbing resin obtained by the drying and crushing/pulverization preferably has a predetermined size (a narrow particle size distribution) as a result of, for example, classification before the resin is surface-crosslinked (detailed later). Preferably, the agglomerate of the water absorbing resin particles also has a predetermined size as a result of classification where necessary, like the non-agglomerate water absorbing resin (detailed later).

The shape of the water absorbing resin particles obtained by the polymerization explained above is typically, for instance, irregularly pulverized, spherical, fibrous, virgate, substantially spherical, or flat. It is preferred if the particles have an irregularly pulverized shape because the particles can contain a large amount of silicon dioxide (detailed later) at least either on the surface or near the surface of the particles.

The water absorbing resin particles according to the present embodiment preferably have regions near the surface crosslinked by an organic surface crosslinking agent and/or a water-soluble inorganic surface crosslinking agent. When this is the case, the water absorbing resin contained in the water absorbing agent has regions near the surface crosslinked by a surface crosslinking agent. That reduces the amount of liquid which may seep out when the swollen water absorbing agent is placed under pressure. Absorption under the AAP pressure is thus improved.

Examples of the surface crosslinking agent that can be used in the surface crosslinking include organic surface crosslinking agents and/or water-soluble inorganic surface crosslinking agents with two or more functional groups which can react with the functional groups, especially, carboxyl groups, of the water absorbing resin particles. Water-soluble organic surface crosslinking agents are preferred.

Examples include polyhydric alcohols, such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerine, polyglycerine, 2-butene-1,4-diol, 1,3-butanediol, 1,4-butanediol, 1,5-pentanediol, 1,6-hexanediol, 1,2-cyclohexane dimethanol, 1,2-cyclohexanol, trimethylolpropane, diethanol amine, triethanol amine, polyoxypropylene, oxyethylene-oxypropylene block copolymer, pentaerythritol, and sorbitol; epoxy compounds, such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol; polyvalent amine compounds, such as ethylenediamine, diethylenetriamine, triethylenetetramine, tetraethylenepentamine, pentaethylenehexamine, and polyethyleneimine, and their inorganic and organic salts (for example, azetidinium salts); polyvalent isocyanate compounds, such as 2,4-tolylenediisocyanate and hexamethylenediisocyanate; polyvalent oxazoline compounds, such as 1,2-ethylenebisoxazoline; derivatives of carbonic acids, such as urea, thiourea, guanidine, dicyandiamide, and 2-oxazolidinone; alkylene carbonate compounds, such as 1,3-dioxolane-2-one, 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxy methyl-1,3-dioxolane-2-one, 1,3-dioxane-2-one, 4-methyl-1,3-dioxane-2-one, 4,6-dimethyl-1,3-dioxane-2-one, and 1,3-dioxopane-2-one; haloepoxy compounds, such as epichlorohydrin, epibromohydrin, and α-methylepichlorohydrin, and their polyvalent amine adducts (for example, Kymene (Registered Trademark) manufactured by Hercules Incorporated); silane coupling agents, such as γ-glycidoxypropyl trimethoxysilane and γ-aminopropyl triethoxysilane; and oxetane compounds, such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol, 3-chloromethyl-3-methyl oxetane, 3-chloromethyl-3-ethyl oxetane, and polyvalent oxetane compounds.

Any one of these surface crosslinking agents may be used alone; alternatively two or more of them may be used together. Among them, those surface crosslinking agents which have at least one hydroxyl group are preferred. Especially, polyhydric alcohols are preferred because they are very safe and capable of improving the hydrophilic of the water absorbing resin particle surface.

The surface crosslinking agent used accounts preferably for 0.001 mass parts to 5 mass parts, inclusive, of every 100 mass parts of the solid content of the water absorbing resin particles.

Water may be used in mixing the surface crosslinking agent with the water absorbing resin particles. The water used accounts preferably for 0.5 mass parts, exclusive, to 10 mass parts, inclusive, and more preferably from 1 mass part to 5 mass parts, both inclusive, of every 100 mass parts of the solid content of the water absorbing resin particles.

A hydrophilic organic solvent or a third substance may be used as an auxiliary agent when mixing a surface crosslinking agent or its aqueous solution with the water absorbing resin particles. Examples of such hydrophilic organic solvents include lower alcohols, such as methyl alcohol, ethyl alcohol, n-propyl alcohol, isopropyl alcohol, n-butyl alcohol, isobutyl alcohol, and t-butyl alcohol; ketones, such as acetone; ethers, such as dioxane, tetrahydrofuran, and methoxy(poly)ethylene glycol; amides, such as ε-caprolactam and N,N-dimethyl formamide; sulfoxides, such as dimethyl sulfoxide; and polyhydric alcohols, such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerine, polyglycerine, 2-butene-1,4-diol, 1,3-butanediol, 1,4-butanediol, 1,5-pentanediol, 1,6-hexanediol, 1,2-cyclohexane dimethanol, 1,2-cyclohexanol, trimethylolpropane, diethanol amine, triethanol amine, polyoxypropylene, oxyethylene-oxypropylene block copolymer, pentaerythritol, and sorbitol.

The hydrophilic organic solvent used may account preferably for 10 mass parts or less, more preferably from 0 mass parts to 5 mass parts, inclusive, or from 0.1 mass parts to 5 mass parts, inclusive, of every 100 mass parts of the solid content of the water absorbing resin particles. That amount however may vary depending on the type, particle size, and water content of the water absorbing resin particles, as well as other factors.

The third substance may be, for instance, the inorganic, organic, or polyamino acid described in the Specification of European Patent 0668080. The auxiliary mixed agent may act as a surface crosslinking agent, but preferably should not adversely affect the water absorption capability of the water absorbing resin particles after the surface crosslinking. The water absorbing resin particles of the present embodiment is preferably crosslinked by mixing the particles with a surface crosslinking agent containing no hydrophilic organic solvent of which the boiling point is 100° C. or below and then heating the mixture. If the water absorbing resin particles contain a hydrophilic organic solvent of which the boiling point is 100° C. or below, the hydrophilic organic solvent may vaporize, changing the environment in which the surface crosslinking agent resides on the surface of the water absorbing resin particles. One may not achieve sufficient SFC or other physical properties.

When the surface crosslinking agent is mixed with the water absorbing resin particles, preferably, a water-soluble inorganic salt (preferably a persulfate) is also present to obtain a more uniform mixture of the water absorbing resin particles and the surface crosslinking agent. The water-soluble inorganic salt used accounts preferably for 0.01 mass parts to 1 mass part, inclusive, more preferably 0.05 mass parts to 0.5 mass parts, inclusive, of every 100 mass parts of the solid content of the water absorbing resin particles. That amount however may vary depending on the type and particle size of the water absorbing resin particles, as well as other factors. In other words, the water absorbing resin particles of the present embodiment are preferably crosslinked by mixing the particles with an organic surface crosslinking agent and/or a water-soluble inorganic surface crosslinking agent containing a water-soluble inorganic salt (preferably a persulfate) in a ratio of 0.01 mass % to 1.0 mass %, inclusive to the water absorbing resin particles and then heating the mixture.

The method for mixing the surface crosslinking agent with the water absorbing resin particles is not limited in any particular manner. For example, the water absorbing resin particles may be immersed in a hydrophilic organic solvent and mixed with a surface crosslinking agent dissolved, as necessary, in water and/or a hydrophilic organic solvent. Another mixing method example may be to directly spray or add dropwise to the water absorbing resin particles a surface crosslinking agent dissolved in water and/or a hydrophilic organic solvent.

After mixing the surface crosslinking agent with the water absorbing resin particles, heat is usually and preferably applied so that the crosslink reaction can proceed. The heat treatment temperature, although variable depending on the surface crosslinking agent being used, is preferably from 40° C. to 250° C. inclusive, and more preferably from 150° C. to 250° C. inclusive. If the heat treatment temperature is lower than 40° C., the AAP, SFC, and other absorption properties may not be sufficiently improved. If the heat treatment temperature is higher than 250° C., the excess heat may degrade the water absorbing resin particles and hence various physical properties; care should be taken. The heat treatment time is preferably from 1 minute to 2 hours inclusive, and more preferably from 5 minutes to 1 hour inclusive.

The water absorbing resin particles used in the present embodiment have a mass median particle size of, preferably, 200 μm to 500 μm inclusive, and more preferably 300 μm to 400 μm inclusive. If the water absorbing resin particles have a mass median particle size out of the 200 to 500 μm range, the liquid permeability and diffusibility may fall noticeably, or the absorption rate may fall by a large value. Those water absorbing resin particles, if used in a diaper for example, may be leaky or otherwise defective.

Of the water absorbing resin particles of the present embodiment, preferably 5 mass % or less particles can pass through a sieve of 150-μm mesh, and more preferably 3 mass % or less particles can do so. The use of water absorbing resin particles in these ranges for the water absorbing agent limits the amount of dust in the resulting water absorbing agent. Thus, the fine particles in the water absorbing resin particles will not fly off into the air, unlikely to raise safety/hygiene issues, during manufacture of the water absorbing agent. Also, the physical properties of the resultant water absorbing agent will not likely be degraded. If the ratio is in excess of 5 mass %, dust can occur during manufacture of the water absorbing agent, possibly raising safety/hygiene issues or degrading the physical properties of the water absorbent core, to name a few problems.

The water absorbing resin particles may be fine-powder-like water absorbing resin particles of which the mass median particle size is 300 μm or less (hereinafter, referred to as "fine powder" where appropriate) which have been agglomerated, dried, adjusted in particle size, and surface crosslinked. Alternatively, the water absorbing resin particles may be irregularly pulverized primary particles obtained from pulverization which have been partially mixed with an agglomerate of the fine powder. When an agglomerate of the fine powder is partially mixed with the water absorbing resin particles, the resultant water absorbing agent has its absorption properties, such as water absorption rate and FHA, further improved. The amount of the agglomerate of the fine powder mixed with the water absorbing resin particles is preferably 5 mass % or more, more preferably 10 mass % or more, further preferably, 15 mass % or more, most preferably 20 mass % or more. The particle size of fine powder is defined in terms of the mesh diameters of sieves used in classification.

The agglomerate of the fine powder can be fabricated by any publicly known fine powder reproducing technology. For example, the fine powder may be mixed with warm water and dried (Specification of U.S. Pat. No. 6,228,930). The fine powder may be mixed with an aqueous solution of a monomer and polymerized (Specification of U.S. Pat. No. 5,264,495). Water may be added to the fine powder, and the mixture subjected to agglomeration under surface pressure more than a specific value (Specification of European Patent 844270). The fine powder may be rendered sufficiently humid to form amorphous gel which is subsequently dried and pulverized (Specification of U.S. Pat. No. 4,950,692). The fine powder may be mixed with a polymerized gel (Specification of U.S. Pat. No. 5,478,879).

Preferably, the fine powder is mixed with warm water and dried as in one of the methods briefly described above. The water absorbing resin particles agglomerated by the method have a porous structure (equivalent to the porous structure described in Japanese Unexamined Patent Publication (Tokukai) 2004-261797) and is suited for use. The water absorbing resin particles of the present embodiment contain preferably 5 mass % or more particles with the porous structure, more preferably 10 mass % or more, further preferably 15 mass % or more, most preferably 20 mass % or more. The inclusion of an agglomerate of fine powder with the porous structure in the water absorbing resin particles allows the water absorbing resin particles to efficiently contain silicon dioxide or other water-insoluble inorganic particles at least either on the surface or near the surface (detailed later).

The CRC of the water absorbing resin particles of the present embodiment is preferably 5 g/g or more, more preferably 10 g/g or more, further preferably 15 g/g or more, even more preferably 25 g/g or more, still preferably 28 g/g or more, most preferably 30 g/g or more. The maximum value of the CRC, although not being limited in any particular manner, is preferably 50 g/g or less, more preferably 45 g/g or less, further preferably 40 g/g or less. If the CRC is less than 10 g/g, and the water absorbing resin particles are used for the water absorbing agent, the agent can absorb a very small amount. The agent is not suitable for use in diaper and other sanitary/hygienic materials. On the other hand, if the CRC is more than 50 g/g, and the water absorbing resin particles are used in the water absorbent core, the resultant water absorbing agent may fail to provide a water absorbent core with excellent liquid suction rate per unit time.

The AAP of the water absorbing resin particles of the present embodiment is preferably 16 g/g or more, more preferably 17 g/g or more, even more preferably 18 g/g or more, still more preferably 19 g/g or more, yet more preferably 20 g/g or more, again more preferably 22 g/g or more, and most preferably 24 g/g or more. The maximum value of the AAP, although not being limited in any particular manner, is preferably 30 g/g or less. If the AAP is less than 16 g/g, and the water absorbing resin particles are used for the water absorbing agent, the resultant water absorbing agent may fail to achieve a low level of liquid seeping, or "rewetting," when the water absorbent agent is placed under pressure.

The SFC of the water absorbing resin particles of the present embodiment is preferably 10 ($10^{-7} \cdot cm^3 \cdot s \cdot g^{-1}$) or more, more preferably 15 ($10^{-7} \cdot cm^3 \cdot s \cdot g^{-1}$) or more, further preferably ($10^{-7} \cdot cm^3 \cdot s \cdot g^{-1}$) or more, even more preferably 50 ($10^{-7} \cdot cm^3 \cdot s \cdot g^{-1}$) or more, still more preferably 70 ($10^{-7} \cdot cm^3 \cdot s \cdot g^{-1}$) or more, and yet most preferably 100 ($10^{-7} \cdot cm^3 \cdot s \cdot g^{-1}$) or more. If the SFC is less than 10 ($10^{-7} \cdot cm^3 \cdot s \cdot g^{-1}$), even when the particles contain silicon dioxide or other water-insoluble inorganic particles (detailed later), liquid permeability may not improve. Also, the resultant water absorbing agent may fail to provide a water absorbent core with excellent liquid suction rate per unit time when the water absorbing resin particles are used for the water absorbing agent.

The water-extractable polymer content of the water absorbing resin particles of the present embodiment is preferably 35 mass % or less, more preferably 25 mass % or less, and further preferably 15 mass % or less. If the water-extractable polymer content exceeds 35 mass %, the particles show poor gel strength and liquid permeability. If the water absorbing resin particles are used in the water absorbent core, the resultant water absorbing agent may fail to achieve a low level of liquid seeping, or "rewetting," when the water absorbent core is placed under pressure.

Water-Insoluble Inorganic Particles

The water absorbing resin particles of the present embodiment contains water-insoluble inorganic particles at least either on the surface or near the surface. The "surface" of a water absorbing resin particle refers to those portions which are exposed to air. The term "near the surface" of the water absorbing resin particle refers to those portions between the surface of the particle and a depth about one tenth of the particle size (smaller size). Specifically, the term "near the surface" of the water absorbing resin particle refers to those portions near a surface-crosslinked layer in the case of a surface-crosslinked water absorbing resin particle. The thickness of the layer can be confirmed with, for example, a scanning electron microscope (SEM).

The provision of the water-insoluble inorganic particles at least either on the surface or near the surface of the water absorbing resin particles results in improvement in the liquid permeability of the water absorbing agent. Therefore, the SFC of the water absorbing agent containing the water absorbing resin particles is improved. It would be sufficient for the purpose of liquid permeability improvement if the water-insoluble inorganic particles reside at least either on the surface or near the surface of the water absorbing resin particles. Physical properties of the water absorbing agent are better improved if the particles reside on the surface than near the surface. In the examples detailed later, the water-insoluble inorganic particles reside at least on the surface. Also, the ratio of the water-insoluble inorganic particles residing on the surface is increased by adding the water-insoluble inorganic particles after polymerization.

The water-insoluble inorganic particles used in the present embodiment preferably contain, at least on the surface, functional groups capable of forming ionic bonds with functional groups on the surface of the water absorbing resin particles. The functional groups capable of forming ionic bonds are more preferably cationic groups, even more preferably amino groups (inclusive quaternary amino groups).

In a preferable form of the water absorbing agent, the functional groups residing on the surface of the water absorbing resin particles are carboxyl groups, and the functional groups residing at least on the surface of the water-insoluble inorganic particles are amino groups.

Concrete examples of the water-insoluble inorganic particles which can be used in the present embodiment include mineral produces, such as talc, clay, kaoline, fuller's earth, bentonite, activated clay, barite, natural asphaltum, strontium ore, ilmenite, and pearlite; metal oxides, such as silicon dioxide and titanium oxide; silicic acids (salts), such as natural zeolite and synthetic zeolite; water-insoluble polyvalent metal salts, such as calcium sulfate and aluminum oxide; hydrophilic amorphous silica (ex. Dry Method: ReolosilQS-20 from Tokuyama Corporation. Precipitation Method: Sipernat 22S, Sipernat 2200 from Degussa AG); composite, water-containing hydrated oxides containing either zinc and silicon and or zinc and aluminum (see International Application Published under PCT WO2005/010102 for examples); and oxide complexes, such as silicon oxide/aluminum oxide/magnesium oxide complexes (ex. Attagel #50 from ENGELHARD), silicon oxide/aluminum oxide complexes, and silicon oxide/magnesium oxide complexes. The water-insoluble inorganic particles disclosed also in U.S. Pat. No. 5,164,459 and European Patent 761241 may also be used. Preferred among these examples are silicon dioxide and silicic acid (salt). Especially preferred are silicon dioxide and silicic acid (salt) in fine particle form of which the mean particle size is from 0.001 to 200 μm as measured by a Coulter counter method.

Some concrete examples of the water-insoluble inorganic particles most preferably used in the present embodiment are HDK (Registered Trademark) H2015EP, H2050EP, H2150VP, H05TA, H13TA, and H30TA, from Wacker which are amorphous silica with amino groups (inclusive quaternary amino groups) introduced to its surface. RA200HS from Nippon Aerosil Co., Ltd. may also be used.

The water-insoluble inorganic particles used in the present embodiment preferably have a pH of 7 to 10 when the particles are dispersed in a water-methanol solution (1:1 in volume ratio) in the amount of 4 mass %.

The water-insoluble inorganic particles used in the present embodiment preferably have a mass median particle size of 5 to 50 nm in primary particle form and are such that 90 mass % or more of the particles are aggregate particles of primary particles. The aggregate particles of primary particles preferably have a mass median particle size of 20 μm or less.

The water-insoluble inorganic particles used in the present embodiment preferably have 20% or less of residual silanol groups on the surface (the silanol groups on the surface account for 2 $SiOH/nm^2$ of the whole silanol groups).

The water-insoluble inorganic particles used in the present embodiment preferably has a specific surface area of 30 to 330 $m^2/g$ as measured by BET.

Silicon Dioxide

As mentioned earlier, in the present embodiment, the water-insoluble inorganic particles preferably contain silicon dioxide.

The provision of silicon dioxide at least either on the surface or near the surface of the water absorbing resin particles results in improvement in the liquid permeability of the water absorbing agent. Therefore, the SFC of the water absorbing agent containing the water absorbing resin particles is improved. It would be sufficient for the purpose of liquid permeability improvement if the silicon dioxide resides at least either on the surface or near the surface of the water absorbing resin particles. Physical properties of the water absorbing agent are better improved if the silicon dioxide resides on the surface than near the surface.

The silicon dioxide is preferably amorphous fumed silica manufactured by a dry method. "Quartz" and like silicon dioxides are not desirable due to health risks they may pose. The silicon dioxide preferably does not undergo self-induced aggregation and contains a high concentration of residual silanol groups. Self-induced aggregation of the silicon dioxide is the cause of increase in the amount of dust produced from the water absorbing agent. The present embodiment uses the silicon dioxide in a particular range of amount, and the silicon dioxide contains residual silanol groups in a particular range of concentration, to prevent self-induced aggregation of the silicon dioxide and thereby prevent increase in the amount of dust produced from the water absorbing agent.

The concentration of residual silanol groups on the surface of the silicon dioxide is given in terms of the number of silanol groups in one square nanometer ($nm^2$). In the present invention, a unit "$SiOH/nm^2$" is used. One can consult a catalogue or like documents available from silica manufacturers to find out the residual silanol group concentration. Alternatively, it can be measured by a publicly known methods (ex. a lithium aluminum hydride method).

In the present embodiment, the residual silanol group concentration on the surface of the silicon dioxide is preferably 1.7 $SiOH/nm^2$ or lower. At such low residual silanol group densities, the silicon dioxide is modified at the surface and thus hydrophobic. If the concentration exceeds 1.7 $SiOH/nm^2$, the silicon dioxide is likely to aggregate and thus produce dust, which is undesirable. The surface modification of the silicon dioxide hinders the silanol groups from forming hydrogen bonds between them, and hence the silicon dioxide in fine particle form from aggregating. The silicon dioxide content is as low as from 10 ppm to 1,900 ppm inclusive to the water absorbing resin particles. With such low non-aggregated silicon dioxide content, its fine particles are adsorbed by interparticle bonding force, such as electrostatic force and van der Waals force, to the water absorbing resin particles. Therefore, the amount of dust produced because of the provision of the silicon dioxide in the water absorbing resin particles is limited.

If the silicon dioxide of which the residual silanol group concentration exceeds 1.7 $SiOH/nm^2$ is used, there reside many silanol groups on the surface of the silicon dioxide; silanol groups form hydrogen bonds between them, and the fine particles of the silicon dioxide aggregate. The aggregated fine particles are not well adsorbed by the water absorbing resin particles and come off easily. The fine particles thus fly away forming dust. It is difficult to limit the amount of dust.

The concentration of the residual silanol groups on the surface of the silicon dioxide is preferably 1.7 $SiOH/nm^2$ or lower, more preferably from 0.7 $SiOH/nm^2$ to 1.7 $SiOH/nm^2$ inclusive, further preferably from 0.9 $SiOH/nm^2$ to 1.7 $SiOH/nm^2$. If the concentration is lower than 0.7 $SiOH/nm^2$, the silicon dioxide becomes more hydrophobic, and LDV falls, which is not desirable.

Concrete examples of the silicon dioxide contained in the water absorbing resin particles include HDK (Registered Trademark) H15 ($\approx$0.96 $SiOH/nm^2$), H20 ($\approx$1.00 $SiOH/nm^2$), H30 ($\approx$1.08 $SiOH/nm^2$), H1303VP ($\approx$0.36 $SiOH/nm^2$), H2000/4 ($\approx$0.60 $SiOH/nm^2$), H2000T ($\approx$0.36 $SiOH/nm^2$), and H3004 ($\approx$0.40 $SiOH/nm^2$), all available from Wacker. Examples of the silicon dioxide include H05TD, H13TD, H20TD, H30TD, H05TM, H13TM, H20TM, H30TM, H05TX, H13TX, H20TX, and H30TX, all having a residual silanol group concentration of about 0.40 $SiOH/nm^2$ or lower. Other examples include Aerosil (Registered Trademark) R-972 ($\approx$0.60 $SiOH/nm^2$), R-974 ($\approx$0.39 $SiOH/nm^2$), R805 ($\approx$1.66 $SiOH/nm^2$), R812 ($\approx$0.44 $SiOH/nm^2$), R812S ($\approx$0.68 $SiOH/nm^2$), and R202 ($\approx$0.29 $SiOH/nm^2$), all manufactured by Nippon Aerosil Co., Ltd., Reolosil (Registered Trademark) MT-10 (C), DM-10 (C), DM-30, DM-30S, KS-20SC, HM-20L, HM-30S, and PM-20 (L), all manufactured by Tokuyama Corporation.

Water Absorbing Agent

The water absorbing agent of the present embodiment contains water absorbing resin particles with an internal crosslinking structure obtained by polymerization of a water-soluble unsaturated monomer. The agent satisfies conditions (a) to (d) below:

(a) the agent contains water-insoluble inorganic particles at an amount of from 10 ppm to 1,900 ppm inclusive;

(b) the agent contains 5 mass % or less particles which have such a size that they can pass through a sieve having a mesh opening size of 150 μm;

(c) the agent has an absorbency against a pressure of 4.83 kPa (AAP) of 18 g/g or more; and (d) the water-insoluble inorganic particles reside on the surface of the water absorbing resin or near the surface.

The water absorbing agent of the present embodiment contains water-insoluble inorganic particles at an amount of from 10 ppm to 1,900 ppm inclusive, more preferably 10 to 1,500 ppm, most preferably 10 to 990 ppm, relative to the water absorbing agent. If there are contained too many water-insoluble inorganic particles, safety/health concerns may arise due to fine particles flying away during the manufacture of the absorbent core, and the performance of the absorbent core be degraded. If too many water-insoluble inorganic particles are used for the absorbent core, the resultant water absorbing agent may be such that the absorbent core does not show sufficient vertical liquid suction capability (i.e., fixed height absorbency (FHA)).

In the water absorbing agent of the present embodiment, the silicon dioxide detailed above (with a residual silanol group concentration of 1.7 $SiOH/nm^2$ or lower on the surface) may be replaced with silicon dioxide which has yet to undergo self-induced aggregation or of which the self-induced aggregation has been broken by, for example, mechanical force. The use of the silicon dioxide with a residual silanol group concentration of 1.7 $SiOH/nm^2$ or lower is merely one of means of limiting self-induced aggregation of the silicon dioxide. Whether the silicon dioxide in the water absorbing resin particles has or has not undergone self-induced aggregation can be determined by analyzing fine particles filtered out after the measurement of dust amount (detailed later). For example, the filtered-out fine particles are observed under a scanning electron microscope or an X-ray microanalyzer; if silicon dioxide particles with major diameters of 20 μm to 100 μm, inclusive, are found among the fine particles, and the ratio of the number of those silicon dioxide particles to the number of filtered-out fine particles with major diameters of 20 μm to 100 μm, inclusive, is 10% or higher, the silicon dioxide is determined to have undergone self-induced aggregation.

In other words, the water absorbing agent of the present embodiment contains water absorbing resin particles with an internal crosslinking structure obtained by polymerization of a water-soluble unsaturated monomer. In the agent, the water absorbing resin particles are crosslinked by a surface crosslinking agent near the surface and contain silicon dioxide at least either on the surface or near the surface. Furthermore, of the fine particles with major diameters of 20 μm to 100 μm, inclusive, filtered out after the measurement of dust amount in the water absorbing agent, 10% or less is accounted for by silicon dioxide. Besides, the silicon dioxide content of the water absorbing agent is 10 ppm to 1,900 ppm inclusive. The mass median particle size of the water absorbing agent is from 200 μm to 500 μm inclusive. Particles which pass through a sieve having a mesh opening size of 150 μm constitute 5 mass % or less of the mass of the entire water absorbing agent.

The water absorbing agent of the present embodiment preferably contains at least 0.001 mass % to 5 mass % inclusive, more preferably 0.01 mass % to 1 mass % inclusive, polyvalent metal salt. The abundant provision of polyvalent metal salt in the water absorbing agent (preferably trivalent water-soluble polyvalent metal salt) improves saline flow conductivity while substantially preserving the absorbency under 4.83 kPa load and fixed height absorbency of the water absorbing agent. The provision also makes up for the lack of the silicon dioxide or other water-insoluble inorganic particles at least either on the surface or near the surface of the water absorbing agent where there is no silicon dioxide or other water-insoluble inorganic particles. The obtained water absorbing agent has more excellent physical properties because of the synergistic effects of the silicon dioxide or other water-insoluble inorganic particles and the polyvalent metal salt.

Concrete examples of the polyvalent metal salt that can be used in the present embodiment include sulfates, nitrates, carbonates, phosphates, organic acid salts, and halides (ex. chlorides) of Zn, Be, Mg, Ca, Sr, Al, Fe, Mn, Ti, Zr, Ce, Ru, Y, Cr, and like metals. Another example is the polyvalent metal salt described in Japanese Unexamined Patent Publication (Tokukai) 2005-113117.

Most preferred of the polyvalent metal salt are trivalent water-soluble metal salts. Concrete examples of trivalent water-soluble polyvalent metal salts include aluminum chloride, aluminum polychloride, aluminum sulfate, aluminum nitrate, aluminum potassium sulfate, aluminum sodium sulfate, potassium alum, ammonium alum, sodium alum, sodium aluminate, iron(III) chloride, cerium(III) chloride, ruthenium(III) chloride, yttrium(III) chloride, and chromium(III) chloride.

It is preferable to use these salts which contain crystal water also in view of the solubility of urine and other liquids absorbed. Especially preferred among them are aluminum compounds, especially, aluminum chloride, aluminum polychloride, aluminum sulfate, aluminum nitrate, aluminum potassium sulfate, aluminum sodium sulfate, potassium alum, ammonium alum, sodium alum, and sodium aluminate. Aluminum sulfate is particularly preferred. The most preferred is an aqueous solution of aluminum sulfate (desirably, a solution of aluminum sulfate with a 90% or higher concentration as based on saturation). Any one of these compounds may be used alone; alternatively two or more of them may be used together. One of the most preferred forms of the water absorbing agent of the present embodiment is the water absorbing agent that contains silicon dioxide and a trivalent water-soluble polyvalent metal salt.

The water absorbing agent of the present embodiment produces little dust. Dust, if present at all, is preferably 400 ppm or less, more preferably 355 ppm or less, further preferably 300 ppm or less, still more preferably 240 ppm or less, as measured with a Heubach Dustmeter (detailed later). So long as one of these conditions is met, silicon dioxide or other water-insoluble inorganic particles, if contained in the water absorbing agent, will not spread into the air, unlikely to raise safety/hygiene issues, during manufacture of the water absorbing agent. Also, the physical properties of the water absorbent core will not likely be degraded.

The water absorbing agent has a mass median particle size of, preferably, 200 μm to 500 μm, inclusive, more preferably 300 μm to 400 μm, inclusive. If the mass median particle size is out of this 200 μm to 500 μm range, the liquid permeability may fall, and the liquid suction rate per unit time of the water absorbing agent may fall noticeably. In other words, the absorption rate may fall by a large value, and that absorbing agent, if used in a diaper for example, may be leaky or otherwise defective.

Particles that can pass through a sieve of 150-μm mesh preferably constitute 5 mass % or less of the water absorbing agent. The ratio is more preferably 4 mass % or less, and further preferably 3 mass % or less. If the ratio is in excess of mass %, even when the silicon dioxide or other water-insoluble inorganic particles of the present embodiment are contained, particles can fly away during manufacture of the water absorbing agent, possibly raising safety/hygiene issues or degrading the physical properties of the water absorbent core obtained.

The particle size distribution of the water absorbing agent has a logarithmic standard deviation ($\sigma\zeta$) of preferably 0.20 to 0.50, inclusive, more preferably 0.20 to 0.40, inclusive, and even more preferably 0.30 to 0.40, inclusive. If the standard deviation is out of these ranges, the liquid permeability may so decrease that the water absorbent core has a very poor liquid suction rate per unit time.

The water absorbing agent has a CRC of preferably 5 g/g or more, more preferably 10 g/g or more, even more preferably 15 g/g or more, still more preferably 25 g/g or more, and yet preferably 28 g/g or more.

The maximum CRC, although not limited in any particular manner, is preferably 50 g/g or less, more preferably 45 g/g less, and even more preferably 40 g/g or less. If the CRC is less than 5 g/g, the water absorbing agent absorbs too small an amount of liquid to be used as diapers and other sanitary/hygienic materials. If the centrifuge retention capacity (CRC) is more than 50 g/g, and the obtained water absorbing agent is used in the water absorbent core, the core may not exhibit an excellent liquid suction rate per unit time into the water absorbent core.

The water absorbing agent of the present embodiment has a SFC of preferably 10 ($10^{-7}\cdot cm^3\cdot s\cdot g^{-1}$) or more, more preferably 15 ($10^{-7}\cdot cm^3\cdot s\cdot g^{-1}$) or more, even more preferably 30 ($10^{-7}\cdot cm^3\cdot s\cdot g^{-1}$) or more, still more preferably 50 ($10^{-7}\cdot cm^3\cdot s\cdot g^{-1}$) or more, yet more preferably 70 ($10^{-7}\cdot cm^3\cdot s\cdot g^{-1}$) or more, most preferably 100 ($10^{-7}\cdot cm^3\cdot s\cdot g^{-1}$) or more. If the SFC is less than 10 ($10^{-7}\cdot cm^3\cdot s\cdot g^{-1}$), even when the silicon dioxide or other water-insoluble inorganic particles are added, the liquid permeability does not improve. The water absorbing agent obtained, when used in the water absorbent core, does not exhibit an excellent liquid suction rate per unit time to the water absorbent core. The maximum SFC, although not limited in any particular manner, is preferably 2,000 ($10^{-7}\cdot cm^3\cdot s\cdot g^{-1}$) or less.

The water absorbing agent of the present embodiment preferably has well-balanced CRC and SFC. Specifically, if the CRC is 5 g/g or more and less than 25 g/g, the SFC is preferably 100 ($10^{-7}\cdot cm^3\cdot s\cdot g^{-1}$) or more, more preferably 150 ($10^{-7}\cdot cm^3\cdot s\cdot g^{-1}$) or more, and even most preferably 300 ($10^{-7}\cdot cm^3\cdot s\cdot g^{-1}$) or more. If the CRC is 25 g/g or more and less than 30 g/g, the SFC is preferably 30 ($10^{-7}\cdot cm^3\cdot s\cdot g^{-1}$) or more, more preferably 70 ($10^{-7}\cdot cm^3\cdot s\cdot g^{-1}$) or more, most preferably 100 ($10^{-7}\cdot cm^3\cdot s\cdot g^{-1}$) or more. If the CRC is from 30 g/g inclusive to 50 g/g exclusive, the SFC is preferably 10 ($10^{-7}\cdot cm^3\cdot s\cdot g^{-1}$) or more, more preferably 15 ($10^{-7}\cdot cm^3\cdot s\cdot g^{-1}$) or more, even more preferably 30 ($10^{-7}\cdot cm^3\cdot s\cdot g^{-1}$) or more, most preferably 50 ($10^{-7}\cdot cm^3\cdot s\cdot g^{-1}$).

If the CRC and SFC are within one of these ranges, the water absorbing agent, when used in the water absorbent core, shows a sufficiently high absorption which makes up for possibly liquid permeability. On the other hand, if the liquid permeability is high, liquid diffuses in the water absorbing agent, enabling absorption across a wide area, even when the agent absorbs a small amount of liquid. Thus, the resulting water absorbing agent exhibits an excellent liquid suction rate per unit time when used in the water absorbent core.

The water absorbing agent has an absorbency against a pressure of 4.83 kPa (AAP) of 18 g/g or more. The value is more preferably 20 g/g or more, even more preferably 22 g/g or more, and most preferably 24 g/g or more. The maximum AAP, although not limited in any particular manner, is preferably 30 g/g or lower. If the absorbency against a pressure of 4.83 kPa (AAP) is lower than 18 g/g, the water absorbing agent, when used in the water absorbent core, may cause lot of liquid seeping, or "rewetting," when the water absorbent core is placed under pressure.

Of the entire water absorbing agent, those particles of which the particle sizes are from 150 to 850 μm are preferably 90 mass % or more. More preferably, those particles of which the particle sizes are from 150 to 600 μm are 90 mass % or more.

The water-extractable polymer content of the water absorbing agent is preferably 35 mass % or less, more preferably 25 mass % or less, even more preferably 15 mass % or less. If the water-extractable polymer content of the water absorbing agent exceeds 35 mass %, the gel shows poor strength and liquid permeability. Besides, if the water absorbing agent is used in a diaper over an extended period of time, the CRC, AAP, etc. may be degraded over time.

The water absorbing agent is preferably charged negative after experiencing frictional motion. That prevents aggregation of the silicon dioxide and the water absorbing agent and restrains the silicon dioxide from coming off the water absorbing resin particles. As a result, the amount of dust of the water absorbing agent is decreased.

The water absorbing agent has a liquid distribution velocity of preferably 0.2 mm/sec to 10.0 mm/sec inclusive, more preferably 0.5 mm/sec to 10.0 mm/sec inclusive, even more preferably 0.8 mm/sec to 10.0 mm/sec inclusive.

Accordingly, the liquid absorbed by the water absorbing agent diffuses efficiently. That improves the liquid suction rate per unit time of the water absorbent core and liquid diffusibility in the water absorbent core. Thus, water absorption capability is improved.

A plant component A1, chelate agent B1, other substance C1, etc. (detailed later) may be added as in a very small amount to the water absorbing agent to impart the particulate water absorbing agent with various functions.

The amount of the additives A1 to C1 used may vary depending on objects and additional functions. Generally, one of such additives may be added in 0 to 10 mass parts, preferably 0.001 to 5 mass parts, more preferably 0.002 to 3 mass parts, to 100 mass parts of the water absorbing resin. Generally, if the amount is less than 0.001 mass parts, sufficient effects or addition functions are not achieved. If the amount is 10 mass parts or more, effects cannot be achieved in proportion to the amount added, or the absorbency may fall.

Plant Component A1

The particulate water absorbing agent of the present embodiment may be blended with a plant component so that the agent can be deodorizing. The preferred ratio of the plant component blended is as mentioned above. Plant components that may be used in the present embodiment are preferably a powder of a plant itself or an extract of the plant. The compound(s) in the plant component is/are preferably either at least one compound selected from polyphenol, flavone and like substances, and caffeine or at least one compound selected from tannin, tannic acid, galla, gallnut, and gallic acid. Examples are found in U.S. Pat. No. 6,469,080, European Patent 1352927, and International Application Published under PCT WO2003/104349, as examples. Examples of the form in which the plant component is blended in the present invention include essence (essential oil, etc.) extracted from the plant, a plant per se (plant powder, etc.), plant refuse and extraction refuse which are byproducts of manufacturing processes in the plant processing industry and the food processing industry.

The particle size of powder when the plant component A1 is provided in powder form and/or the particle size of powder which carries essence (essential oil) containing the plant component A1 extracted from a plant is generally from 0.001 to 1,000 μm, preferably from 1 to 600 μm. The mass median particle size of the particles containing a plant component is preferably 500 μm or less, more preferably 300 μm or less. If the mass median particle size is more than 500 μm, the effective component in the plant component, when coming into contact with urine, does not work sufficiently, possibly failing to achieve stable deodorizing capability. The mass median particle size is preferably smaller than the mass median particle size of the water absorbing resin to achieve excellent deodorizing capability and stability. Examples of particles containing a plant component include a plant powder into which a plant per se has been made into and a particulate carrier carrying a plant component. Examples of such a carrier include those carrying essence (essential oil) containing a plant component extracted from a plant. The plant component usable in the present embodiment preferably takes the form of liquid and/or aqueous solution at normal temperature so that the plant component can be readily added to the water absorbing resin.

Addition of Chelate Agent B1

A chelate agent, especially a polyvalent carboxyl acid and its salt, is preferably blended to obtain the particulate water absorbing agent of the present embodiment.

The chelate agent that can be used for the particulate water absorbing agent of the present embodiment is preferably a chelate agent with a high Fe or Cu sequestering or chelating capability: namely, a chelate agent with a stability constant with respect to Fe ions of 10 or more, preferably 20 or more, more preferably an amino polyvalent carboxyl acid and its salt, even more preferably an amino carboxyl acid with three or more carboxyl groups and its salt.

The polyvalent carboxyl acids are, specifically, diethylenetriaminepentaacetic acid, triethylenetetraaminehexaacetic acid, cyclohexane-1,2-diaminetetraacetic acid, N-hydroxyethyl ethylenediaminetriacetic acid, ethylene glycol diethyl ether diaminetetraacetic acid, ethylenediamine tetrapropionic acetic acid, N-alkyl-N'-carboxy methyl aspartic acid, N-alkenyl-N'-carboxy methyl aspartic acid, and their alkali metal salts, alkali earth metal salts, ammonium salts, and amine salts. The most preferred among them are diethylenetriaminepentaacetic acid, triethylenetetraaminehexaacetic acid, N-hydroxyethyl ethylenediaminetriacetic acid, and their salts.

Other Substances C1

Various additives, such as an antibacterial agent, a water-soluble polymer, a water-insoluble polymer, water, a surfactant, organic fine particles, may or may not be added provided that the particulate water absorbing agent of the present embodiment is obtainable.

The water absorbing agent of the present embodiment contains water absorbing resin particles which may or may not contain a polyvalent metal salt and water-insoluble inorganic particles. Specifically, the water absorbing agent of the present embodiment may contain water absorbing resin particles obtained by polymerization of a water-soluble unsaturated monomer. The agent satisfies conditions (A) to (D) below:

(A) the particles are, near the surface, either crosslinked or coated with a surface crosslinking agent which has at least one hydroxyl group;

(B) the particles contain a polyvalent metal salt and water-insoluble inorganic particles at least either on the surface or near the surface;

(C) the water absorbing agent has a mass median particle size of 200 μm to 500 μm inclusive; and (D) the water absorbing agent contains 5 mass % or less particles which have such a size that they can pass through a sieve having a mesh opening size of 150 µm.

The water absorbing resin particles in the water absorbing agent is either crosslinked or coated near the surface with a surface crosslinking agent which has at least one hydroxyl group. The water absorbing resin contained in the water absorbing agent is either crosslinked or coated near the surface with a surface crosslinking agent which has at least one hydroxyl group as stated above. That reduces the amount of liquid which may seep out when the swollen water absorbing agent is placed under pressure. Therefore, the absorbency against pressure, or AAP, is increased.

The water absorbing agent is not limited by any particular means except the condition that the water absorbing agent contains water absorbing resin particles obtained by polymerization of a water-soluble unsaturated monomer and items (A) to (D). For example, the water absorbing agent may be conditioned within the aforementioned ranges described in relation to the water absorbing agent meeting conditions (a) to (d). Also, conditions (A) to (D) may be narrowed down to the ranges described in relation to the water absorbing agent meeting conditions (a) to (d), to impart excellent physical properties to the water absorbing agent.

The water absorbing agent that meets conditions (A) to (D) preferably contains water-insoluble inorganic particles. The ratio of the particles to the water absorbing agent is preferably from 0.001 mass % to 5 mass % inclusive, more preferably from 0.01 mass % to 3 mass % inclusive, even more preferably from 0.01 mass % to 1 mass % inclusive, still more preferably from 0.01 mass % to 0.4 mass % inclusive, most preferably from 0.05 mass % to 0.4 mass % inclusive. The upper and lower limits of the numeric range may be combined appropriately. A preferred numeric value range, as an example, is from 0.001 mass % to 0.4 mass % inclusive. Water-insoluble inorganic particles are contained at least either on the surface or near the surface of the water absorbing resin particles as stated above. That improves saline flow conductivity and powder fluidity at high humidity. In addition, the aforementioned polyvalent metal salt also resides at least either on the surface or near the surface of the water absorbing resin particles. The synergistic effects of the water-insoluble inorganic particles and the polyvalent metal salt further enhances the physical properties of the resultant water absorbing agent.

The water absorbing agent has an absorbency against a pressure of 4.83 kPa (AAP) of preferably 16 g/g or more. The maximum value, although not limited in any particular manner, is preferably 30 g/g or less. If the absorbency against a pressure of 4.83 kPa (AAP) is less than 16 g/g, the resultant water absorbing agent, when used in the water absorbent core, has a relatively high level of liquid seeping, or "rewetting," when the water absorbent core is placed under pressure.

Manufacturing Method for Water Absorbing Agent

The method of manufacturing a water absorbing agent of the present embodiment (manufacturing method A) is a method of manufacturing a water absorbing agent containing water absorbing resin particles which has an internal crosslinking structure obtained by polymerization of a water-soluble unsaturated monomer. In the method, the water absorbing resin particles are mixed with water-insoluble inorganic particles while the resin particles are being surface crosslinked or before or after that crosslinking. The resin particles are crosslinked near the surface with an organic surface crosslinking agent and/or a water-soluble inorganic surface crosslinking agent. The resin particles have a mass median particle size of 200 to 500 µm. The resin particles contain 5 mass % or less particles which have such a size that they can pass through a sieve having a mesh opening size of 150 µm. The inorganic particles have at least on the surface thereof functional groups which are capable of forming ionic bonds with functional groups on the surface of the water absorbing resin particles.

The water absorbing resin particles used in the method of manufacturing a water absorbing agent of the present embodiment are preferably the aforementioned water absorbing resin particles. In addition, the water-insoluble inorganic particles used in the method of manufacturing a water absorbing agent of the present embodiment are preferably the aforementioned water-insoluble inorganic particles.

In the method of manufacturing a water absorbing agent of the present embodiment, the water-insoluble inorganic particles are added in an amount of 1 to 10,000 ppm, more preferably 5 to 1,500 ppm, most preferably 10 to 990 ppm, to the water absorbing resin particles. If there are contained too many water-insoluble inorganic particles, fine particles may fly away during the manufacture of an absorbent core, possibly raising safety/hygiene issues or inducing degradation of the performance of the absorbent core. In addition, the resultant agent, when used in an absorbent core, may be such that the absorbent core does no show excellent vertical liquid suction capability, (i.e., fixed height absorbency (FHA)).

The most preferred form of the method of manufacturing a water absorbing agent involves a step of mixing an at least trivalent water-soluble polyvalent metal salt as a solution (preferably, aqueous solution) with the water absorbing resin particles and a step of mixing the water-insoluble inorganic particles.

The water absorbing agent of the present embodiment may be manufactured by a method of manufacturing a water absorbing agent, with an internal crosslinking structure, which contains water absorbing resin particles obtained by polymerization of a water-soluble unsaturated monomer. The water absorbing resin particles are crosslinked near the surface with a surface crosslinking agent. The water absorbing resin particles have a mass median particle size of 200 µm to 500 µm inclusive. Silicon dioxide of which the residual silanol group concentration is 1.7 $SiOH/nm^2$ or lower is mixed with the water absorbing resin particles in an amount of 10 ppm to 1,900 ppm inclusive based on the resin particles at least at a time selected from the group consisting of while being crosslinked with the surface crosslinking agent, before that crosslinking, and after that crosslinking. This method is called manufacturing method B.

In the method of manufacturing a water absorbing agent of the present embodiment (manufacturing method B), the water absorbing resin particles are first crosslinked near the surface with a surface crosslinking agent. The surface crosslinking agent and method mentioned under the heading "Water Absorbing Resin Particles" may be employed.

The timing of mixing the silicon dioxide or other water-insoluble inorganic particles and the water absorbing resin particles may be at least a time selected from the group consisting of while being crosslinked with the surface crosslinking agent, before the crosslinking, or after the crosslinking. The timing is not limited in any particular manner. The timing is preferably after the crosslinking, more preferably after crosslinking and when the particles are mechanically damaged.

The specific method of mixing the silicon dioxide or other water-insoluble inorganic particles with the water absorbing resin particles in manufacturing methods A, B may use any publicly known stirring device: to name a few examples, the paddle blender, the ribbon mixer, the rotary blender, the jar tumbler, the browser mixer, the mortar mixer. These stirring devices may include a heating device which heats the mixture of the water absorbing resin particles and the water-insoluble inorganic particles and also a cooling device which cools down the mixture heated up by the heating device.

Stirring time, although not limited in any particular manner, is preferably 60 minutes or shorter, more preferably 30 minutes or shorter.

It is important to prevent the water absorbing resin particles and the silicon dioxide or other water-insoluble inorganic particles from aggregating when they are mixed, because they are particulate powder. Therefore, the water-insoluble inorganic particles and the water absorbing resin particles are preferably transported pneumatically when or after the water-insoluble inorganic particles and the water absorbing resin particles are mixed. The pneumatic transportation prevents the water absorbing resin particles and the silicon dioxide or other water-insoluble inorganic particles from aggregating. Therefore, the silicon dioxide or other water-insoluble inorganic particles can be uniformly mixed with the water absorbing resin particles. The physical properties of the water absorbing agent obtained are enhanced.

In the manufacturing methods (manufacturing methods A, B), the polyvalent metal salt and the water absorbing resin particles are mixed preferably at least while being crosslinked with the surface crosslinking agent, before that crosslinking, or after that crosslinking, so as to manufacture a water absorbing agent with excellently balanced centrifuge retention capacity and saline flow conductivity.

The amount of the polyvalent metal salt used is preferably from 0.001 mass % to 5 mass % inclusive, more preferably from 0.01 mass % to 1 mass % inclusive, based on the water absorbing resin particles.

When the polyvalent metal salt is mixed, the salt is preferably mixed as an aqueous solution. The concentration of the water-soluble polyvalent metal salt in the aqueous solution containing the polyvalent metal salt is preferably 50% or more, more preferably 60% or more, even more preferably 70% or more, still more preferably 80% or more, yet more preferably 90% or more, relative to the saturation concentration, so as to prevent infiltration and diffusion into the water absorbing resin particles. The salt may of course be used at the saturation concentration. In addition, the aforementioned hydrophilic organic solvent and an organic acid (or salt thereof), such as lactic acid (or salt thereof), may be present together in an aqueous solution containing at least the polyvalent metal salt. The co-presence of the hydrophilic organic solvent and an organic acid is preferred because, at least the infiltration and diffusion of the polyvalent metal salt into the water absorbing resin particles are limited, and the salt is better mixed.

The stirring device which mixes the polyvalent metal salt, although not limited in any particular manner, may be one of the aforementioned stirring devices, used with the water-insoluble inorganic particles. Stirring time may also be specified similarly to the case of the aforementioned water-insoluble inorganic particles.

In the method of manufacturing a water absorbing agent, the silicon dioxide or other water-insoluble inorganic particles and the water absorbing resin particles are mixed preferably after the water absorbing resin particles are mechanically damaged, so as to irregularly pulverize the water absorbing resin particles. Since the water absorbing resin particles are irregularly pulverized, the silicon dioxide or other water-insoluble inorganic particles can be efficiently contained at least either on the surface or near the surface of the water absorbing resin particles, and the physical properties of the water absorbing agent obtained are improved.

Mechanical damage refers to colliding glass, metal, etc. against the water absorbing resin particles to give physical impact.

Mechanical damage may be given to the water absorbing resin particles by any means so long as the water absorbing resin particles receive impact. For example, a glass container, into which the water absorbing resin particles and glass beads have been placed, may be shaken to give mechanical damage (paint shaker test, which will be further described later). Other methods of giving mechanical damage to the water absorbing resin particles are: a method of placing the water absorbing resin particles in a cylindrical container together with balls and rotating the container (ball mill); a method of stirring in a stirrer equipped with stirring blades; a method of passing through a paddle dryer (heater/cooler equipped with a paddle); a method of pulverizing in a pulverizing device; a method of transporting pneumatically; and a method of colliding or rubbing the particles of the water absorbing agent with one another.

In addition, to obtain a water absorbing agent with superior excellent SFC, it is especially preferable to give mechanical damage to the water absorbing resin particles after the particles are surface crosslinked, pulverize the particles, mix the pulverized water absorbing resin particles with the polyvalent metal salt, then give mechanical damage again to the water absorbing resin particles, and add the silicon dioxide or other water-insoluble inorganic particles.

The water absorbing agent of the present embodiment may be manufactured by a method of manufacturing a water absorbing agent which contains water absorbing resin particles obtained by polymerization of a water-soluble unsaturated monomer. The water absorbing resin particles are crosslinked or coated near the surface with a surface crosslinking agent which has at least one hydroxyl group, The water absorbing resin particles have a mass median particle size of 200 μm to 500 μm inclusive. After the water absorbing resin particles are crosslinked or coated with the surface crosslinking agent, the polyvalent metal salt and the water-insoluble inorganic particles are mixed with the water absorbing resin particles. This method is called manufacturing method C.

In the manufacturing method, the water absorbing resin particles are first crosslinked or coated near the surface with a surface crosslinking agent which has at least one hydroxyl group. The surface crosslinking agent and method mentioned under the heading "Water Absorbing Resin Particles" may be employed.

The steps of manufacturing method C, except the surface crosslinking step, can be implemented by the corresponding steps of manufacturing methods A, B described above.

Water Absorbent Core

The water absorbent core of the present embodiment contains the water absorbing agent described in the foregoing. The water absorbent core, when used in combination with an appropriate material, is suited for use as an absorbent layer in sanitary/hygienic materials, for example. The following will describe the water absorbent core.

The water absorbent core is a molded composition made of the water absorbing agent and other materials. The core is used in disposable diapers, sanitary napkins, incontinent pads, medical pads, and like sanitary/hygienic materials to absorb blood, body fluids, urine, etc. An example of the other materials used is cellulose fiber. Concrete examples of cellulose fiber include mechanical pulp made from wood; wood pulp fibers, such as chemical pulp, semi-chemical pulp, and soluble pulp; and artificial cellulose fibers, such as rayon and acetate. Preferred cellulose fiber is the wood pulp fibers. The cellulose fiber may partially contain nylon, polyester, or another synthetic fiber. When the water absorbing agent of the present embodiment is used as part of the water absorbent core, the mass of the water absorbing agent contained in the water absorbent core is preferably 20 mass % or more, more preferably 30 mass % or more, even more preferably 40 mass % or more. If the mass of the water absorbing agent of the present invention contained in the water absorbent core is less than 20 mass %, sufficient effects may not be accomplished.

A publicly known, suitable method for producing a water absorbent core may be selected to produce the water absorbent core from the water absorbing agent of the present embodiment and the cellulose fiber. For example, the water absorbing agent may be sprayed onto sheets or mats made of the cellulose fiber and sandwiching more of the agent between them if necessary. Alternatively, the cellulose fiber may be uniformly blended with the water absorbing agent. A preferred method is to dry mix the cellulose fiber with the water absorbing agent and compress the mixture. This method is highly capable of restraining the water absorbing agent from falling off the cellulose fiber. The compression is preferably carried out on heating at, for example, 50° C. to 200° C. inclusive. Other preferred methods of producing an absorbent core are described in the Specification of U.S. Pat. No. 5,849,405 and U.S. Published Patent Application 2003/060112.

The water absorbing agent of the present embodiment, when used in the water absorbent core, exhibits excellent physical properties; the resultant water absorbent core is of very excellent quality in that it can quickly absorb liquid, leaving only a little liquid on its surface.

The water absorbing agent of the present embodiment has an excellent water absorption property and hence is applicable to water absorbing/retaining agents for various purposes: for example, water absorbing/retaining agents for absorbent articles, such as disposable diapers, sanitary napkins, incontinent pads, and medical pads; agriculture/horticulture water retaining agents, such as bog moss replacements, soil conditioners, water retaining agents, and agricultural effect keeping agents; water retaining agents for construction purposes, such as dew inhibitors for interior wall materials and cement additives; release controlling agents; cold insulators; disposable pocket stoves; sludge coagulating agents; food freshness retaining agents; ion exchange column materials; sludge/oil dehydrates; desiccants; and humidity conditioners. In addition, the water absorbing agent of the present embodiment is especially suitable for use in disposable diapers, sanitary napkins, and like sanitary/hygienic materials for absorbing feces, urine, or blood.

Where the water absorbent core is used in sanitary/hygienic materials, such as disposable diapers, sanitary napkins, incontinent pads, and medical pads, it is preferable if the core is placed between (a) a top sheet, permeable to liquid, provided next to the body of the user and (b) a back sheet, impermeable to liquid, provided next to the clothes of the user away from the body of the user. The water absorbent core may be multi-layered (two or more layers). Further, the core may be used with a pulp layer as an example.

As described in the foregoing, the water absorbing agent of the present embodiment, in other words, is a water absorbing agent containing water absorbing resin particles with an internal crosslinking structure obtained by polymerization of a water-soluble unsaturated monomer. The water absorbing resin particles are, near the surface thereof, crosslinked with a surface crosslinking agent. The water absorbing resin particles contain silicon dioxide at least either on the surface or near the surface. The silicon dioxide has, on the surface thereof, residual silanol groups at a concentration of 1.7 SiOH/nm$^2$ or lower. The water absorbing resin particles contain 10 ppm to 1,900 ppm, inclusive, silicon dioxide The water absorbing agent has a mass median particle size of 200 μm to 500 μm inclusive. The water absorbing agent contains 5 mass % or less particles which have such a size that they can pass through a sieve having a mesh opening size of 150 μm.

According to the arrangement, the water absorbing resin particles in the water absorbing agent are crosslinked near their surface with a surface crosslinking agent. That reduces the amount of liquid which may seep out when the swollen water absorbing agent is placed under pressure. In other words, the absorbency under 4.83 kPa pressure is increased. In addition, the water absorbing resin particles contain silicon dioxide at least either on the surface or near the surface. Since the silicon dioxide has excellent liquid permeability, the water absorbing agent achieves improved liquid permeability.

In addition, since the concentration of residual silanol groups in the silicon dioxide is within the specified range, there could presumably occur limited hydrogen bond formation, which restrains aggregation of the silicon dioxide. In other words, the silicon dioxide is restrained from aggregating and scattering. Therefore, unlike conventional art, even if silicon dioxide is used, dust generation due to silicon dioxide aggregation is prevented. In addition, the silicon dioxide content is within the specified range. Therefore, the resultant water absorbing agent has excellent physical properties and contains a reduced amount of dust. Particles which pass through a sieve having a mesh opening size of 150 μm account for 5 mass % or less of the mass of the entire water absorbing agent obtained. With the reduced fine particle content in the water absorbing agent, dust is produced in a limited amount.

Thus, the resultant water absorbing agent has following features. The silicon dioxide and other particles in the water absorbing agent will not fly off, unlikely to raise safety/hygiene issues, during manufacture of the water absorbing agent. Also, the physical properties of the water absorbent core will not likely be degraded. In addition, since the mass median particle size of the water absorbing agent is within the specified range, liquid permeability, etc. for the liquid to be absorbed are not disturbed; the water absorbing agent has a high liquid permeability.

The water absorbing agent preferably contains a polyvalent metal salt at least either on the surface or near the surface of the water absorbing resin particles in an amount of 0.001 mass % to 5 mass %, inclusive, based on the water absorbing agent.

Accordingly, the water absorbing agent contains the polyvalent metal salt (preferably, a trivalent water-soluble polyvalent metal salt). Therefore, the water absorbing agent achieves an improved saline flow conductivity without largely reducing absorbency under 4.83 kPa pressure or fixed height absorbency. In addition, insufficient replacement of silicon dioxide is compensated for at least either on the surface or near the surface of the water absorbing agent where there is no silicon dioxide. In addition, synergistic effects of the silicon dioxide and the polyvalent metal salt deliver a water absorbing agent with even better physical properties.

The water absorbing agent is preferably such that the water absorbing resin particles are given mechanical damage after being surface crosslinked.

Accordingly, the water absorbing resin particles have an irregularly pulverized shape. Therefore, the silicon dioxide can be efficiently contained at least either on the surface or near the surface.

The water absorbing agent is preferably such that the concentration of the residual silanol groups on the surface of the silicon dioxide is from 0.7 SiOH/nm$^2$ to 1.7 SiOH/nm$^2$ inclusive.

Accordingly, the silicon dioxide is not excessively hydrophobic, but properly so. That prevents the liquid distribution velocity of the water absorbing agent obtained from decreasing.

The water absorbing agent preferably has a liquid distribution velocity of 0.2 (mm/sec) to 10.0 (mm/sec) inclusive. The velocity is more preferably from 0.5 (mm/sec) to 10.0 (mm/sec) inclusive and even more preferably from 0.8 (mm/sec) to 10.0 (mm/sec) inclusive.

Accordingly, the liquid absorbed by the water absorbing agent diffuses efficiently. That improves the liquid suction rate per unit time of the water absorbent core and liquid diffusibility in the water absorbent core. Thus, water absorption capability is improved.

The water absorbing agent preferably contains 300 ppm less dust by mass.

Accordingly, the resultant water absorbing agent contains an even lower amount of dust. The silicon dioxide and other particles in the water absorbing agent will not fly off, unlikely to raise safety/hygiene issues. The physical properties of the water absorbing agent will not likely be degraded.

The water absorbing agent preferably has a negative frictional electric charge.

That prevents the silicon dioxide and the water absorbing agent from aggregating, which in turn restrains the silicon dioxide from coming off the water absorbing resin particles. As a result, the water absorbing agent contains a reduced amount of dust.

The water absorbent core is characterized in that it contains the water absorbing agent.

Accordingly, the resultant water absorbent core has high physical properties and contains a reduced amount of dust.

The method of manufacturing the water absorbing agent of the present embodiment, in other words, is a method of manufacturing a water absorbing agent containing water absorbing resin particles with an internal crosslinking structure obtained by polymerization of a water-soluble unsaturated monomer. The method involves crosslinking the water absorbing resin particles near their surface with a surface crosslinking agent. The water absorbing resin particles have a mass median particle size of 200 μm to 500 μm inclusive. The method further involves mixing silicon dioxide with the water absorbing resin particles at least at a time selected from the group consisting of while crosslinking with the surface crosslinking agent, before that crosslinking, and after that crosslinking. The silicon dioxide is mixed at an amount of from 10 ppm to 1,900 ppm, inclusive, of the water absorbing resin particles and contains residual silanol groups at a concentration of 1.7 SiOH/nm$^2$ or lower.

According to the method, the silicon dioxide is mixed with the water absorbing resin particles. The manufactured water absorbing agent has high physical properties and contains a reduced amount of dust.

The method of manufacturing a water absorbing agent is preferably such that the silicon dioxide is mixed with the water absorbing resin particles after the water absorbing resin particles is given mechanical damage.

Accordingly, the silicon dioxide is mixed with the water absorbing resin particles after the particles are pulverized into irregular shape. The silicon dioxide can be efficiently contained at least either on the surface or near the surface of the water absorbing resin particles. The resultant water absorbing agent has improved physical properties.

The method of manufacturing a water absorbing agent is preferably such that a polyvalent metal salt is mixed with the water absorbing resin particles at least while crosslinking with the surface crosslinking agent, before that crosslinking, or after that crosslinking.

Accordingly, the water absorbing agent contains the polyvalent metal salt (preferably, a trivalent water-soluble polyvalent metal salt). Therefore, the water absorbing agent achieves an improved saline flow conductivity without largely reducing the absorbency under 4.83 kPa pressure or fixed height absorbency. In addition, insufficient replacement of silicon dioxide is compensated for at least either on the surface or near the surface of the water absorbing agent where there is no silicon dioxide. In addition, synergistic effects of the silicon dioxide and the polyvalent metal salt deliver a water absorbing agent with even better physical properties.

The method of manufacturing a water absorbing agent preferably involves pneumatically transporting the silicon dioxide and the water absorbing resin particles while the silicon dioxide is being mixed with the water absorbing resin particles or after that mixing.

Accordingly, the mixture of the silicon dioxide and the water absorbing resin particles is further mixed by the pneumatic transportation. No aggregation occurs. The silicon dioxide is more efficiently mixed with the water absorbing resin particles. Therefore, the silicon dioxide is evenly mixed with the water absorbing resin particles. That improves physical properties of the water absorbing agent obtained.

The water absorbing agent of the present embodiment, in other words, contains water absorbing resin particles with an internal crosslinking structure obtained by polymerization of a water-soluble unsaturated monomer. The water absorbing resin particles are crosslinked near the surface with an organic surface crosslinking agent and/or a water-soluble inorganic surface crosslinking agent. The water absorbing agent has a mass median particle size of 200 to 500 μm. The water absorbing agent contains 5 mass % or less particles which have such a size that they can pass through a sieve having a mesh opening size of 150 μm. The water absorbing agent contains at least on the surface water-insoluble inorganic fine particles that have functional groups capable of forming ionic bonds with functional groups on the surface of the water absorbing resin particles. The water-insoluble inorganic fine particles reside on or near the surface of the water absorbing resin particles.

The water absorbing agent is preferably such that the functional groups on the surface of the water absorbing resin particles are carboxyl groups and that the functional groups at least on the surface of the water-insoluble inorganic fine particles are amino groups.

The water absorbing agent is preferably such that the water absorbing resin particles include particles with a porous structure.

The water absorbing agent containing a water absorbing resin and an inorganic powder that exhibits a pH from 7 to 10, inclusive, when dispersed in a liquid and a specific surface area of 50 cm$^2$/g as measured by BET (see Japanese Unexamined Patent Publication (Tokukai) 2000-93792) is publicly known. Since this technology does not control the particle size of the water absorbing resin or the quantity of fine particles, the technology cannot solve the problems addressed by the present invention. In addition, the water absorbing resin has insufficiently liquid permeability; the absorbent core does not show a sufficient liquid suction rate per unit time.

The method of manufacturing a water absorbing agent of the present embodiment, in other words, is a method of manufacturing a water absorbing agent containing water absorbing resin particles with an internal crosslinking structure obtained by polymerization of a water-soluble unsaturated monomer. The method involves mixing the water absorbing resin particles with water-insoluble inorganic fine particles. The water absorbing resin particles are crosslinked near the surface with an organic surface crosslinking agent and/or a water-soluble inorganic surface crosslinking agent. The particles have a mass median particle size of 200 to 500 μm. The particles include 5 mass % or less particles which have such a size that they can pass through a sieve having a mesh opening size of 150 μm. The water-insoluble inorganic fine particles have at least on the surface functional groups capable of forming ionic bonds with functional groups on the surface of the water absorbing resin particles. The mixing is carried out while the water absorbing resin particles are being surface crosslinked or in the preceding or successive step.

The manufacturing method is preferably such that the water absorbing resin particles are crosslinked by mixing them with an organic surface crosslinking agent and/or a water-soluble inorganic surface crosslinking agent and heating the mixture. The crosslinking agent contains a water-soluble inorganic salt, preferably persulfate, at an amount of from 0.01 to 1.0 mass % based on the water absorbing resin particles.

The manufacturing method is preferably such that the water absorbing resin particles are crosslinked by mixing them with an organic surface crosslinking agent and/or a water-soluble inorganic surface crosslinking agent and heating the mixture. The hydrophilic organic solvent has a boiling point of 100° C. or lower and contains no hydrophilic organic solvent.

The manufacturing method is preferably such that the water-insoluble inorganic fine particles are added in an amount of 10 to 990 ppm.

The manufacturing method preferably further involves mixing the water absorbing resin particles with an at least trivalent water-soluble polyvalent metal salt in 0.001 to 5 mass % while surface crosslinking or in the preceding or successive step.

The manufacturing method preferably contains the step of pneumatically transporting the water absorbing agent after the mixing with the water-insoluble inorganic fine particles.

According to the arrangement, the resultant water absorbing agent and method of manufacturing the water absorbing agent is such that even if water-insoluble inorganic fine particles are contained, fine particles will not fly off, unlikely to raise safety/hygiene issues, in the manufacture of an absorbent core and also that the performance of the absorbent core is not decreased.

In addition, according to the arrangement, the resultant water absorbing agent has an excellent centrifuge retention capacity (CRC) and/or saline flow conductivity (SFC) which indicate the amount of absorption by the water absorbing agent and the liquid permeability of the water absorbing agent respectively. Therefore, the resultant water absorbing agent and method of manufacturing the water absorbing agent is such that the absorbent core has an excellent liquid suction rate per unit time. In addition, according to the arrangement, the resultant water absorbing agent has an balance between the excellent centrifuge retention capacity (CRC) and the saline flow conductivity (SFC) which indicates liquid permeability. Therefore, the resultant water absorbing agent and method of manufacturing the water absorbing agent is such that the absorbent core has an excellent liquid suction rate per unit time.

In addition, according to the arrangement, the resultant water absorbing agent and method of manufacturing the water absorbing agent is such that the water absorbing agent, when used in an absorbent core, imparts excellent vertical liquid suction capability (i.e., excellent fixed height absorbency (FHA)) to the absorbent core.

According to the arrangement, the resultant water absorbing agent has an excellent absorbency against a pressure of 4.83 kPa (AAP). Therefore, the resultant water absorbing agent and method of manufacturing the water absorbing agent is such that the absorbent core causes limited liquid seeping, or "rewetting," when it is placed under pressure.)

The water absorbing agent of the present embodiment is, in other words, is characterized in that it is a water absorbing agent containing water absorbing resin particles with an internal crosslinking structure obtained by polymerization of a water-soluble unsaturated monomer. The water absorbing agent is characterized also by the following features. The water absorbing resin particles are either crosslinked or coated near the surface with a surface crosslinking agent which has at least one hydroxyl group. The water absorbing resin particles contain a polyvalent metal salt and water-insoluble inorganic particles at least either on the surface or near the surface. The water absorbing agent has a mass median particle size of 200 μm to 500 μm inclusive. The water absorbing agent contains 5 mass % or less particles which have such a size that they can pass through a sieve having a mesh opening size of 150 μm.

According to the arrangement, the water absorbing resin particles in the water absorbing agent are either crosslinked or coated near the surface with a surface crosslinking agent. That reduces the amount of liquid which may seep out when the swollen water absorbing agent is placed under pressure. In other words, absorbency under a pressure of 4.83 kPa is increased. In addition, the water absorbing resin particles contain a polyvalent metal salt and water-insoluble inorganic particles at least either on the surface or near the surface. The water-insoluble inorganic particles has an excellent liquid permeability. Therefore, the water absorbing agent has an improved liquid permeability.

In addition, both the polyvalent metal salt and the water-insoluble inorganic particles reside at least either on the surface or near the surface of the water absorbing resin particles. Therefore, the water-insoluble inorganic particles are restrained from flying off presumably by electrostatic interaction, coordinate bonds with the polyvalent metal, and coordinate bonds mediated by water molecules in the air, and hydrogen bonds. Therefore, unlike conventional art, even if the water-insoluble inorganic particles are used, dust generation due to flying water-insoluble inorganic particles is prevented. In addition, the amount of the water-insoluble inorganic particles is within the specified range. Therefore, the resultant water absorbing agent has excellent physical properties and contains a reduced amount of dust. Particles which pass through a sieve having a mesh opening size of 150 μm account for 5 mass % or less of the mass of the entire water absorbing agent obtained. With the reduced fine particle content in the water absorbing agent, dust is produced in a limited amount.

Thus, the resultant water absorbing agent has following features. The water-insoluble inorganic particles and other particles in the water absorbing agent will not fly off, unlikely to raise safety/hygiene issues, during manufacture of the water absorbing agent. Also, the physical properties of the water absorbent core will not likely be degraded. In addition, since the mass median particle size of the water absorbing agent is within in the specified range, liquid permeability, etc. for the liquid to be absorbed are not disturbed; the water absorbing agent has a high liquid permeability.

The water absorbing agent preferably contains a polyvalent metal salt at least either on the surface or near the surface of the water absorbing resin particles in an amount of 0.001 mass % to 5 mass %, inclusive, based on the water absorbing agent.

Accordingly, the resultant water absorbing agent contains the polyvalent metal salt (preferably, a trivalent water-soluble polyvalent metal salt). Therefore, the water absorbing agent achieves an improved saline flow conductivity without largely reducing absorbency under 4.83 kPa pressure or fixed height absorbency. In addition, insufficient water-insoluble inorganic particles are compensated for at least either on the surface or near the surface of the water absorbing agent where there are no water-insoluble inorganic particles. In addition, synergistic effects of the water-insoluble inorganic particles and the polyvalent metal salt deliver a water absorbing agent with even better physical properties.

The water absorbing agent is preferably such that the water-insoluble inorganic particles are silicon dioxide.

Accordingly, interactions take place between the polyvalent metal salt residing at least either on the surface or near the surface of the water absorbing resin particles and the silanol groups residing on the silicon dioxide. That effectively limits the amount of dust.

The water absorbing agent is preferably such that the water absorbing resin particles are given mechanical damage after being surface crosslinked.

Accordingly, the water absorbing resin particles have an irregularly pulverized shape. Therefore, the water-insoluble inorganic particles can be efficiently contained at least either on the surface or near the surface.

The water absorbing agent preferably has a centrifuge retention capacity of 30 g/g inclusive to 50 g/g exclusive and a saline flow conductivity of 10 ($10^{-7} \cdot cm^3 \cdot s \cdot g^{-1}$) or more.

Accordingly, the resultant water absorbing agent has excellent balance between centrifuge retention capacity and saline flow conductivity.

The water absorbing agent preferably has an absorbency of 16 g/g to 30 g/g, inclusive, under 4.83 kPa pressure.

Accordingly, the water absorbing agent discharges a reduced amount of liquid under 4.83 kPa pressure. The resultant water absorbent core allows only a little liquid seeping under pressure in actual use.

The water absorbing agent is preferably such that the particle size distribution of the agent has a logarithmic standard deviation of 0.20 to 0.40 inclusive.

Accordingly, the particle size distribution is narrow. That prevents the liquid permeability of the water absorbing agent and the liquid suction rate per unit time of the water absorbent core from decreasing noticeably.

The water absorbing agent preferably contains 400 ppm or less dust by mass.

Accordingly, the resultant water absorbing agent contains an even lower amount of dust. The water-insoluble inorganic particles and other particles in the water absorbing agent will not fly off, unlikely to raise safety/hygiene issues. The physical properties of the water absorbing agent will not likely be degraded.

The water absorbing agent of the present embodiment, in other words, is characterized in that the water absorbing agent is contained.

Accordingly, the resultant water absorbent core has high physical properties and contains a reduced amount of dust.

The method of manufacturing a water absorbing agent of the present embodiment, in other words, is characterized in that it is a method of manufacturing a water absorbing agent containing water absorbing resin particles with an internal crosslinking structure obtained by polymerization of a water-soluble unsaturated monomer. The method is characterized also in that it involves either crosslinking or coating the water absorbing resin particles (the mass median particle size is from 200 μm to 500 μm inclusive) near the surface with a surface crosslinking agent which has at least one hydroxyl group and mixing, after either the crosslinking or coating with the surface crosslinking agent, the water absorbing resin particles with a polyvalent metal salt and water-insoluble inorganic particles.

According to the method, the water-insoluble inorganic particles are mixed with water absorbing resin particles and a polyvalent metal salt. The manufactured water absorbing agent has high physical properties and contains a reduced amount of dust.

The method of manufacturing a water absorbing agent is preferably such that the water absorbing resin particles are mixed with a polyvalent metal salt and water-insoluble inorganic particles after the water absorbing resin particles is given mechanical damage.

Accordingly, after being irregularly pulverized, the water absorbing resin particles are mixed with the polyvalent metal salt and the water-insoluble inorganic particles. Therefore, the polyvalent metal salt and the water-insoluble inorganic particles can be efficiently contained at least either on the surface or near the surface of the water absorbing resin particles. The resultant water absorbing agent has improved physical properties.

The method of manufacturing a water absorbing agent is preferably such that the water absorbing resin particles are either crosslinked or coated with a surface crosslinking agent which has at least one hydroxyl group before the water absorbing resin particles are mixed with a polyvalent metal salt.

Accordingly, the resultant water absorbing agent contains the polyvalent metal salt (preferably, a trivalent water-soluble polyvalent metal salt). Therefore, the water absorbing agent achieves an improved saline flow conductivity without largely reducing absorbency under 4.83 kPa pressure or fixed height absorbency. In addition, insufficient replacement of water-insoluble inorganic particles compensated for at least either on the surface or near the surface of the water absorbing agent where there are no water-insoluble inorganic particles. In addition, synergistic effects of the water-insoluble inorganic particles and the polyvalent metal salt deliver a water absorbing agent with even better physical properties.

The method of manufacturing a water absorbing agent preferably involves pneumatically transporting the water-insoluble inorganic particles and the water absorbing resin particles while the water-insoluble inorganic particles are being mixed with the water absorbing resin particles or after that mixing.

Accordingly, the mixture of the water-insoluble inorganic particles and the water absorbing resin particles is further mixed by the pneumatic transportation. No aggregation occurs.

The water-insoluble inorganic particles are more efficiently mixed with the water absorbing resin particles. Therefore, the water-insoluble inorganic particles are evenly mixed with the water absorbing resin particles. That improves physical properties of the water absorbing agent obtained.

The water absorbing resin particles are preferably mixed with the water-insoluble inorganic particles after the water absorbing resin particles are mixed with the polyvalent metal salt. Accordingly, at least either on the surface or near the surface of the water absorbing resin particles, the water-insoluble inorganic particles efficiently attach to the polyvalent metal salt via electrostatic interaction, coordinate bonds with the polyvalent metal, coordinate bonds mediated by water molecules in the air, and hydrogen bonds. The amount of dust produced by flying water-insoluble inorganic particles is reduced.

EXAMPLES

The following will more specifically describe the present invention by way of examples. The examples are by no means limiting the present invention. Throughout the following, "mass parts" may be written simply as "parts" and "liter" as "L" only for the sake of convenience. Also, "mass %" may be written as "wt %."

The performance of the water absorbing resin particles or the water absorbing agent was measured by the following methods. Unless otherwise specified, all the measurements were conducted at room temperature (20 to 25° C.) and 50 RH % humidity.

In the cases of the water absorbing agent being used in an end product, such as a sanitary/hygienic material, the water absorbing agent had already absorbed moisture. The water absorbing agent was therefore separated appropriately from the end product and dried under reduced pressure and at low temperature (for example, under 1 mmHg or lower and at 60° C. for 12 hours) before measurements were made. All the water absorbing agents used in the examples and the comparative examples contained 6 mass % or less water.

Centrifuge Retention Capacity (CRC)

Centrifuge retention capacity, or CRC, is absorption capacity for 0.90 mass % saline under no load over 30 minutes. CRC may be referred to as "absorption capacity under no load."

0.200 g of the water absorbing resin particles or water absorbing agent was placed evenly in a bag (85 mm×60 mm) of non-woven fabric ("Heatron Paper" GSP-22, manufactured by Nangoku Pulp Kogyo Co., Ltd.). After heat sealing, the bag was immersed in a largely excessive amount (typically about 500 mL) of 0.90 mass % saline (aqueous solution of sodium chloride) at room temperature. After 30 minutes, the bag was taken out of the saline and centrifuged for 3 minutes in a centrifugal separator ("Centrifuge H-122," manufactured by Kokusan Co., Ltd.) under centrifugal force described in edana ABSORBENCY II 441.1-99 (250 G). The mass, W1 (g), of the bag was then measured. The same process was carried out using no water absorbing resin particles or water absorbing agent, and the mass, W0 (g), of the bag was measured. The centrifuge retention capacity (CRC) was calculated in grams per gram from W1, W0 as given by the following equations:

Centrifuge Retention Capacity (CRC) (g/g)=($W1$ (g)−$W0$ (g))/(Mass (g) of Water Absorbing Resin Particles or Water Absorbing Agent)−1

Absorbency Against Pressure of 4.83 kPa (AAP)

Absorbency against pressure, or AAP, is absorption capacity for 0.90 mass % saline under 4.83 kPa over 60 minutes. AAP may be referred to as absorption capacity under 4.83 kPa. FIG. 1 is a cross-sectional view of an AAP measurement apparatus 10.

In the measurement apparatus 10 shown in FIG. 1, a 400-mesh stainless steel net 2 (mesh opening size 38 μm) was fused to the bottom of a plastic supporter cylinder 1 that had an internal diameter of 60 mm. 0.900 g of the water absorbing resin particles or water absorbing agent was sprayed evenly on the net 2 at room temperature (from 20° C. to 25° C. inclusive) and 50 RH % humidity. A piston 4 and a weight 5 were placed in this order on the water absorbing resin particles or water absorbing agent, or the test sample 3. The piston 4 and weight 5 had an external diameter slightly less than 60 mm so that there occurred no gap between them and the supporter cylinder 1 and their up and down motion was not disturbed. The piston 4 and weight 5 were adjusted so that they could apply a 4.83 kPa (0.7 psi) load evenly. The mass, Wa (g), of the entire measurement apparatus 10 was measured.

A glass filter 7 measuring 90 mm in diameter (manufactured by Sogo Laboratory Glass Works Co., Ltd.; pore diameter 100 to 120 μm) was placed inside a petri dish 6 measuring 150 mm in diameter. 0.90 mass % saline 9 (from 20° C. to 25° C. inclusive) was poured until it sit level with the top face of the glass filter 7. A paper filter 8 measuring 90 mm in diameter ("JIS P 3801, No. 2," Advantec Toyo Kaisha, Ltd.; thickness 0.26 mm, retainable particle size 5 μm) was placed on the filter 7 so that the surface of the filter 8 could be all wet. Excess solution was removed.

The whole measurement apparatus 10 was placed on the wet paper filter so that it could absorb the solution under load. After 1 hour, the whole measurement apparatus 10 was lifted, and its mass Wb (g) was measured. The absorbency under 4.83 kPa (AAP) was calculated in grams per gram from Wa, Wb as given by the following equation:

Absorbency under 4.83 kPa (AAP)=($Wb$ (g)−$Wa$ (g))/(Mass of Water Absorbing Resin particles or Water Absorbing Agent (0.900 g))

Saline Flow Conductivity (SFC)

Figure 2:
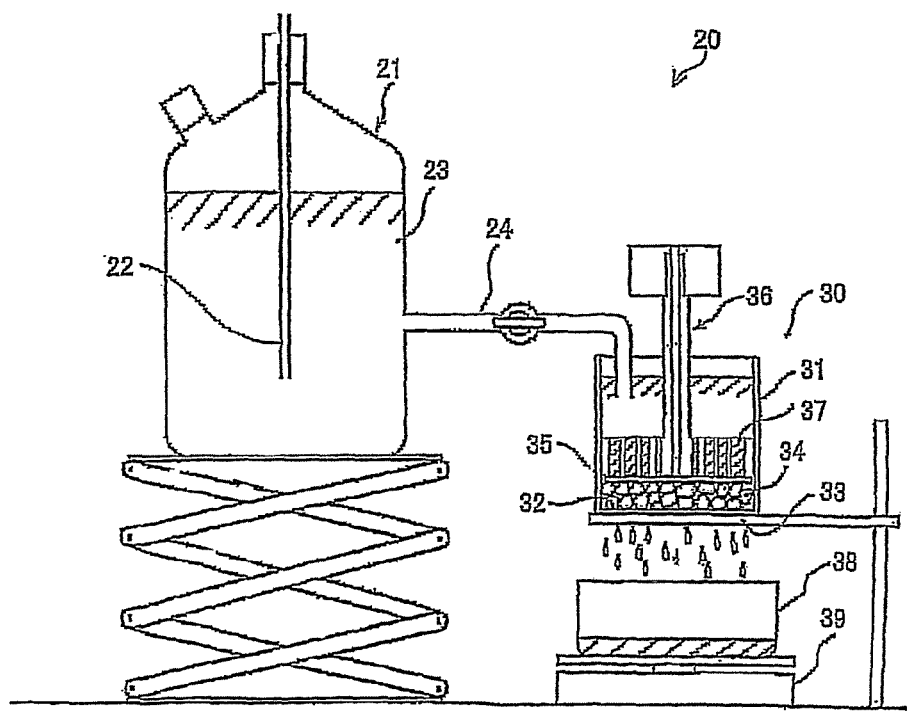
FIG. 2 is a schematic illustration of a SFC measurement apparatus in relation to the present example.

Saline flow conductivity, or SFC, is a value indicating liquid permeability of the water absorbing resin particles or water absorbing agent when they have (it has) swollen. The greater the SFC, the higher liquid permeability the water absorbing resin particles or water absorbing agent have/has. SFC tests were conducted in the examples as described in the Specification of U.S. Pat. No. 5,849,405. FIG. 2 is a schematic illustration of an SFC measurement apparatus 20.

In the measurement apparatus 20 shown in FIG. 2, a glass tube 22 was inserted into a tank 21. The lower end of the glass tube 22 was arranged so that 0.69 mass % saline 23 could be maintained 5 cm above the bottom of a gel 34 in a cell 31. The 0.69 mass % saline 23 in the tank 21 was fed to a cell 41 via a valved "L" tube 24. Under the cell 31 was provided a collector 38 which collected the solution that had passed through the cell 31. The collector 38 was placed on a balance 39. The cell 31 had an internal diameter of 6 cm and was provided with a No. 400 stainless steel net (mesh 38 μm) 32 on the bottom. The piston 36 had, on its lower part, holes 37 through which the solution could properly pass. Also, the piston 36 had a high permeability glass filter 35 attached to its bottom so that the water absorbing resin particles, water absorbing agent, or their swollen gel could not enter the holes 37. The cell 31 was placed on a base. The face of the base at which it contacted the cell 31 was disposed on a stainless steel net 33 which did not disturb the passing solution.

Artificial urine (1) used here was a mixture of 0.25 g calcium chloride dihydrate, 2.0 g potassium chloride, 0.50 g magnesium chloride hexahydrate, 2.0 g sodium sulfate, 0.85 g ammonium dihydrogen phosphate, 0.15 g diammonium hydrogen phosphate, and 994.25 g pure water.

The water absorbing resin particles or water absorbing agent (0.900 g) placed evenly in the container 30 was let to swell, using the measurement apparatus 20 shown in FIG. 2, in artificial urine (1) under a load of 2.07 kPa (0.3 psi) for 60 minutes to prepare the gel 34. Thereafter, the height of the layer of the gel 34 was recorded. Next, the 0.69 mass % saline 23 was passed through the swollen gel layer from the tank 21 under a load of 2.07 kPa (0.3 psi) under a constant hydrostatic pressure. The SFC test was conducted at room temperature (from 20° C. to 25° C. inclusive). The amount of liquid having passed through the gel layer was recorded using a computer and the balance 39 as a function of time at 20 second intervals for 10 minutes. The flow rate Fs(T) at which the solution passed through the swollen gel 34 (primarily between the gel's particles) was determined in units of grams per second by dividing an increase in mass (g) by an increase in time (s). Flow rates were calculated only from the data obtained in the 10 minute period starting at time Ts at which a constant hydrostatic pressure and a stable flow rate were achieved. Fs(T=0), or the first flow rate at which the solution passed through the gel layer, was calculated from the flow rates obtained in the 10 minute period starting at Ts. Fs(T=0) was obtained by extrapolating, for T=0, the result of least square approximation of Fs(T) vs. time.

$$\text{Saline Flow Conductivity }(SFC) = (Fs(T=0) \times L0)/(\rho \times A \times \Delta P)$$
$$= (Fs(T=0) \times L0)/139506$$

where Fs(T=0) was the flow rate in grams per second; L0 was the height of the gel layer in centimeters; $\rho$ was the density of the NaCl solution (=1.003 g/cm$^3$); A was the area of the top face of the gel layer in the cell 31 (=28.27 cm$^2$); and $\Delta P$ was the hydrostatic pressure exerted on the gel layer (=4,920 dyne/cm$^2$). The SFC values were given in units of $10^{-7} \cdot \text{cm}^3 \cdot \text{s} \cdot \text{g}^{-1}$.

Fixed Height Absorbency (FHA)

Fixed Height Absorbency, or FHA, was measured in accordance with the method described in U.S. Published Patent Application 2005/0003191A1. The height upon measurement was set to 20 cm in the present invention.

Mass Median Particle Size D50 and Logarithmic Standard Deviation, $\sigma\zeta$, of Particle Size Distribution These two parameters were measured based on the tests for the mass median particle size, or D50, and the logarithmic standard deviation, $\sigma\zeta$, of a particle size distribution described in International Application Published under PCT WO2004/69915.

The water absorbing resin particles or water absorbing agent was/were sieved using JIS standard sieves having various mesh opening sizes (ex. 850 µm, 710 µm, 600 µm, 500 µm, 425 µm, 300 µm, 212 µm, 150 µm, and 45 µm). The residual percentage R was plotted on a logarithm probability sheet. From the plots, the particle size which corresponded to R=50 mass % was read as the mass median particle size D50. The logarithmic standard deviation, $\sigma\zeta$, of a particle size distribution is given by the following equation. The smaller the $\sigma\zeta$ value, the narrower the particle size distribution.

$$\sigma\zeta = 0.5 \times \ln(X2/X1)$$

where X1 and X2 are particle sizes for R=84.1% and R=15.9% respectively.

Classification was carried out as follows for the purpose of measuring the mass median particle size D50 and the logarithmic standard deviation, $\sigma\zeta$, of the particle size distribution. 10.0 g of the water absorbing resin particles or water absorbing agent was/were placed in each of JIS standard sieves (Iida Testing Sieves: 8 cm in diameter). The mesh openings of the sieves were 850 µm, 710 µm, 600 µm, 500 µm, 425 µm, 300 µm, 212 µm, 150 µm, and 45 µm. The sieves were shaken at room temperature (from 20° C. to 25° C. inclusive) and 50 RH % humidity for 5 minutes using a vibration classifier (Iida Sieve Shaker, ES-65, SER. No. 0501) to classify the particles/agent.

Liquid Distribution Velocity (LDV)

Liquid distribution velocity, or LDV, was measured using a wicking index measurement apparatus described in Japanese Unexamined Patent Publication 5-200068/1993 (Tokukaihei 5-200068; equivalent to EP 532002). The trough sheet was prepared by SUS304, stainless steel, grade 2B finish for measurement.

First, 1.00 g±0.005 g of the water absorbing resin particles or water absorbing agent was/were sprayed evenly from the 0 to 20 cm marks in trough grooves on a trough sheet disposed at an angle of 20°. The water absorbing resin particles or water absorbing agent was/were then more evenly spread using a spatula.

The liquid to be wicked away was 0.9 mass % saline (aqueous solution of sodium chloride) to which "Blue No. 1 for Food Testing" (available from Tokyo Chemical Industry Co., Ltd.) was added in a ratio of 0.01 g for every 1 L of the saline for coloring.

Adjustment was made so that the liquid surface in a liquid storage vessel was 0.5 cm above the lowest point in the trough. After that, measurement of a liquid wicking time (WT) was started right when the stainless steel screen mesh (400-mesh) contacted the liquid. The liquid wicking time (WT) was the time in seconds it took for the liquid to be wicked up to the 10 cm mark. The velocity at which the liquid in the liquid storage vessel and the stainless steel screen mesh were immersed down to 0.5 cm above the lowest point in the trough was from 1.35 to 1.40 mm/s in the direction perpendicular to the liquid surface. The liquid distribution velocity (LDV) was calculated from the following equation:

$$\text{LDV (mm/s)} = 100 \text{ (mm)}/WT \text{ (s)}$$

Ratio of Particles of Sizes which Pass Through 150-µm Mesh Openings of Sieve

The same classification process was performed as in the measurement of the mass median particle size D50 and the logarithmic standard deviation, $\sigma\zeta$, of a particle size distribution. The ratio in mass % of the particles of sizes that could pass through a sieve having 150-µm mesh openings was calculated from the amount of the particles that had passed through that sieve having the 150-µm mesh openings.

Water-Extractable Polymer Content (Water-Soluble Components)

184.3 g of 0.90 mass % saline was prepared in a lidded plastic container (capacity 250 mL). 1.00 g of the water absorbing resin particles or water absorbing agent was added to the aqueous solution. A stirrer was rotated for 16 hours to extract extractable polymer content in the resin by stirring the mixture. The liquid extract was filtered through a paper filter ("JIS P 3801, No. 2," Advantec Toyo Kaisha, Ltd.: thickness 0.26 mm, retainable particle size 5 µm). 50.0 g of the obtained filtrate was set aside for measurement as a sample solution.

First, a 0.1 N aqueous solution of NaOH was added to the 0.90 mass % saline alone, to pH 10. Then, a 0.1 N aqueous solution of HCl was added to pH 2.7 to determine a blank titer ([bNaOH] mL, [bHCl] mL).

The same titration process was performed on the sample solution to determine a titer ([NaOH] mL, [HCl] mL).

In the case of water absorbing resin particles or a water absorbing agent made of known amounts of an acrylic acid and its sodium salt as an example, the extractable polymer content in the water absorbing resin particles or water absorbing agent could be calculated according to the following equation from the average molecular weight of the monomer and the titer determined by the above-mentioned process. If the water absorbing resin particles or agent was/were made of unknown amounts of an acrylic acid and its sodium salt, the average molecular weight of the monomer was calculated based on the neutralization ratio determined by the titration.

Extractable Polymer Content (mass %)=0.1×Average Molecular Weight×184.3×100×([HCl]−[$b$HCl])/ 1,000/1.0/50.0

Neutralization Ratio (mol %)=(1−([NaOH]− [$b$NaOH])/([HCl]−[$b$HCl]))×100

Amount of Dust (Dust Related Properties)

The increase in mass of the dust absorbed and collected by a glass fiber filter over a predetermined period of time under the conditions detailed below was measured as the amount of dust in the water absorbing agent. The measurement was carried out on a Heubach Dustmeter manufactured by Heubach Engineering GmbH in Germany operating in measuring mode I. The atmospheric conditions during the measurement were 25° C. (±2° C.) temperature, 20 to 40% relative humidity, and normal pressure. Specific procedures were as follows.

(1) 100.00 g of a sample (water absorbing agent) was placed in a rotation drum 200.

(2) The mass of the glass fiber filter 50 mm in diameter (retainable particle size 0.5 μm (JIS P3801)) was measured with 0.00001 gram accuracy ("Da" grams). The filter was prepared by fabricating, for example, Advantec's glass fiber, GC-90, or any equivalent to the 50 mm diameter.

(3) A large-scale particle separator 201 was attached to the rotation drum 200. A filter enclosure 202 loaded with a glass fiber filter 204 was also attached.

(4) Conditions were set as follows on the control section 203 of the dustmeter. Measurement was made.

Rotation Rate of Drum=30 R/min

Volume of Absorbed Air=20 L/min

Time (Measurement Period)=30 minutes (5) After the predetermined period, the mass of the glass fiber filter 204 was measured with 0.00001 gram, accuracy ("Db").

The amount of dust was given by:

Amount of Dust (ppm)=($Db$−$Da$)/100.00×1,000,000

Paint Shaker Test

In a paint shaker test (PS), a glass container 6 cm in diameter and 11 cm in height was charged with 10 g of glass beads each 6 mm in diameter and 30 g of water absorbing resin particles or a water absorbing agent and loaded in a paint shaker (No. 488, Toyo Seiki Seisakusho Co., Ltd.) for shaking at 800 cycles per minute (CPM). See Japanese Unexamined Patent Publication 9-235378/1997 (Tokukaihei 9-235378) for details of the device.

Tests in which the shake time was set to 30 minutes and 10 minutes were designated paint shaker test 1 and paint shaker test 2 respectively.

After the shaking, the glass beads were removed using a JIS standard sieve (mesh opening 2 mm), leaving behind damaged water absorbing resin particles or a water absorbing agent.

Frictional Electric Charge 25 g of the water absorbing agent was placed in a glass screw tube and sealed. The screw tube was a screw tube No. 7, available from Maruemu Corporation, measuring 23 mm in internal diameter, 35 mm in external diameter, and 78 mm in height. Its cap was polypropylene, and packing was heat resistant Highsheet.

The screw tube, in which the water absorbing agent was sealed, was shaken continuously for 20 seconds. The shaking could be carried out using a machine or manually. The tube was shaken 3 to 5 times per second, and the displacement in each shake was 10 to 20 cm. The shaking needed to be performed so that the water absorbing agent in the screw tube could be moved as greatly and quickly as possible.

After the 20-second shaking, the water absorbing agent inside the screw tube was immediately spread wide and thin on a sheet. The charge potential of the water absorbing agent was measured using a non-contact static electricity meter ("FMX-002," Simco Japan Inc.) according to the Instruction Manual, prepared by the manufacturer, which accompanied the meter. The measurement of the charge potential had to be completed within 15 seconds after the water absorbing agent was spread wide and thin on a sheet. The distance between the static electricity meter and the water absorbing agent was 25 mm±1 mm during measurement as instructed in the Manual. The charge potential display on the static electricity meter was immediately read over the 15-second measurement time. If the charge potential reading indicated a negative potential, the frictional electric charge was regarded as being negative.

More specifically, if the static electricity meter showed a charge potential in the range of +0.01 to +20.00 kv, the frictional electric charge was regarded as being positive. If the static electricity meter showed a charge potential in the range of −20.00 to −0.01 kv, the frictional electric charge was regarded as being negative. The charge potential as observed in the frictional electric charge measurement is preferably from −10.00 kv to −0.01 kv inclusive, more preferably from −5.00 kv to −0.01 kv inclusive, to keep a low transport speed stability index.

The sheets used in the measurement were 12 cm×12 cm pieces cut out from a glove, "Vinytop Thick Model," from Showa Glove Co. The outside of the glove was polyvinyl chloride resin (non-phthalate plasticizer), the inside was rayon hairs.

When the water absorbing agent was spread wide and thin on a sheet, the outside of the glove was used as the top side of the sheet. On the top side of the sheet was spread a water absorbing agent so that the agent could make a pile of it without flowing out of the sheet. The frictional electric charge was measured in this state. A "pile" of the agent refers to, for example, the water absorbing agent being spread on the sheet, forming a cone or like shape with a height of 2 to 4 cm and a bottom diameter of 7 to 12 cm. The measurement of the frictional electric charge was carried out in a room in which temperature was 23±2° C. and relative humidity was 40±3%.

Proportion of $SiO_2$ in Dust

The proportion of $SiO_2$ in the dust collected in the dust quantity measurement was measured in mass % as the proportion of $SiO_2$ in the dust.

The silicon dioxide in the dust was quantified by analyzing the mass percentages of the elements sodium, aluminum, and silicon in the dust and calculating the mass ratio of the water absorbing resin and the $SiO_2$ from results of the analysis based on the neutralization ratio and weight-average molecular weight of the water absorbing resin (in the case of the neutralization product, or salt, is a salt of sodium).

If the neutralization salt of the water absorbing resin was a monovalent alkali salt/ammonium salt of potassium, lithium, etc., the proportion of $SiO_2$ in the dust could be determined by a similar method. For example, in the case of a potassium salt, the $SiO_2$ proportion of the dust could be determined by analyzing the mass percentages of the elements potassium, aluminum, and silicon.

The quantification analysis of the elements sodium, aluminum, silicon, etc. in the dust was carried out by ZAF using a SEM/EDS (energy dispersive x-ray spectrometer).

Dust samples for the analysis were prepared by collecting appropriate amounts of dust from the glass fiber filter used in the dust quantity measurement and transferring them onto 5 mm×5 mm pieces of carbon tape attached to SEM sample bases. In doing so, the dust was sprayed so that the dust could be distributed evenly on the carbon tape.

Conditions in the analysis are listed below.

Device: Scanning Electron Microscope (Scanning Microscope JSM-5410LV from JOEL)
Acceleration Voltage: 20 kv
Magnification: 20×
Measurement Area: about 900 μm×1,200 μm
Measurement carried out with at least 50 volume % or more of the entire measurement area being covered with dust.
Si Peak SiK 1.739 KeV
Na Peak: NaK 1.041 KeV
Al Peak AlK 1.486 KeV Note that if these peaks overlapped the peak of another element (for example, NaK and ZnLa), the value of the peak of the overlapping, other element (ZnKa in the case of Zn) was subtracted for correction.

From the mass percentage of the element sodium (hereinafter, may be written simply as "Na %"), the mass percentage of the element aluminum (hereinafter, may be written simply as "Al %"), the mass percentage of the element silicon (hereinafter, may be written simply as "Si %"), the neutralization ratio N of the water absorbing resin in mol % (detailed later), and a polymer-unit-weight-average molecular weight Mw, the proportion of $SiO_2$ in the dust was given in mass % by the following equations:

Polymer-unit-weight-average Molecular Weight
$Mw = 72.06 \times (1 - N/100) + 94.05 \times N/100$ Polymer Content $P = (Na\%/23)/(N/100) \times Mw$ $SiO_2$ Content $S = (Si\%/28.08) \times 60.08$ Aluminum Sulfate Content $A = (Al\%/26.98) \times 630.4/2$ Proportion of $SiO_2$ in Dust in mass $\% = S/(P+S+A) \times 100$ In the equations, "N" was the neutralization ratio of the water absorbing resin and could be measured by the same method as the aforementioned method for water-extractable polymer content measurement.

The $SiO_2$ proportion of the dust is preferably measured by the aforementioned method. When there are unknown components or many other elements, elemental analysis or another conventional publicly known method may be used for the measurement.

Flyability of Dust 100 g of a water absorbing agent was placed in a stainless steel funnel (steel designation X5 CrNiMo 17-12-3 specified in ISO/TR 15,510; internal diameter 10 mm; height 145 mm; tilt angle 20°). That funnel containing the water absorbing agent was dropped from the height of 30 cm into a cylindrical beaker 8 cm in diameter and 12 cm in height. It was visually inspected how easily dust was blown up when the funnel hit the beaker. In the measurement, a blackboard was placed close to the cylindrical beaker to make it easier to inspect dust being produced.

The dust's flyability was divided into the following 5 levels.

Flyability 1: Hardly blown up.
Flyability 2: Blown up a little.
Flyability 3: Blown up.
Flyability 4: Blown up rather lot.
Flyability 5: Blown up much.

Quantification Method for Silicon Dioxide in Water Absorbing Agent

The amount of silicon dioxide in the water absorbing agent can be measured by elemental analysis or a like publicly known method. Any measuring method may be used. The following is a mere example.

(1) 0.500 g of a water absorbing agent is placed in a polypropylene beaker (capacity 250 mL). 0.5 g of sodium carbonate (anhydrous) of reagent grade was added.

(2) 100 mL of deionized water (grade 3, ISO 3696) at 80° C. was added to the polypropylene beaker using a 100-mL plastic graduated cylinder. The content of the beaker was stirred for 2 hours while being maintained at 80° C. to dissolve solid silica.

(3) The content was filtered through a pleated quantification paper filter (No. 5C, 185 mm, Toyo Roshi Kaisha, Ltd.) in a plastic funnel. The filtrate was received in a 100-mL plastic graduated flask.

(4) When there remained little liquid on the paper filter in the plastic funnel (≅1 hour later), 3 mL of 6N hydrochloric acid was added using a plastic Komagome pipette so that gel could contract as much as possible.

(5) 3 mL of 6N hydrochloric acid was added to the obtained filtrate. Subsequently, 4 mL of a 5 mass % solution of ammonium molybdate was added twice. An appropriate amount of the deionized water was added to increase the volume of the content. The graduated flask was sealed and shaken well.

(6) The optical absorbency (ABS) of the colored solution obtained in (5) was measured using a spectrophotometer (IU-1100, Hitachi, Ltd.; wavelength 410 nm, cell thickness 10 mm) within 5 to 20 seconds after the coloring occurred. The same process was performed on a blank sample using deionized water (grade 3, ISO 3696).

(7) The optical absorbency value of the blank was subtracted from the obtained optical absorbency of the colored solution. The resultant value was designated the optical absorbency of the test sample. The amount of silicon dioxide fine particles in the test sample was determined in mass % based on a calibration curve (described below).

Preparation of Calibration Curve

Standard samples were prepared by adding 0 mass parts, 0.03 mass parts, 0.06 mass parts, 0.1 mass parts, 0.2 mass parts, 0.3 mass parts, 0.5 mass parts, 1.0 mass part of silicon dioxide fine particles (for example, Aerosil (Registered Trademark) 200 from Nippon Aerosil Co., Ltd.) respectively to 100 mass parts of a water absorbing resin containing no silicon dioxide (for example, water absorbing resin (1-30) which will be detailed later).

The optical absorbencies of these standard samples of which the silicon dioxide fine particle content in mass % is known were determined by the aforementioned process. The calibration curve was drawn from the resultant optical absorbency values.

EXAMPLE 1

436.4 g of an acrylic acid, 4,617.9 g of a 37 mass % aqueous solution of sodium acrylate, 381.0 g of pure water, and 11.40 g of polyethylene glycol diacrylate (molecular weight 523) were dissolved in a reactor which was a lidded double-arm stainless steel kneader (internal volume 10 liters) equipped with two sigma-type blades and a jacket, to prepare a reaction solution. Next, the reaction solution was deaerated in a nitrogen gas atmosphere for 20 minutes. Subsequently, 38.76 g of a 10 mass % aqueous solution of sodium persulfate and 24.22 g of a 0.1 mass % aqueous solution of L-ascorbic acid were added to the reaction solution while stirring, about seconds after which polymerization started. The polymerization was let to proceed at 25 to 95° C., while crushing the produced gel. The water-containing gel-like crosslinked polymer was removed 30 minutes into the polymerization. The resulting water-containing gel-like crosslinked polymer had been comminuted to a size of about 5 mm or less.

The comminuted water-containing gel-like crosslinked polymer was spread on a 50-mesh metal net and dried in hot wind at 180° C. for 50 minutes. The dried substance was pulverized in a roll mill and subjected to a classification using JIS standard sieves having mesh opening sizes of 710 μm and 175 μm. The result was water absorbing resin particles (1) which had an irregularly pulverized shape. Particles (1) had a mass median particle size D50 of 341 μm. The logarithmic standard deviation, σζ, of the particle size distribution of particles (1) was 0.33. Water absorbing resin particles (1) had a centrifuge retention capacity (CRC) of 35.4 g/g and contained a 7.3 mass % water-extractable polymer content.

100 mass parts of water absorbing resin particles (1) obtained was evenly mixed with a surface crosslinking agent that was a mixed solution of 0.384 mass parts of 1,4-butanediol, 0.632 mass parts of propylene glycol, 3.39 mass parts of pure water, and 0.1 mass parts of sodium persulfate. The mixture was then heat treated at 212° C. Different mixture samples were prepared with different heating times: 30 minutes, 35 minutes, 40 minutes, and 45 minutes. Thereafter, the resulting particles were disintegrated until they could pass through a JIS standard sieve having a mesh opening size of 710 μm. Next, the disintegrated particles were subjected to paint shaker test 1, to prepare surface-crosslinked water absorbing resin particle samples: one of the samples was heated for 30 minutes to prepare water absorbing resin particles (1-30), another one for 35 minutes to prepare water absorbing resin particles (1-35), another one for 40 minutes to prepare water absorbing resin particles (1-40), and another one for 45 minutes to prepare water absorbing resin particles (1-45).

A solution was then added to each 100 mass part sample of the surface-crosslinked water absorbing resin particles obtained. The solution was a mixture of 0.40 mass parts of a 27.5 mass % aqueous solution of aluminum sulfate (equivalent to an 8 mass % aqueous solution of aluminum oxide), 0.134 mass parts of a 60 mass % aqueous solution of sodium lactate, and 0.002 mass parts of propylene glycol. After the addition, the samples were dried in a windless environment at 60° C. for 1 hour. Following the drying, the samples were disintegrated until they could pass through a JIS standard sieve having a mesh opening size of 710 μm. Next, the disintegrated samples were subjected to paint shaker test 2, to prepare water absorbing resin particle samples: water absorbing resin particles (1-30A) was prepared from water absorbing resin particles (1-30), water absorbing resin particles (1-35A) from water absorbing resin particles (1-35), water absorbing resin particles (1-40A) from water absorbing resin particles (1-40), and water absorbing resin particles (1-45A) from water absorbing resin particles (1-45).

0.040 mass parts of HDK (Registered Trademark), H2050EP, from Wacker was added to 100 mass parts of water absorbing resin particles (1-30A), (1-35A), (1-40A), and (1-45A) to prepare water absorbing agents (1-1), (1-2), (1-3), and (1-4) respectively.

Likewise, 0.070 mass parts of HDK (Registered Trademark), H2050EP, from Wacker was added to 100 mass parts of water absorbing resin particles (1-30A), (1-35A), (1-40A), and (1-45A) to prepare water absorbing agents (1-5), (1-6), (1-7), and (1-8) respectively.

COMPARATIVE EXAMPLE 1

The following experiments were conducted in reference to referential example 1, example 1, and example 2 of Japanese Unexamined Patent Publication (Tokukai) 2000-93792.

1.70 mass parts of trimethylolpropane triacrylate was dissolved in 5,500 mass parts of an aqueous solution of sodium acrylate (monomer concentration 38%) which had a neutralization ratio of 75 mol %, to prepare a reaction solution. Next, the reaction solution was deaerated in a nitrogen gas atmosphere for 30 minutes. The reaction solution was then fed to a reactor which was a lidded double-arm stainless steel kneader (internal volume 10 liters) equipped with two sigma-type blades and a jacket. Nitrogen gas was substituted for the system while keeping the reaction solution at 30° C. Subsequently, 2.46 mass parts of sodium persulfate and 0.10 mass parts of L-ascorbic acid were added to the reaction solution while stirring, about 1 minute after which polymerization started. The polymerization was let to proceed at 30° C. to 80° C. inclusive. The water-containing gel-like polymer was removed 60 minutes into the polymerization. The resulting water-containing gel-like polymer had been comminuted to a size of about 5 mm.

The comminuted water-containing gel-like polymer was spread on a 50-mesh metal net and dried in hot wind at 150° C. for 90 minutes. The dried substance was pulverized in a vibration mill and subjected to a classification using a 20-mesh metal net. The result was irregularly pulverized water absorbing resin precursor (A) with a mean particle size of 330 μm.

100 mass parts of water absorbing resin precursor (A) obtained was mixed with a surface crosslinking agent that was a mixed solution of 1 mass part of propylene glycol, 0.05 mass parts of ethylene glycol diglycidyl ether, 3 mass parts of water, and 1 mass part of isopropyl alcohol. The mixture was then heat treated at 210° C. for 40 minutes, to obtain comparative water absorbing resin particles (1-1). The absorption capacity and absorption capacity against pressure of comparative water absorbing resin particles (1-1) were measured by the method described in Japanese Unexamined Patent Publication (Tokukai) 2000-93792; the CRC was 31 g/g, and the AAP was 33 g/g.

0.05 mass parts of hydrophobic silicon dioxide (RA200HS manufactured by Nippon Aerosil Co., Ltd.), as inorganic powder, was mixed with 100 mass parts of comparative water absorbing resin particles (1-1), to obtain comparative water absorbing agent (1-1). The hydrophobic silicon dioxide was a 4% cationic dispersion liquid with a pH of 7.5 or higher and a specific surface area of 145±15 m²/g as measured by BET.

100 mass parts of water absorbing resin precursor (A) obtained was mixed with a surface crosslinking agent that was a mixed solution of 0.1 mass parts of ethylene glycol diglycidyl ether, 4.5 mass parts of water, and 1.5 mass parts of isopropyl alcohol. The mixture was heat treated at 200° C. for 35 minutes, to obtain comparative water absorbing resin particles (1-2). The absorption capacity and absorption capacity against pressure of comparative water absorbing resin particles (1-2) were measured by the method described in Japanese Unexamined Patent Publication (Tokukai) 2000-93792; the CRC was 32 g/g, and the AAP was 31 g/g.

1 mass part of water was added to 100 mass parts of comparative water absorbing resin particles (1-2). Thereafter, 0.1 mass parts of the inorganic powder (RA200HS manufactured by Nippon Aerosil Co., Ltd.) was mixed with the result similarly to the foregoing case, to obtain comparative water absorbing agent (1-2).

Table 1 shows measurements of physical properties of water absorbing resin particles (1), (1-30), (1-35), (1-40), (1-45), (1-30A), (1-35A), (1-40A), and (1-45A), water absorbing agent (1-1), (1-2), (1-3), (1-4), (1-5), (1-6), (1-7), and (1-8), comparative water absorbing resin particles (1-1) and (1-2), and comparative water absorbing agents (1-1), (1-2).

EXAMPLE 2

436.4 g of an acrylic acid, 4,617.9 g of a 37 mass % aqueous solution of sodium acrylate, 381.0 g of pure water, and 11.40 g of polyethylene glycol diacrylate (molecular weight 523) were dissolved in a reactor which was a lidded double-arm stainless steel kneader (internal volume 10 liters) equipped with two sigma-type blades and a jacket, to prepare a reaction solution. Next, the reaction solution was deaerated in a nitrogen gas atmosphere for 20 minutes. Subsequently, 29.07 g of a 10 mass % aqueous solution of sodium persulfate and 24.22 g of a 0.1 mass % aqueous solution of L-ascorbic acid were added to the reaction solution while stirring, about 1 minute after which polymerization started. The polymerization was let to proceed at 25 to 95° C., while crushing the produced gel. The water-containing gel-like crosslinked polymer was removed 30 minutes into the polymerization. The resulting water-containing gel-like crosslinked polymer had been comminuted to a size of about 5 mm or less.

The comminuted water-containing gel-like crosslinked polymer was spread on a 50-mesh metal net and dried in hot wind at 180° C. for 50 minutes. The dried substance was pulverized in a roll mill and subjected to a classification using JIS standard sieves having mesh opening sizes of 710 μm and 175 μm. The result was water absorbing resin particles (2) which had an irregularly pulverized shape. Particles (2) had a mass median particle size D50 of 341 μm. The logarithmic standard deviation, σζ, of the particle size distribution of particles (2) was 0.33. Water absorbing resin particles (2) had a centrifuge retention capacity (CRC) of 33.5 g/g and contained a 9.0 mass % water-extractable polymer content.

100 mass parts of water absorbing resin particles (2) obtained was evenly mixed with a surface crosslinking agent that was a mixed solution of 0.384 mass parts of 1,4-butanediol, 0.632 mass parts of propylene glycol, 3.39 mass parts of pure water, and 0.1 mass parts of sodium persulfate. The mixture was then heat treated at 212° C. for 50 minutes. The particles were disintegrated until they could pass through a JIS standard sieve having a mesh opening size of 710 μm. Next, the disintegrated particles were subjected to paint shaker test 1, to obtain surface-crosslinked water absorbing resin particles (2-50).

Different amounts of HDK (Registered Trademark), H2050EP, from Wacker were added to 100 mass part samples of water absorbing resin particles (2-50): 0.010 mass parts of the HDK was added to one of the samples to prepare water absorbing agent (2-1), 0.020 mass parts to prepare water absorbing agent (2-2), 0.040 mass parts to prepare water absorbing agent (2-3), 0.070 mass parts to prepare water absorbing agent (2-4), and 0.100 mass parts to prepare water absorbing agent (2-5).

COMPARATIVE EXAMPLE 2

0.300 mass parts of HDK (Registered Trademark), H2050EP, from Wacker was added to 100 mass parts of water absorbing resin particles (2-50) obtained in example 2 to prepare comparative water absorbing agent (2-1). 0.3000 mass parts of Aerosil (Registered Trademark) 200 from Nippon Aerosil Co., Ltd. was added to another 100 mass parts of water absorbing resin particles (2-50) to prepare comparative water absorbing agent (2-2).

Table 2 shows measurements of some physical properties of water absorbing resin particles (2) and (2-50), water absorbing agents (2-1), (2-2), (2-3), (2-4), and (2-5), and comparative water absorbing agents (2-1) and (2-2).

EXAMPLE 3

Solution (A1) and solution (B1) were mixed in a polypropylene container (internal diameter 80 mm; internal volume 1 liter) covered with styrene foam (heat insulation material). The mixing was performed quickly in an open system by adding solution (B1) to solution (A1) while stirring with a magnetic stirrer. Solution (A1) was a mixture of 220.81 g of an acrylic acid, 1.154 g of polyethylene glycol diacrylate (molecular weight 523), and 1.35 g of a 1.0 mass % aqueous solution of pentasodium diethylenetriaminepentaacetate. Solution (B1) was a mixture of 184.49 g of a 48.5 mass % aqueous solution of sodium hydroxide and 179.94 g of ion-exchanged water of which the temperature was adjusted to 50° C. The result of the mixing was a monomer aqueous solution, of which the temperature had risen to about 100° C. due to heat of neutralization and dissolution.

12.26 g of a 3 mass % aqueous solution of sodium persulfate was added to the obtained monomer aqueous solution. After stirring several seconds, the solution was poured into a tray-type stainless steel container in an open system. For the pouring, the container had been heated on a hot plate (Neo Hotplate H1-1000, manufactured by As One Corporation) so that the surface temperature reached 100° C. The container had a bottom (250×250 mm) the inside of which was coated with Teflon (Registered Trademark). Its top was 640×640 mm and height was 50 mm. The cross-section of its mid-section was trapezoidal. Its top was open.

Soon after the monomer aqueous solution was poured into the tray, polymerization started. The polymerization proceeded producing water vapor, with the solution foamed/expanded in every direction. Thereafter, the content shrank to a size a little larger than the tray bottom. The expansion and shrink finished in about 1 minute. After being left in the container for 4 minutes, the water-containing polymer was removed.

The obtained water-containing polymer was crushed using a meat chopper with a dice size of 9.5 mm (Royal Meat Chopper VR400K manufactured by Iidzuka Industries Co., Ltd.) to obtain a comminuted water-containing polymer.

The comminuted water-containing gel-like crosslinked polymer was spread on a 50-mesh metal net and dried in hot wind at 180° C. for 50 minutes. The dried substance was then pulverized in a roll mill and subjected to a classification using JIS standard sieves having mesh opening sizes of 710 μm and 175 μm. The result was water absorbing resin particles (3) which had an irregularly pulverized shape. Particles (3) had a mass median particle size D50 of 329 μm. The logarithmic standard deviation, σζ, of the particle size distribution of particles (3) was 0.31. Water absorbing resin particles (3) had a centrifuge retention capacity (CRC) of 33.0 g/g and contained a 9.0 mass % water-extractable polymer content.

100 mass parts of water absorbing resin particles (3) obtained was mixed with a surface crosslinking agent that was a mixed solution of 0.36 mass parts of 1,4-butanediol, 0.6 mass parts of propylene glycol, and 3.2 mass parts of pure water. The mixture was then mixed using a Loedige mixer and heat treated at 200° C. for 50 minutes. The particles were disintegrated until they could pass through a JIS standard sieve having a mesh opening size of 710 µm. Next, the disintegrated particles were subjected to paint shaker test 1, to obtain surface-crosslinked water absorbing resin particles (3-50).

A solution was added to 100 mass parts of surface-crosslinked water absorbing resin particles (3-50) obtained. The solution was a mixture of 0.40 mass parts of a 27.5 mass % aqueous solution of aluminum sulfate (equivalent to an 8 mass % aqueous solution of aluminum oxide), 0.134 mass parts of a 60 mass % aqueous solution of sodium lactate, and 0.002 mass parts of propylene glycol. After the addition, the particles were dried in a windless environment at 60° C. for 1 hour. Following the drying, the particles were disintegrated until they could pass through a JIS standard sieve having a mesh opening size of 710 µm. Next, the disintegrated particles were subjected to paint shaker test 2, to obtained water absorbing resin particles (3-50A).

Different amounts of HDK (Registered Trademark), H2050EP, from Wacker were added to 100 mass part samples of water absorbing resin particles (3-50A): 0.020 mass parts of the HDK was added to one of the samples to prepare water absorbing agent (3-1), 0.040 mass parts to prepare water absorbing agent (3-2), 0.060 mass parts to prepare water absorbing agent (3-3), 0.080 mass parts to prepare water absorbing agent (3-4), 0.0990 mass parts to prepare water absorbing agent (3-5), 0.1250 mass parts to prepare water absorbing agent (3-6), and 0.1500 mass parts to prepare water absorbing agent (3-7).

EXAMPLE 4

0.100 mass parts of Aerosil (Registered Trademark) 200 from Nippon Aerosil Co., Ltd. was added to a 100 mass part sample of water absorbing resin particles (3-50A) prepared in example 3 to obtain water absorbing agent (4-1). 0.1250 mass parts of the Aerosil was added to another 100 mass part sample of particles (3-50A) to obtain water absorbing agent (4-2).

Table 3 shows measurements physical properties of water absorbing resin particles (3), (3-50), and (3-50A), water absorbing agents (3-1), (3-2), (3-3), (3-4), (3-5), (3-6), and (3-7), and water absorbing agents (4-1) and (4-2).

EXAMPLE 5

Solution (A) and solution (B) were mixed in a polypropylene container (internal diameter 80 mm; internal volume 1 liter) covered with styrene foam (heat insulation material). The mixing was performed quickly in an open system by adding solution (B) to solution (A) while stirring with a magnetic stirrer. Solution (A) was a mixture of 221.92 g of an acrylic acid, 1.53 g of polyethylene glycol diacrylate (molecular weight 523), and 1.35 g of a 1.0 mass % aqueous solution of pentasodium diethylenetriaminepentaacetate. Solution (B) was a mixture of 180.33 g of a 48.5 mass % aqueous solution of sodium hydroxide and 182.55 g of ion-exchanged water of which the temperature was adjusted to 50° C. The result of the mixing was a monomer aqueous solution, of which the temperature had risen to about 100° C. due to heat of neutralization and dissolution.

12.32 g of a 3 mass % aqueous solution of sodium persulfate was added to the obtained monomer aqueous solution. After stirring several seconds, the solution was poured into a tray-type stainless steel container in an open system. For the pouring, the container had been heated on a hot plate (Neo Hotplate H1-1000, manufactured by As One Corporation) so that the surface temperature reached 100° C. The container had a bottom (250×250 mm) the inside of which was coated with Teflon (Registered Trademark). Its top was 640×640 mm and height was 50 mm. The cross-section of its mid-section was trapezoidal. Its top was open.

Soon after the monomer aqueous solution was poured into the tray, polymerization started. The polymerization proceeded producing water vapor, with the solution foamed/expanded in every direction. Thereafter, the content shrank to a size a little larger than the tray bottom. The expansion and shrink finished in about 1 minute. After being left in the container for 4 minutes, the water-containing polymer was removed.

The obtained water-containing polymer was crushed using a meat chopper with a dice size of 9.5 mm (Royal Meat Chopper VR400K manufactured by Iidzuka. Industries Co., Ltd.) to obtain a comminuted water-containing polymer.

The comminuted water-containing gel-like crosslinked polymer was spread on a 50-mesh metal net and dried in hot wind at 180° C. for 50 minutes. The dried substance was then pulverized in a roll mill and subjected to a classification using JIS standard sieves having mesh opening sizes of 710 µm and 175 µm. The result was water absorbing resin particles (5) which had an irregularly pulverized shape. Particles (5) had a mass median particle size D50 of 342 µm. The logarithmic standard deviation, $\sigma_g$, of the particle size distribution of particles (5) was 0.34. Water absorbing resin particles (5) had a centrifuge retention capacity (CRC) of 31.0 g/g and contained a 8.0 mass % water-extractable polymer content.

100 mass parts of water absorbing resin particles (5) obtained was evenly mixed with a surface crosslinking agent that was a mixed solution of 0.31 mass parts of 1,4-butanediol, 0.49 mass parts of propylene glycol, and 2.4 mass parts of pure water. The mixture was then heat treated at 195° C. for 50 minutes. The particles were disintegrated until they could pass through a JIS standard sieve having a mesh opening size of 710 µm. Next, the disintegrated particles were subjected to paint shaker test 1, obtain surface-crosslinked water absorbing resin particles (5-50).

A solution was added to 100 mass parts of surface-crosslinked water absorbing resin particles (5-50) obtained. The solution was a mixture of 0.50 mass parts of a 27.5 mass % aqueous solution of aluminum sulfate (equivalent to an 8 mass % aqueous solution of aluminum oxide), 0.16 mass parts of a 60 mass % aqueous solution of sodium lactate, and 0.0025 mass parts of propylene glycol.

After the addition, the particles were dried in a windless environment at 60° C. for 1 hour. Following the drying, the particles were disintegrated until they could pass through a JIS standard sieve having a mesh opening size of 710 µm. Next, the disintegrated particles were subjected to paint shaker test 2, obtain water absorbing resin particles (5-50A).

Different amounts of HDK (Registered Trademark), H2050EP, from Wacker were added to 100 mass part samples of water absorbing resin particles (5-50A): 0.040 mass parts of the HDK was added to one of the samples to prepare water absorbing agent (5-1), 0.080 mass parts to prepare water absorbing agent (5-2), and 0.1250 mass parts to prepare water absorbing agent (5-3).

Table 4 shows measurements of physical properties of water absorbing resin particles (5), (5-50), (5-50A) and water absorbing agents (5-1), (5-2), and (5-3).

TABLE 1

| | Inorganic Particles Added | Amount Added ppm | CRC g/g | AAP g/g | SFC *1 | FHA g/g | D50 μm | *2 mass % | Amount of Dust ppm |
|---|---|---|---|---|---|---|---|---|---|
| WARPs (1) | | | 35.4 | 9.5 | 0 | | 341 | 1.8 | |
| WARPs (1-30) | | | 31.0 | 26.7 | 17 | | 345 | 1.6 | |
| WARPs (1-35) | | | 29.7 | 26.4 | 37 | | 343 | 1.7 | |
| WARPs (1-40) | | | 27.8 | 25.5 | 49 | | 341 | 1.9 | |
| WARPs (1-45) | | | 27.0 | 24.9 | 44 | | 339 | 2 | |
| WARPs (1-30A) | | | 31.0 | 26.1 | 45 | 25.4 | 346 | 1.3 | 233 |
| WARPs (1-35A) | | | 30.1 | 25.7 | 79 | 24.8 | 345 | 1.5 | 235 |
| WARPs (1-40A) | | | 28.1 | 24.9 | 115 | 23.7 | 343 | 1.7 | 236 |
| WARPs (1-45A) | | | 27.7 | 24.6 | 132 | 22.8 | 341 | 1.9 | 238 |
| WAA (1-1) | HDK H2050EP | 400 | 31.0 | 25.0 | 55 | 25.3 | 346 | 1.3 | 235 |
| WAA (1-2) | HDK H2050EP | 400 | 30.1 | 24.5 | 92 | 24.1 | 345 | 1.5 | 236 |
| WAA (1-3) | HDK H2050EP | 400 | 28.1 | 24.1 | 117 | 23.1 | 343 | 1.7 | 238 |
| WAA (1-4) | HDK H2050EP | 400 | 27.7 | 23.6 | 126 | 22.5 | 341 | 1.9 | 238 |
| WAA (1-5) | HDK H2050EP | 700 | 31.0 | 24.6 | 58 | 24.1 | 346 | 1.3 | 236 |
| WAA (1-6) | HDK H2050EP | 700 | 30.1 | 24.0 | 111 | 23.0 | 345 | 1.5 | 238 |
| WAA (1-7) | HDK H2050EP | 700 | 28.1 | 23.5 | 129 | 22.8 | 343 | 1.7 | 238 |
| WAA (1-8) | HDK H2050EP | 700 | 27.7 | 22.8 | 142 | 22.1 | 341 | 1.9 | 238 |
| C-WARPs (1-1) | | | 29.7 | 23.3 | 13 | | 343 | 6.8 | 358 |
| C-WARPs (1-2) | | | 30.8 | 23.8 | 7 | | 345 | 5.9 | 352 |
| C-WAA (1-1) | RA200HS | 500 | 29.7 | 22.9 | 29 | 21.7 | 343 | 6.8 | 360 |
| C-WAA (1-2) | RA200HS | 1000 | 30.8 | 22.1 | 20 | 21.3 | 345 | 5.9 | 360 |

*1 Units: $10^{-7} \cdot cm^3 \cdot s \cdot g^{-1}$
*2 Ratio of Particles that Passed Through Sieve Having Mesh Opening Size of 150 μm
WARPs: Water Absorbing Resin Particles
WAA: Water Absorbing Agent
C-WARPs: Comparative Water Absorbing Resin Particles
C-WAA: Comparative Water Absorbing Agent As shown in Table 1, water absorbing resin particles (1-30) to (1-45), obtained by adding a surface crosslinking agent to samples of water absorbing resin particles (1), surface-crosslinking the mixtures, and subjecting the results to paint shaker test 1 to create mechanical damage, exhibited relatively low CRCs, but improved AAPs and SFCs when compared to water absorbing resin particles (1).

A comparison of water absorbing resin particles (1-30) to (1-45) clearly shows that the physical properties of the obtained water absorbing resin particles can be adjusted by changing heating time.

Water absorbing resin particles (1-30A) to (1-45A), obtained by treating water absorbing resin particles (1-30) to (1-45) with an aqueous solution of aluminum sulfate and subjecting the results to paint shaker test 2 to create mechanical damage, exhibited slightly low AAPs, but greatly improved SFCs.

Water absorbing agents (1-1) to (1-4), obtained by adding silicon dioxide, which is hydrophobic, to water absorbing resin particles (1-30A) to (1-45A), practically retained good CRCs and AAPs and also exhibited very high SFCs. In other words, very useful water absorbing agents were obtained with high CRC, AAP, and SFC values.

Comparative water absorbing resin particles (1-1) and (1-2), although manufactured using hydrophobic silicon dioxide, contained more than 5 mass % particles that could pass through a sieve having a mesh opening size of 150 μm because the particles did not undergo classification using a JIS standard sieves. The same holds true with the cases of comparative water absorbing agents (1-1) and (1-2). These comparative water absorbing resin particles and comparative water absorbing agents had low liquid permeability because they contain high ratios of particles that could pass through a sieve having a mesh opening size of 150 μm. Accordingly, their SFCs were very low. Their AAPs and FHAs were also low. There occurred much dust.

TABLE 2

| | Inorganic Particles Added | Amount Added ppm | CRC g/g | AAP g/g | SFC *1 | FHA g/g | D50 μm | *2 mass % | Amount of Dust ppm |
|---|---|---|---|---|---|---|---|---|---|
| WAPRs (2) | | | 33.5 | 9.1 | 0 | | 341 | 1.3 | |
| WAPRs (2-50) | | | 28.6 | 25.2 | 38 | 23.5 | 338 | 1.5 | 208 |
| WAA (2-1) | HDK H2050EP | 100 | 28.6 | 24.4 | 55 | 24.3 | 339 | 1.5 | 208 |
| WAA (2-2) | HDK H2050EP | 200 | 28.6 | 24.4 | 58 | 24.3 | 340 | 1.5 | 216 |
| WAA (2-3) | HDK H2050EP | 400 | 28.6 | 23.9 | 70 | 24.1 | 340 | 1.5 | 219 |
| WAA (2-4) | HDK H2050EP | 700 | 28.6 | 23.3 | 71 | 23.6 | 342 | 1.6 | 219 |
| WAA (2-5) | HDK H2050EP | 1000 | 28.5 | 23.1 | 81 | 19.2 | 344 | 1.6 | 245 |
| C-WAA (2-1) | HDK H2050EP | 3000 | 28.5 | 22.8 | 111 | 19.0 | 344 | 1.8 | 340 |
| C-WAA (2-2) | Aerosil 200 | 3000 | 28.5 | 22.0 | 103 | 19.0 | 344 | 1.8 | 393 |

*1 Units: $10^{-7} \cdot cm^3 \cdot s \cdot g^{-1}$
*2 Ratio of Particles that Passed Through Sieve Having Mesh Opening Size of 150 μm
WARPs: Water Absorbing Resin Particles
WAA: Water Absorbing Agent
C-WARPs: Comparative Water Absorbing Resin Particles
C-WAA: Comparative Water Absorbing Agent All the water absorbing resin particles and water absorbing agents in Table 2 had far smaller amounts of dust than comparative water absorbing agents (2-1) and (2-2). Although the same amount of inorganic particles was added to comparative water absorbing agents (2-1) and (2-2), comparative water absorbing agent (2-1) produced less dust and showed better SFC and AAP.

Water absorbing agent (2-1) to (2-4) had especially high FHAs.

As shown in Table 4, water absorbing agents (5-1) to (5-3) exhibited excellent liquid permeabilities (SFCs) and produced very little dust.

EXAMPLE 6

The same process was carried out as in example 1, except that 0.050 mass parts of HDK (Registered Trademark), H20, from Wacker, in place of 0.040 mass parts of HDK (Registered Trademark), H2050EP, from Wacker, was added to 100

TABLE 3

|  | Inorganic Particles Added | Amount Added ppm | CRC g/g | AAP g/g | SFC *1 | FHA g/g | D50 μm | *2 mass % | Amount of Dust ppm |
|---|---|---|---|---|---|---|---|---|---|
| WAPRs (3) |  |  | 33.0 | 9.3 | 0 |  | 329 | 1.6 |  |
| WAPRs (3-50) |  |  | 27.5 | 24.1 | 31 |  | 328 | 1.5 |  |
| WAPRs (3-50A) |  |  | 27.3 | 23.9 | 65 | 23.4 | 330 | 1.7 | 210 |
| WAA (3-1) | HDK H2050EP | 200 | 27.3 | 23.4 | 78 | 23.0 | 330 | 1.7 | 210 |
| WAA (3-2) | HDK H2050EP | 400 | 27.5 | 23.1 | 78 | 22.9 | 331 | 1.7 | 220 |
| WAA (3-3) | HDK H2050EP | 600 | 27.5 | 23.0 | 79 | 22.7 | 330 | 1.7 | 221 |
| WAA (3-4) | HDK H2050EP | 800 | 27.4 | 22.9 | 85 | 22.4 | 331 | 1.8 | 225 |
| WAA (3-5) | HDK H2050EP | 990 | 27.3 | 22.9 | 88 | 22.5 | 331 | 1.8 | 230 |
| WAA (3-6) | HDK H2050EP | 1250 | 27.5 | 22.8 | 101 | 21.7 | 332 | 1.8 | 252 |
| WAA (3-7) | HDK H2050EP | 1500 | 27.6 | 22.4 | 94 | 20.8 | 335 | 1.9 | 260 |
| WAA (4-1) | Aerosil 200 | 1000 | 27.3 | 22.1 | 87 | 21.1 | 332 | 1.8 | 308 |
| WAA (4-2) | Aerosil 200 | 1250 | 27.5 | 22.0 | 92 | 20.3 | 334 | 1.8 | 310 |

*1 Units: $10^{-7} \cdot cm^3 \cdot s \cdot g^{-1}$
*2 Ratio of Particles that Passed Through Sieve Having Mesh Opening Size of 150 μm
WARPs: Water Absorbing Resin Particles
WAA: Water Absorbing Agent
C-WARPs: Comparative Water Absorbing Resin Particles
C-WAA: Comparative Water Absorbing Agent All the water absorbing resin particles and water absorbing agents in Table 3 (especially, water absorbing agents (3-1) to (3-7)) had a very small amount of dust. Specifically, although the same amount of inorganic particles was added to water absorbing agent (3-6) and comparative water absorbing agent (4-2), water absorbing agent (3-6) produced less dust.

Water absorbing agents (3-1) to (3-5) exhibited particularly good FHAs.

mass parts of water absorbing resin particles (1-30A), (1-35A), (1-40A), and (1-45A), to obtain water absorbing agents (6-1), (6-2), (6-3), and (6-4) respectively.

Table 5 shows the kind and amount of silicon dioxide added, as well as measurements of the CRC, AAP, SFC, FHA, D50, and the ratio of particles that passed through a sieve having a mesh opening size of 150 μm, for water absorbing agents (6-1), (6-2), (6-3) and (6-4).

TABLE 4

|  | Inorganic Particles Added | Amount Added ppm | CRC g/g | AAP g/g | SFC *1 | FHA g/g | D50 μm | *2 mass % | Amount of Dust ppm |
|---|---|---|---|---|---|---|---|---|---|
| WAPRs (5) |  |  | 31.0 | 9.5 | 0 |  | 328 | 1.4 |  |
| WAPRs (5-50) |  |  | 26.0 | 93.7 | 52 |  | 329 | 1.4 |  |
| WAPRs (5-50A) |  |  | 25.7 | 23.2 | 96 | 22.3 | 329 | 1.3 | 220 |
| WAA (5-1) | HDK H2050EP | 400 | 25.8 | 22.7 | 110 | 21.7 | 331 | 1.3 | 218 |
| WAA (5-2) | HDK H2050EP | 800 | 25.5 | 22.4 | 141 | 21.5 | 330 | 1.4 | 224 |
| WAA (5-3) | HDK H2050EP | 1250 | 25.8 | 22.3 | 156 | 21.0 | 330 | 1.4 | 255 |

*1 Units: $10^{-7} \cdot cm^3 \cdot s \cdot g^{-1}$
*2 Ratio of Particles that Passed Through Sieve Having Mesh Opening Size of 150 μm
WARPs: Water Absorbing Resin Particles
WAA: Water Absorbing Agent
C-WARPs: Comparative Water Absorbing Resin Particles
C-WAA: Comparative Water Absorbing Agent

TABLE 5

|  | Silicon Dioxide Added | Amount of Silicon Dioxide Added ppm | CRC g/g | AAP g/g | SFC *1 | FHA g/g | D50 μm | *2 mass % | Amount of Dust ppm |
|---|---|---|---|---|---|---|---|---|---|
| WAA (6-1) | HDK H20 | 500 | 30.9 | 25.1 | 60 | 25.3 | 345 | 1.3 | 211 |
| WAA (6-2) | HDK H20 | 500 | 29.7 | 24.5 | 115 | 24.3 | 345 | 1.5 | 212 |
| WAA (6-3) | HDK H20 | 500 | 28.0 | 24.3 | 132 | 23.4 | 344 | 1.7 | 215 |
| WAA (6-4) | HDK H20 | 500 | 27.6 | 23.7 | 156 | 22.9 | 343 | 1.9 | 220 |

*1 Units: $10^{-7} \cdot cm^3 \cdot s \cdot g^{-1}$
*2 Ratio of Particles that Passed Through Sieve Having Mesh Opening Size of 150 μm
WARPs: Water Absorbing Resin Particles
WAA: Water Absorbing Agent
C-WARPs: Comparative Water Absorbing Resin Particles
C-WAA: Comparative Water Absorbing Agent As shown in Table 5, water absorbing agents (6-1) to (6-4) exhibited excellent liquid permeabilities (SFCs) and high AAPs and FHAs, and produced very little dust.

EXAMPLE 7

436.4 g of an acrylic acid, 4,617.9 g of a 37 mass % aqueous solution of sodium acrylate, 381.0 g of pure water, and 7.6 g of polyethylene glycol diacrylate (molecular weight 523) were dissolved in a reactor which was a lidded double-arm stainless steel kneader (internal volume 10 liters) equipped with two sigma-type blades and a jacket, to prepare a reaction solution. Next, the reaction solution was deaerated in a nitrogen gas atmosphere for 20 minutes. Subsequently, 29.07 g of a 10 mass % aqueous solution of sodium persulfate and 24.22 g of a 0.1 mass % aqueous solution of L-ascorbic acid were added to the reaction solution while stirring, about minute after which polymerization started. The polymerization was let to proceed at 25 to 95° C., while crushing the produced gel. The water-containing gel-like crosslinked polymer was removed 30 minutes into the polymerization. The resulting water-containing gel-like crosslinked polymer had been comminuted to a size of about 5 mm or less.

The comminuted water-containing gel-like crosslinked polymer was spread on a 50-mesh metal net and dried in hot wind at 180° C. for 50 minutes. The dried substance was pulverized in a roll mill and subjected to a classification using JIS standard sieves having mesh opening sizes of 710 μm and 175 μm. The result was water absorbing resin particles (7) which had an irregularly pulverized shape. Particles (7) had a mass median particle size D50 of 471 μm. The logarithmic standard deviation, σζ, of the particle size distribution of particles (7) was 0.37. Water absorbing resin particles (7) had a centrifuge retention capacity (CRC) of 38.0 g/g and contained a 11.0 mass % water-extractable polymer content.

100 mass parts of water absorbing resin particles (7) obtained was evenly mixed with a surface crosslinking agent that was a mixed solution of 0.3 mass parts of 1,4-butanediol, 0.5 mass parts of propylene glycol, and 2.7 mass parts of pure water. The mixture was then heat treated at 212° C. for 40 minutes. The particles were disintegrated until they could pass through a JIS standard sieve having a mesh opening size of 850 μm. Next, the disintegrated particles were subjected to paint shaker test 1, to obtain surface-crosslinked water absorbing resin particles (7-40).

A solution was then added to each 100 mass part sample of the water absorbing resin particles (7-40) obtained. The solution was a mixture of 0.40 mass parts of a 27.5 mass % aqueous solution of aluminum sulfate (equivalent to an 8 mass % aqueous solution of aluminum oxide), 0.134 mass parts of a 60 mass % aqueous solution of sodium lactate, and 0.002 mass parts of propylene glycol. After the addition, the samples were dried in a windless environment at 60° C. for 1 hour. Following the drying, the samples were disintegrated until they could pass through a JIS standard sieve having a mesh opening size of 710 μm. Next, the disintegrated samples were subjected to paint shaker test 2, to obtain water absorbing resin particles (7-40A).

Different amounts of HDK (Registered Trademark), H20, from Wacker were added to 100 mass part samples of water absorbing resin particles (7-40A) obtained: 0.020 mass parts of the HDK was added to one of the samples to prepare water absorbing agent (7-1), 0.040 mass parts to prepare water absorbing agent (7-2), 0.070 mass parts to prepare water absorbing agent (7-3), and 0.100 mass parts to prepare water absorbing agent (7-4).

Table 6 shows the kind and amount of silicon dioxide added, as well as measurements of the CRC, AAP, SFC, FHA, LDV, D50, and ratio of particles that passed through a sieve having a mesh opening size of 150 μm, for water absorbing resin particles (7), (7-40), and (7-40A) and water absorbing agents (7-1), (7-2), (7-3), and (7-4). The amounts of dust were also measured, the results of which are shown in Table 6.

EXAMPLE 8

0.200 mass parts of HDK (Registered Trademark), H20, from Wacker was added to 100 mass parts water absorbing resin particles (7-40A) prepared in example 7 to obtain water absorbing agent (8-1).

0.200 mass parts of Aerosil (Registered Trademark) 200 from Nippon Aerosil Co., Ltd. was added to 100 mass parts of water absorbing resin particles (7-40A) prepared in example 7 to obtain water absorbing agent (8-2).

0.200 mass parts of Aerosil (Registered Trademark), R-972, from manufactured by Nippon Aerosil Co., Ltd. was added to 100 mass parts of water absorbing resin particles (7-40A) prepared in example 7, to obtain water absorbing agent (8-3).

Table 6 shows the kind and amount of silicon dioxide added, as well as measurements of the CRC, AAP, SFC, FHA, LDV, D50, and the ratio of particles that passed through a sieve having a mesh opening size of 150 μm, for water absorbing agents (8-1), (8-2) and (8-3). The amounts of dust were also measured, the results of which are shown in Table 6.

TABLE 6

| | Silicon Dioxide Added | Amount of Silicon Dioxide Added ppm | CRC g/g | AAP g/g | SFC *1 | FHA g/g | LDV mm/sec | D50 μm | *2 mass % | Amount of Dust ppm |
|---|---|---|---|---|---|---|---|---|---|---|
| WAPRs (7) | | | 38.0 | 8.6 | 0 | | | 471 | 1.5 | |
| WAPRs (7-40) | | | 29.8 | 25.4 | 28 | | | 471 | 1.6 | |
| WAPRs (7-40A) | | | 29.4 | 24.9 | 47 | 22.3 | 0.72 | 472 | 1.5 | 179 |
| WAA (7-1) | HDK H20 | 200 | 29.7 | 24.3 | 54 | 22.6 | 0.79 | 470 | 1.6 | 180 |
| WAA (7-2) | HDK H20 | 400 | 29.5 | 23.2 | 56 | 21.9 | 0.82 | 472 | 1.6 | 207 |
| WAA (7-3) | HDK H20 | 700 | 29.7 | 23.2 | 65 | 21.5 | 0.73 | 473 | 1.6 | 189 |
| WAA (7-4) | HDK H20 | 1000 | 29.2 | 22.7 | 75 | 21.3 | 0.84 | 471 | 1.6 | 245 |
| WAA (8-1) | HDK H20 | 2000 | 29.0 | 21.1 | 83 | 19.6 | 0.84 | 471 | 1.9 | 301 |
| WAA (8-2) | Aerosil 200 | 2000 | 28.5 | 20.8 | 76 | 19.4 | 1.80 | 472 | 1.8 | 350 |
| WAA (8-3) | Aerosil R-972 | 2000 | 29.0 | 21.0 | 86 | 18.9 | 0.29 | 472 | 1.9 | 302 |

*1 Units: $10^{-7} \cdot cm^3 \cdot s \cdot g^{-1}$
*2 Ratio of Particles that Passed Through Sieve Having Mesh Opening Size of 150 μm
WARPs: Water Absorbing Resin Particles
WAA: Water Absorbing Agent
C-WARPs: Comparative Water Absorbing Resin Particles
C-WAA: Comparative Water Absorbing Agent The measurements for water absorbing agents (7-1) to (7-4) and (8-1) to (8-3) in Table 6 demonstrate that water absorbing agents were obtained which produced very small amounts of dust and showed high SFCs. The amount of dust was less than or equal to 400 ppm for any of water absorbing agents (7-1) to (7-4) and (8-1) to (8-3). Water absorbing agents were manufactured which were unlikely to produce dust.

Water absorbing agents (7-1) to (7-4) exhibited particularly good AAPs and FHAs. Water absorbing agents (7-1) to (7-4), (8-1), and (8-2) exhibited excellent LDVs. The amount of dust was particularly low for water absorbing agents (7-1) to (7-3) and a little low for water absorbing agents (7-4). The amount of dust was also low for water absorbing agents (8-1) and (8-3). Although the same amount of silicon dioxide was added to water absorbing agents (8-1) to (8-3), water absorbing agent (8-2) produced more dust and exhibited a lower AAP and SFC than water absorbing agents (8-1) and (8-3).

EXAMPLE 9

Solution (A) and solution (B) were mixed in a polypropylene container (internal diameter 80 mm; internal volume 1 liter) covered with styrene foam (heat insulation material). The mixing was performed quickly in an open system by adding solution (B) to solution (A) while stirring with a magnetic stirrer. Solution (A) was a mixture of 221.92 g of an acrylic acid, 1.53 g of polyethylene glycol diacrylate (molecular weight 523), and 1.35 g of a 1.0 mass % aqueous solution of pentasodium diethylenetriaminepentaacetate. Solution (B) was a mixture of 180.33 g of a 48.5 mass % aqueous solution of sodium hydroxide and 182.55 g of ion-exchanged water of which the temperature was adjusted to 50° C. The result of the mixing was a monomer aqueous solution, of which the temperature had risen to about 100° C. due to heat of neutralization and dissolution.

12.32 g of a 3 mass % aqueous solution of sodium persulfate was added to the obtained monomer aqueous solution. After stirring several seconds, the solution was poured into a tray-type stainless steel container in an open system. For the pouring, the container had been heated on a hot plate (Neo Hotplate H1-1000, manufactured by As One Corporation) so that the surface temperature reached 100° C. The container had a bottom (250×250 mm) the inside of which was coated with Teflon (Registered Trademark). Its top was 640×640 mm and height was 50 mm. The cross-section of its mid-section was trapezoidal. Its top was open.

Soon after the monomer aqueous solution was poured into the tray, polymerization started. The polymerization proceeded producing water vapor, with the solution foamed/expanded in every direction. Thereafter, the content shrank to a size a little larger than the tray bottom. The expansion and shrink finished in about 1 minute. After being left in the container for 4 minutes, the water-containing polymer was removed.

The obtained water-containing polymer was crushed using a meat chopper with a dice size of 9.5 mm (Royal Meat Chopper VR400K manufactured by Iidzuka Industries Co., Ltd.) to obtain a comminuted water-containing polymer.

The comminuted water-containing gel-like crosslinked polymer was spread on a 50-mesh metal net and dried in hot wind at 180° C. for 50 minutes. The dried substance was then pulverized in a roll mill and subjected to a classification using JIS standard sieves having mesh opening sizes of 710 μm and 175 μm. The result was water absorbing resin particles (9) which had an irregularly pulverized shape. Particles (9) had a mass median particle size D50 of 342 μm. The logarithmic standard deviation, σζ, of the particle size distribution of particles (9) was 0.34. Water absorbing resin particles (9) had a centrifuge retention capacity (CRC) of 31.0 g/g and contained a 8.0 mass % water-extractable polymer content.

100 mass parts of water absorbing resin particles (9) obtained was evenly mixed with a surface crosslinking agent that was a mixed solution of 0.31 mass parts of 1,4-butanediol, 0.49 mass parts of propylene glycol, and 2.4 mass parts of pure water. The mixture was then heat treated at 195° C. for 50 minutes. The particles were disintegrated until they could pass through a JIS standard sieve having a mesh opening size of 710 μm. Next, the disintegrated particles were subjected to paint shaker test 1, to obtain surface-crosslinked water absorbing resin particles (9-50).

A solution was added to 100 mass parts of surface-crosslinked water absorbing resin particles (9-50) obtained. The solution was a mixture of 0.40 mass parts of a 27.5 mass % aqueous solution of aluminum sulfate (equivalent to an 8 mass % aqueous solution of aluminum oxide), 0.16 mass parts of a 60 mass % aqueous solution of sodium lactate, and 0.0025 mass parts of propylene glycol. After the addition, the particles were dried in a windless environment at 60° C. for 1 hour. Following the drying, the particles were disintegrated until they could pass through a JIS standard sieve having a mesh opening size of 710 µm. Next, the disintegrated particles were subjected to paint shaker test 2, obtain water absorbing resin particles (9-50A).

Different amounts of HDK (Registered Trademark), H20, from Wacker were added to 100 mass part samples of water absorbing resin particles (9-50A) obtained: 0.020 mass parts of the HDK was added to one of the samples to prepare water absorbing agent (9-1), 0.040 mass parts to prepare water absorbing agent (9-2), 0.070 mass parts to prepare water absorbing agent (9-3), and 0.100 mass parts to prepare water absorbing agent (9-4).

Different amounts of Aerosil (Registered Trademark), R-972, from manufactured by Nippon Aerosil Co., Ltd. were added to 100 mass part samples of water absorbing resin particles (9-50A) obtained: 0.040 mass parts of the Aerosil was added to one of the samples to prepare water absorbing agent (9-5), 0.070 mass parts to prepare water absorbing agent (9-6), and 0.100 mass parts to prepare water absorbing agent (9-7).

Different amounts of HDK (Registered Trademark), H15, from Wacker, were added to 100 mass part samples of water absorbing resin particles (9-50A) obtained: 0.020 mass parts of the HDK was added to one of the samples to prepare water absorbing agent (9-8), 0.040 mass parts to prepare water absorbing agent (9-9), 0.070 mass parts to prepare water absorbing agent (9-10), and 0.100 mass parts to prepare water absorbing agent (9-11).

Table 7 shows the kind and amount of silicon dioxide added, as well as measurements of the CRC, AAP, SFC, FHA, LDV, D50, and the ratio of particles that passed through a sieve having a mesh opening size of 150 µm, for water absorbing resin particles (9), (9-50) and (9-50A) and water absorbing agents (9-1) to (9-11). The amounts of dust were also measured, the results of which are shown in Table 7.

As shown in Table 7, the amount of dust is less than or equal to 300 ppm for any of water absorbing resin particles (9-50A) and water absorbing agents (9-1) to (9-11). Water absorbing agents were manufactured which were unlikely to produce dust.

Water absorbing agents (9-1) to (9-4) and (9-8) to (9-11) exhibited excellent LDVs.

EXAMPLE 10

425.2 g of an acrylic acid, 4,499.5 g of a 37 mass % aqueous solution of sodium acrylate, 538.5 g of pure water, and 6.17 g of polyethylene glycol diacrylate (molecular weight 523) were dissolved in a reactor which was a lidded double-arm stainless steel kneader (internal volume 10 liters) equipped with two sigma-type blades and a jacket, to prepare a reaction solution. Next, the reaction solution was deaerated in a nitrogen gas atmosphere for 20 minutes. Subsequently, 28.3 g of a 10 mass % aqueous solution of sodium persulfate and 23.6 g of a 0.1 mass % aqueous solution of L-ascorbic acid were added to the reaction solution while stirring, about 25 seconds after which polymerization started. The polymerization was let to proceed at 25° C. to 95° C. inclusive, while crushing the produced gel. The water-containing gel-like crosslinked polymer was removed 30 minutes into the polymerization. The resulting water-containing gel-like crosslinked polymer had been comminuted to a size of about 5 mm or less.

The comminuted water-containing gel-like crosslinked polymer was spread on a 50-mesh metal net and dried in hot wind at 170° C. for 65 minutes. The dried substance was pulverized in a roll mill and subjected to a classification using a JIS standard sieve having a mesh opening size of 850 µm. The result was water absorbing resin particles (10) which had an irregularly pulverized shape. Particles (10) had a mass median particle size D50 of 458 µm. The logarithmic standard deviation, σζ, of the particle size distribution of particles (10)

TABLE 7

| | Silicon Dioxide Added | Amount of Silicon Dioxide Added ppm | CRC g/g | AAP g/g | SFC *1 | FHA g/g | LDV mm/sec | D50 µm | *2 mass % | Amount of Dust ppm |
|---|---|---|---|---|---|---|---|---|---|---|
| WAPRs (9) | | | 31.0 | 9.5 | 0 | | | 328 | 1.4 | |
| WAPRs (9-50) | | | 26.0 | 23.7 | 52 | | | 329 | 1.4 | |
| WAPRs (9-50A) | | | 25.7 | 23.2 | 96 | 22.3 | 1.01 | 329 | 1.3 | 233 |
| WAA (9-1) | HDK H20 | 200 | 25.5 | 23.0 | 112 | 22.3 | 1.15 | 331 | 1.3 | 235 |
| WAA (9-2) | HDK H20 | 400 | 25.5 | 23.0 | 131 | 21.9 | 1.07 | 330 | 1.3 | 248 |
| WAA (9-3) | HDK H20 | 700 | 26.0 | 23.0 | 139 | 21.5 | 1.36 | 332 | 1.3 | 230 |
| WAA (9-4) | HDK H20 | 1000 | 25.8 | 22.9 | 149 | 21.3 | 1.04 | 331 | 1.4 | 245 |
| WAA (9-5) | Aerosil R-972 | 400 | 25.7 | 22.9 | 129 | 21.6 | 0.73 | 332 | 1.3 | 237 |
| WAA (9-6) | Aerosil R-972 | 700 | 25.8 | 22.7 | 166 | 21.3 | 0.52 | 333 | 1.3 | 238 |
| WAA (9-7) | Aerosil R-972 | 1000 | 25.9 | 21.6 | 173 | 21.1 | 0.42 | 332 | 1.4 | 249 |
| WAA (9-8) | HDK H15 | 200 | 25.4 | 23.6 | 126 | 22.3 | 1.14 | 333 | 1.4 | 230 |
| WAA (9-9) | HDK H15 | 400 | 25.6 | 22.7 | 135 | 22.0 | 1.11 | 333 | 1.3 | 231 |
| WAA (9-10) | HDK H15 | 700 | 25.7 | 22.4 | 154 | 21.5 | 1.36 | 334 | 1.4 | 231 |
| WAA (9-11) | HDK H15 | 1000 | 25.9 | 22.2 | 163 | 21.4 | 1.15 | 332 | 1.4 | 244 |

*1 Units: $10^{-7} \cdot cm^3 \cdot s \cdot g^{-1}$
*2 Ratio of Particles that Passed Through Sieve Having Mesh Opening Size of 150 µm
WARPs: Water Absorbing Resin Particles
WAA: Water Absorbing Agent
C-WARPs: Comparative Water Absorbing Resin Particles
C-WAA: Comparative Water Absorbing Agent A comparison of water absorbing agents (9-1) to (9-4) in Table 7 clearly shows that the SFC improves with increasing amount of silicon dioxide added. The same holds true with the cases of water absorbing agents (9-5) to (9-7) and water absorbing agents (9-8) to (9-11).

was 0.40. Water absorbing resin particles (10) had a centrifuge retention capacity (CRC) of 42 g/g and contained a 13 mass % water-extractable polymer content.

100 mass parts of water absorbing resin particles (10) obtained was evenly mixed with a surface crosslinking agent that was a mixed solution of 0.35 mass parts of 1,4-butanediol, 0.55 mass parts of propylene glycol, and 3.0 mass parts of pure water. The mixture was then heat treated at 212° C. for 40 minutes. Thereafter, the resulting particles were disintegrated until they could pass through a JIS standard sieve having a mesh opening size of 850 μm. Next, the disintegrated particles were subjected to paint shaker test 1, to obtain surface-crosslinked or -coated water absorbing resin particles (10).

A solution was then added to 100 mass parts of surface-crosslinked or -coated water absorbing resin particles (10). The solution was a mixture of 0.9 mass parts of a 27.5 mass % aqueous solution of aluminum sulfate (equivalent to an 8 mass % aqueous solution of aluminum oxide), 0.134 mass parts of a 60 mass % aqueous solution of sodium lactate, and 0.025 mass parts of propylene glycol. After the addition, the particles were dried in a windless environment at 60° C. for 1 hour. Following the drying, the particles were disintegrated until they could pass through a JIS standard sieve having a mesh opening size of 850 μm. The water absorbing resin particles obtained from water absorbing resin particles (10) were designated (10-A).

0.20 mass parts of Aerosil (Registered Trademark) 200 from Nippon Aerosil Co., Ltd. was added to and mixed with 100 mass parts of water absorbing resin particles (10-A) obtained above, to prepare water absorbing agent (10). Table 8 shows the kind and amount of the water-insoluble inorganic particles added, as well as measurements of the CRC, AAP, SFC, D50, and ratio of particles that passed through a sieve having a mesh opening size of 150 μm, and amount of dust, for water absorbing resin particles (10-A) and water absorbing agent (10).

EXAMPLE 11

0.30 mass parts of Aerosil (Registered Trademark) 200 from Nippon Aerosil Co., Ltd. was added to and mixed with 100 mass parts of water absorbing resin particles (10-A) prepared in example 10 to obtain water absorbing agent (11). Table 8 shows the kind and amount of the water-insoluble inorganic particles added, as well as measurements of the CRC, AAP, SFC, D50, ratio of particles that passed through a sieve having a mesh opening size of 150 μm, and amount of dust, for water absorbing agent (11) obtained.

EXAMPLE 12

The same method was used as in example 10 until a comminuted water-containing gel-like crosslinked polymer was obtained.

The comminuted water-containing gel-like crosslinked polymer was spread on a 50-mesh metal net and dried in hot wind at 170° C. for 65 minutes. The dried substance was pulverized in a roll mill and subjected to a classification using a JIS standard sieve having a mesh opening size of 850 μm. The result was water absorbing resin particles (12) which had an irregularly pulverized shape. Particles (12) had a mass median particle size D50 of 330 μm. The logarithmic standard deviation, σζ, of the particle size distribution of particles (12) was 0.35. Water absorbing resin particles (12) had a centrifuge retention capacity (CRC) of 42 g/g and contained a 13 mass % water-extractable polymer content.

100 mass parts of water absorbing resin particles (12) obtained was evenly mixed with a surface crosslinking agent that was a mixed solution of 0.35 mass parts of 1,4-butanediol, 0.55 mass parts of propylene glycol, and 3.0 mass parts of pure water. The mixture was then heat treated at 212° C. for 40 minutes. The resultant particles were disintegrated until they could pass through a JIS standard sieve having a mesh opening size of 850 μm. Next, the disintegrated particles were subjected to paint shaker test 1, to obtain surface-crosslinked or -coated water absorbing resin particles (12).

A solution was then added to 100 mass parts of surface-crosslinked or -coated water absorbing resin particles (12). The solution was a mixture of 0.9 mass parts of a 27.5 mass % aqueous solution of aluminum sulfate (equivalent to an 8 mass % aqueous solution of aluminum oxide), 0.134 mass parts of a 60 mass % aqueous solution of sodium lactate, and 0.025 mass parts of propylene glycol. After the addition, the particles were dried in a windless environment at 60° C. for 1 hour. Following the drying, the particles were disintegrated until they could pass through a JIS standard sieve having a mesh opening size of 850 μm. The water absorbing resin particles obtained from water absorbing resin particles (12) were designated (12-A).

0.20 mass parts of Aerosil (Registered Trademark) 200 from Nippon Aerosil Co., Ltd. was added to and mixed with 100 mass parts of water absorbing resin particles (12-A) obtained above, to prepare water absorbing agent (3C). Table 8 shows the kind and amount of the water-insoluble inorganic particles added, as well as measurements of the CRC, AAP, SFC, D50, ratio of particles that passed through a sieve having a mesh opening size of 150 μm, and amount of dust, for water absorbing agent (12).

EXAMPLE 13

A substance was added to 100 mass parts of surface-crosslinked or -coated water absorbing resin particles (10) prepared in example 10. The substance was a mixture of 0.9 mass parts of a 27.5 mass % aqueous solution of aluminum sulfate (equivalent to an 8 mass % aqueous solution of aluminum oxide), 0.134 mass parts of a 60 mass % aqueous solution of sodium lactate, 0.025 mass parts of propylene glycol, and as a plant component, 0.5 mass parts of a 15 mass % aqueous solution of an extract from leaves of a theaceous plant which contained polyphenol and caffeine ("FS-80MO" available from Shiraimatsu Pharmaceutical Co., Ltd., located at 37-1, Ukawa, Mizuguchi-cho, Kouga-gun, Shiga)). After the addition, the particles were dried in a windless environment at 60° C. for 1 hour. Following the drying, the particles were disintegrated until they could pass through a JIS standard sieve having a mesh opening size of 850 μm, to prepare water absorbing resin particles (13-A).

0.20 mass parts of Aerosil (Registered Trademark) 200 from Nippon Aerosil Co., Ltd. was added to and mixed with 100 mass parts of water absorbing resin particles (13-A) obtained above, to prepare water absorbing agent (13). Table 8 shows the kind and amount of the water-insoluble inorganic particles added, as well as measurements of the CRC, AAP, SFC, D50, ratio of particles that passed through a sieve having a mesh opening size of 150 μm, and amount of dust, for water absorbing agent (13).

EXAMPLE 14

A substance was added to 100 mass parts of surface-crosslinked or -coated water absorbing resin particles (12) prepared in example 12. The substance was a mixture of 0.9 mass parts of a 27.5 mass % aqueous solution of aluminum sulfate (equivalent to an 8 mass % aqueous solution of aluminum oxide), 0.134 mass parts of a 60 mass % aqueous solution of sodium lactate, 0.025 mass parts of propylene glycol, and as a plant component, 0.5 mass parts of a 15 mass % aqueous solution of an extract from leaves of a theaceous plant which contained polyphenol and caffeine ("FS-80MO" available from Shiraimatsu Pharmaceutical Co., Ltd., located at 37-1, Ukawa, Mizuguchi-cho, Kouga-gun, Shiga)). After the addition, the particles were dried in a windless environment at 60° C. for 1 hour. Following the drying, the particles were disintegrated until they could pass through a JIS standard sieve having a mesh opening size of 850 μm, to prepare water absorbing resin particles (14-A).

0.20 mass parts of Aerosil (Registered Trademark) 200 from Nippon Aerosil Co., Ltd. was added to and mixed with 100 mass parts of water absorbing resin particles (14-A) obtained above, to prepare water absorbing agent (14). Table 8 shows the kind and amount of the water-insoluble inorganic particles added, as well as measurements of the CRC, AAP, SFC, D50, ratio of particles that passed through a sieve having a mesh opening size of 150 μm, and amount of dust, for water absorbing agent (14).

COMPARATIVE EXAMPLE 3

0.20 mass parts of Aerosil (Registered Trademark) 200 from Nippon Aerosil Co., Ltd. was added to and mixed with 100 mass parts of water absorbing resin particles (10) prepared in example 10 to obtain comparative water absorbing agent (3). Table 8 shows the kind and amount of the water-insoluble inorganic particles added, as well as measurements of the CRC, AAP, SFC, D50, ratio of particles that passed through a sieve having a mesh opening size of 150 μm, and amount of dust, for comparative water absorbing agent (3) obtained.

COMPARATIVE EXAMPLE 4

0.30 mass parts of Aerosil (Registered Trademark) 200 from Nippon Aerosil Co., Ltd. was added to and mixed with 100 mass parts of water absorbing resin particles (10) obtained in example 10 to obtain comparative water absorbing agent (4). Table 8 shows the kind and amount of the water-insoluble inorganic particles added, as well as measurements of the CRC, AAP, SFC, D50, ratio of particles that passed through a sieve having a mesh opening size of 150 μm, and amount of dust, for comparative water absorbing agent (4) obtained.

COMPARATIVE EXAMPLE 5

The same method was used as in example 10 until a comminuted water-containing gel-like crosslinked polymer was obtained.

The comminuted water-containing gel-like crosslinked polymer was spread on a 50-mesh metal net and dried in hot wind at 170° C. for 65 minutes. The dried substance was pulverized in a roll mill and subjected to a classification using a JIS standard sieve having a mesh opening size of 850 μm. The result was comparative water absorbing resin particles (5) which had an irregularly pulverized shape. Comparative particles (5) had a mass median particle size D50 of 440 μm. The logarithmic standard deviation, σζ, of the particle size distribution of comparative particles (5) was 0.50. Comparative water absorbing resin particles (5) had a centrifuge retention capacity (CRC) of 42 g/g and contained a 13 mass % water-extractable polymer content.

100 mass parts of obtained comparative water absorbing resin particles (5) was evenly mixed with a surface crosslinking agent that was a mixed solution of 0.35 mass parts of 1,4-butanediol, 0.55 mass parts of propylene glycol, and 3.0 mass parts of pure water. The mixture was then heat treated at 212° C. for 40 minutes.

The resultant particles were disintegrated until they could pass through a JIS standard sieve having a mesh opening size of 850 μm. Next, the disintegrated particles were subjected to paint shaker test 1, to obtain surface-crosslinked or -coated comparative water absorbing resin particles (5).

A solution was then added to 100 mass parts of surface-crosslinked or -coated comparative water absorbing resin particles (5). The solution was a mixture of 0.9 mass parts of a 27.5 mass % aqueous solution of aluminum sulfate (equivalent to an 8 mass % aqueous solution of aluminum oxide), 0.134 mass parts of a 60 mass % aqueous solution of sodium lactate, and 0.025 mass parts of propylene glycol. After the addition, the particles were dried in a windless environment at 60° C. for 1 hour. Following the drying, the particles were disintegrated until they could pass through a JIS standard sieve having a mesh opening size of 850 μm. The comparative water absorbing resin particles obtained from comparative water absorbing resin particles (5) was designated (5-A).

0.20 mass parts of Aerosil (Registered Trademark) 200 from Nippon Aerosil Co., Ltd. was added to and mixed with 100 mass parts of comparative water absorbing resin particles (5-A) obtained above, to prepare comparative water absorbing agent (5). Table 8 shows the kind and amount of the water-insoluble inorganic particles added, as well as measurements of the CRC, AAP, SFC, D50, ratio of particles that passed through a sieve having a mesh opening size of 150 μm, and amount of dust, for comparative water absorbing resin particles (5-A) and comparative water absorbing agent (5) obtained.

TABLE 8

|  | *3 mass % | Inorganic Particles Added | Amount Added ppm | CRC g/g | AAP g/g | SFC *1 | D50 μm | *2 mass % | Amount of Dust ppm |
|---|---|---|---|---|---|---|---|---|---|
| WAPRs (10-A) | 0.9 | — | — | 33.9 | 22.2 | 5 | 458 | 2.5 | 215 |
| WAA (10) | 0.9 | Aerosil 200 | 2000 | 34.1 | 19.5 | 15 | 469 | 3.0 | 310 |
| WAA (11) | 0.9 | Aerosil 200 | 3000 | 34.2 | 19.1 | 17 | 460 | 3.1 | 330 |
| WAA (12) | 0.9 | Aerosil 200 | 2000 | 34.2 | 19.5 | 12 | 341 | 3.2 | 322 |
| WAA (13) | 0.9 | Aerosil 200 | 2000 | 34.2 | 19.3 | 14 | 463 | 2.8 | 301 |
| WAA (14) | 0.9 | Aerosil 200 | 2000 | 34.0 | 19.2 | 12 | 342 | 3.1 | 302 |
| C-WAA (3) | — | Aerosil 200 | 2000 | 34.2 | 19.0 | 5 | 463 | 3.0 | 483 |
| C-WAA (4) | — | Aerosil 200 | 3000 | 34.0 | 18.6 | 6 | 467 | 3.4 | 524 |

TABLE 8-continued

| | *3 mass % | Inorganic Particles Added | Amount Added ppm | CRC g/g | AAP g/g | SFC *1 | D50 μm | *2 mass % | Amount of Dust ppm |
|---|---|---|---|---|---|---|---|---|---|
| C-WAPRs (5-A) | 0.9 | — | — | 33.8 | 20.5 | 0 | 443 | 6.3 | 232 |
| C-WAA (5) | 0.9 | Aerosil 200 | 2000 | 33.9 | 18.1 | 6 | 442 | 6.5 | 420 |

*1 Units: $10^{-7} \cdot cm^3 \cdot s \cdot g^{-1}$
*2 Ratio of Particles that Passed Through Sieve Having Mesh Opening Size of 150 μm
*3 Amount of 27.5 mass % Aqueous Solution of Aluminum Sulfate Added
WARPs: Water Absorbing Resin Particles
WAA: Water Absorbing Agent
C-WARPs: Comparative Water Absorbing Resin Particles
C-WAA: Comparative Water Absorbing Agent A comparison of water absorbing agent (10) to comparative water absorbing agent (3) and water absorbing agent (11) to comparative water absorbing agent (4) in Table 8 shows that the use of both a polyvalent metal salt and water-insoluble inorganic particles improved the SFC and reduced the amount of dust while limiting degradation of the AAP. Furthermore, a comparison of water absorbing agent (10) to comparative water absorbing agent (5) show that the SFC decreased at high ratios of particles that passed through a sieve having a mesh opening size of 150 μm.

In addition, the water absorbing resin particles and water absorbing agents to which aluminum sulfate was added produced little dust and exhibited excellent SFCs and AAPs.

Table 9 shows measurements of the $SiO_2$ content in dust and the dust's flyability for the water absorbing agents and comparative water absorbing agents mentioned above.

TABLE 9

| | *3 mass % | Inorganic Particles Added | Amount Added ppm | Amount of Dust ppm | Ratio of $SiO_2$ in Dust mass % | Flyability of Dust |
|---|---|---|---|---|---|---|
| WAA (1-7) | 0.40 | HDK H2050EP | 700 | 219 | 8.0 | 2 |
| WAA (9-6) | 0.40 | Aerosil R-972 | 700 | 238 | 8.1 | 2 |
| WAA (9-3) | 0.40 | HDK H20 | 700 | 230 | 5.2 | 1 |
| WAA (9-4) | 0.40 | HDK H20 | 1000 | 245 | 9.1 | 2 |
| WAA (10) | 0.90 | Aerosil 200 | 2000 | 310 | 41.5 | 4 |
| WAA (11) | 0.90 | Aerosil 200 | 3000 | 330 | 43.1 | 4 |
| WAA (12) | 0.90 | Aerosil 200 | 2000 | 322 | 41.9 | 4 |
| WAA (4-1) | 0.40 | Aerosil 200 | 1000 | 308 | 32.0 | 3 |
| WAA (4-2) | 0.4 | Aerosil 200 | 1250 | 310 | 34.1 | 3 |
| WAA (8-2) | 0.4 | Aerosil 200 | 2000 | 350 | 45.2 | 4 |
| C-WAA (2-2) | — | Aerosil 200 | 3000 | 393 | 66.6 | 5 |
| C-WAA (3) | — | Aerosil 200 | 2000 | 483 | 68.2 | 5 |
| C-WAA (4) | — | Aerosil 200 | 3000 | 524 | 74.6 | 5 |

*2 Ratio of Particles that Passed Through Sieve Having Mesh Opening Size of 150 μm
*3 Amount of 27.5 mass % Aqueous Solution of Aluminum Sulfate Added
WARPs: Water Absorbing Resin Particles
WAA: Water Absorbing Agent
C-WARPs: Comparative Water Absorbing Resin Particles
C-WAA: Comparative Water Absorbing Agent As could be appreciated from Table 9, dust is unlikely to rise when the $SiO_2$ content in the dust is low. It would also be appreciated that the lower the $SiO_2$ content in the dust, the less likely dust rises.

As such, the $SiO_2$ content of the dust is preferably 50 mass % or less, more preferably 30 mass % or less, even more preferably 15 mass % or less, still more preferably 10 mass % or less, most preferably 7 mass % or less.

The present invention is not limited to the description of the embodiments above, but may be altered by a skilled person within the scope of the claims. An embodiment based on a proper combination of technical means disclosed in different embodiments is encompassed in the technical scope of the present invention.

Industrial Applicability

The water absorbing agent and water absorbent core in accordance with the present invention and the water absorbing agent obtained by the manufacturing method for a water absorbing agent in accordance with the present invention have excellent water absorption properties and are unlikely to produce dust, and therefore applicable to water absorbing/retaining agents for various purposes.

Some examples of applications are water absorbing/retaining agents for absorbent articles, such as disposable diapers, sanitary napkins, incontinent pads, and medical pads; agriculture/horticulture water retaining agents, such as bog moss replacements, soil conditioners, water retaining agents, and agricultural effect keeping agents; water retaining agents for construction purposes, such as dew inhibitors for interior wall materials and cement additives; release controlling agents; cold insulators; disposable pocket stoves; sludge coagulating agents; food freshness retaining agents; ion exchange column materials; sludge/oil dehydrates; desiccants; and humidity conditioners.

The water absorbing agent of the present invention is especially suitable for use in disposable diapers, sanitary napkins, and like sanitary/hygienic materials for absorbing feces, urine, or blood.

The invention claimed is:

1. A water absorbing agent containing water absorbing resin particles, the agent satisfying conditions (A) to (H) below:
   (A) the water absorbing resin particles are, on a surface thereof, either crosslinked or coated with a surface crosslinking agent which has at least one hydroxyl group;
   (B) the water absorbing resin particles contain, on a surface thereof, a trivalent water-soluble metal salt and water-insoluble inorganic particles that include silicon dioxide;
   (C) the water absorbing agent has a mass median particle size of 200 μm to 500 μm inclusive;
   (D) the water absorbing agent contains 0.001 to 0.4 mass % inclusive, of the water-insoluble inorganic particles;

(E) the water absorbing resin particles have a size such that no more than 5 mass percent of such particles can pass through a sieve having a mesh opening size of 150 μm;

(F) the water absorbing resin particles contain acid groups that are neutralized in a ratio from 50 mol% to 90 mol% inclusive; and (G) the water absorbing resin particles contain 0.001 to 5.0 mass % inclusive, of the trivalent water-soluble metal salt;

(H) the water absorbing agent contains dust in an amount that is 355 ppm or less and that contains $SiO_2$ in an amount which is 50 mass % or less.

2. The water absorbing agent of claim 1, wherein
the water absorbing agent has a centrifuge retention capacity of 30 g/g inclusive to 50 g/g exclusive, and a saline flow conductivity (SFC) of 10 ($10^{-7} \cdot cm^3 \cdot s \cdot g^{-1}$) or more.

3. A water absorbent core, comprising the water absorbing agent of claim 1.

4. A method of manufacturing a water absorbing agent containing water absorbing resin particles having a mass median particle size of 200 μm to 500 μm inclusive, comprising:

(1) polymerizing a water soluble unsaturated monomer to obtain water absorbing resin particles;

(2) either crosslinking or coating the water absorbing resin particles on a surface thereof with a surface crosslinking agent which has at least one hydroxyl group;

(3) mechanically damaging the water absorbing resin particles, so as to irregularly pulverize such particles; and (4) mixing a trivalent water-soluble metal salt with the water absorbing resin particles;

(5) further mechanically damaging the water absorbing resin particles mixed with the trivalent water-soluble metal salt; and (6) mixing the water absorbing resin particles with water-insoluble inorganic particles that include silicon dioxide, wherein the water absorbing agent contains dust in an amount that is 355 ppm or less and that such dust contains $SiO_2$ in an amount which is 50 mass % or less.

5. The method of claim 4, wherein
the water absorbing agent has a centrifuge retention capacity of 30 g/g inclusive to 50 g/g exclusive, and a saline flow conductivity (SFC) of 10 ($10^{-7} \cdot cm^3 \cdot s \cdot g^{-1}$) or more.

6. The method of claim 4, wherein the mixing the trivalent water-soluble metal salt comprises mixing the trivalent water-soluble metal salt as an aqueous solution with the water absorbing resin particles.

\* \* \* \* \*